US008642339B2

(12) United States Patent
Sato et al.

(10) Patent No.: US 8,642,339 B2
(45) Date of Patent: Feb. 4, 2014

(54) CULTURE MEDIUM FOR EPITHELIAL STEM CELLS AND ORGANOIDS COMPRISING THE STEM CELLS

(75) Inventors: Toshiro Sato, Hilversum (NL); Johannes Carolus Clevers, Huis ter Heide (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 0 days.

(21) Appl. No.: 13/147,163

(22) PCT Filed: Feb. 3, 2010

(86) PCT No.: PCT/NL2010/000017
§ 371 (c)(1),
(2), (4) Date: Sep. 14, 2011

(87) PCT Pub. No.: WO2010/090513
PCT Pub. Date: Aug. 12, 2010

(65) Prior Publication Data
US 2012/0028355 A1 Feb. 2, 2012

Related U.S. Application Data

(60) Provisional application No. 61/149,622, filed on Feb. 3, 2009.

(30) Foreign Application Priority Data

Feb. 3, 2009 (EP) ..................................... 09151970
Sep. 30, 2009 (EP) ..................................... 09171831

(51) Int. Cl.
C12N 5/02 (2006.01)

(52) U.S. Cl.
USPC ........................... 435/406; 435/325; 435/405

(58) Field of Classification Search
None
See application file for complete search history.

(56) References Cited

U.S. PATENT DOCUMENTS

| 5,464,758 A | 11/1995 | Gossen et al. |
| 6,165,782 A | 12/2000 | Naldini et al. |
| 6,207,455 B1 | 3/2001 | Chang |
| 6,218,181 B1 | 4/2001 | Verma et al. |
| 6,277,633 B1 | 8/2001 | Olsen |
| 6,323,031 B1 | 11/2001 | Cichutek |
| 6,432,705 B1 | 8/2002 | Yee et al. |
| 7,411,052 B2 | 8/2008 | Tang |
| 7,439,927 B2 | 10/2008 | Lenart et al. |
| 7,541,431 B2 | 6/2009 | Yoon |
| 2003/0032034 A1 | 2/2003 | Tang |
| 2005/0054829 A1 | 3/2005 | Wiley et al. |
| 2007/0020637 A1 | 1/2007 | Isogai et al. |
| 2007/0036769 A9* | 2/2007 | Li et al. ...................... 424/93.21 |
| 2007/0244061 A1 | 10/2007 | Niehrs et al. |
| 2008/0113433 A1* | 5/2008 | Robins et al. .................. 435/377 |
| 2008/0233088 A1* | 9/2008 | Guha et al. .................. 424/93.7 |
| 2009/0311748 A1 | 12/2009 | Isogai et al. |
| 2010/0047853 A1* | 2/2010 | Kuo et al. ....................... 435/34 |
| 2010/0071078 A1 | 3/2010 | Niehrs |
| 2010/0137210 A1 | 6/2010 | Funk et al. |
| 2010/0247648 A1 | 9/2010 | Grubb et al. |
| 2010/0275280 A1 | 10/2010 | Clevers et al. |
| 2010/0278800 A1 | 11/2010 | Boyle et al. |
| 2012/0196312 A1 | 8/2012 | Sato et al. |

FOREIGN PATENT DOCUMENTS

| EP | 1347046 A1 | 9/2003 |
| EP | 1440981 A2 | 7/2004 |
| EP | 2157192 A1 | 2/2010 |
| EP | 1673475 B1 | 4/2010 |
| EP | 2228443 A1 | 9/2010 |
| EP | 1427747 B1 | 4/2012 |
| EP | 1727560 B1 | 9/2012 |
| WO | WO 01/77169 A2 | 10/2001 |
| WO | WO 02/18544 A2 | 3/2002 |
| WO | WO 03/029405 A2 | 4/2003 |
| WO | WO 03/029437 A2 | 4/2003 |
| WO | WO 03/054152 A2 | 7/2003 |
| WO | WO 2004/087896 A2 | 10/2004 |
| WO | WO 2005/040418 A2 | 5/2005 |
| WO | WO 2005/072419 A2 | 8/2005 |
| WO | WO 2005/110009 A2 | 11/2005 |
| WO | WO 2005/117994 A2 | 12/2005 |
| WO | WO 2006/104536 A2 | 10/2006 |
| WO | WO 2007/013666 A2 | 2/2007 |
| WO | WO 2007/030290 A2 | 3/2007 |

(Continued)

OTHER PUBLICATIONS

Crosnier et al., "Organizing cell renewal in the intestine: stem cells, signals and combinatorial control", Nature reviews?Genetics, May 2006, vol. 7, pp. 349-359.*
Malorni et al., "The antioxidant N-acetyl-cysteine protects cultured epithelial cells from menadione-induced cytopathology", Chemico-Biological Interactions, 1995, vol. 96, pp. 113-123.*
Abe K, Watanabe S. (1995) Apoptosis of mouse pancreatic acinar cells after duct ligation.Arch Histol Cytol. 58:221-9.
Apelqvist A, Li H, Sommer L, Beatus P, Anderson DJ, Honjo T, Hrabe de Angelis M, Lendahl U, Edlund H. (1999) Notch signalling controls pancreatic cell differentiation. Nature 400:877-81.
Barker et al., Tissue-Resident Adult Stem Cell Populations of Rapidly Self-Renewing Organs, Cell Stem Cell, 2010, pp. 656-670, vol. 7.

(Continued)

Primary Examiner — Laura Schuberg
(74) Attorney, Agent, or Firm — Wolf, Greenfield & Sacks, P.C.

(57) ABSTRACT

The invention relates to a method for culturing epithelial stem cells, isolated tissue fragments comprising the epithelial stem cells, or adenoma cells, and culturing the cells or fragments in the presence of a Bone Morphogenetic Protein (BMP) inhibitor, a mitogenic growth factor, and a Wnt agonist when culturing epithelial stem cells and isolated tissue fragments. The invention further relates to a cell culture medium comprising a BMP inhibitor, a mitogenic growth factor, and a Wnt agonist, to the use of the culture medium, and to crypt-villus organoids, gastric organoids and pancreatic organoids that are formed in the culture medium.

35 Claims, 42 Drawing Sheets

(56) References Cited

FOREIGN PATENT DOCUMENTS

| | | |
|---|---|---|
| WO | WO 2007/050043 A2 | 5/2007 |
| WO | WO 2007/100357 A2 | 9/2007 |
| WO | WO 2007/127454 A2 | 11/2007 |
| WO | WO 2008/020942 A2 | 2/2008 |
| WO | WO 2008/046649 A1 | 4/2008 |
| WO | WO 2008/075796 A1 | 6/2008 |
| WO | WO 2008/088524 A2 | 7/2008 |
| WO | WO2008/101215 | 8/2008 |
| WO | WO 2008/101215 A | 8/2008 |
| WO | WO 2008/155120 A2 | 12/2008 |
| WO | WO 2009/005809 A2 | 1/2009 |
| WO | WO 2009/022907 A2 | 2/2009 |
| WO | WO 2010/016766 A2 | 2/2010 |
| WO | WO 2010/077681 A1 | 7/2010 |
| WO | WO 2010/090513 A2 | 8/2010 |
| WO | WO 2010/108001 A2 | 9/2010 |
| WO | WO 2010/121923 A1 | 10/2010 |
| WO | WO 2012/014076 A2 | 2/2012 |
| WO | WO 2012/140274 A2 | 10/2012 |
| WO | WO 2012/168930 A1 | 12/2012 |

OTHER PUBLICATIONS

Barker, N., van de Wetering, M. & Clevers, H. The intestinal stem cell. Genes Dev 22, 1856-64 (2008).

Baffle, E. et al. Beta-catenin and TCF mediate cell positioning in the intestinal epithelium by controlling the expression of EphB/ephrinB. Cell 111, 251-63 (2002).

Binnerts Me et al, R-Spondin1 regulates Wnt signaling by inhibiting internalization of LRP6, PNAS, 104:14700-5 (2007).

Bjerknes and Cheng, Rapid Communications, Gastroenterology, 1999, 116, 7-14.

Bjerknes and Cheng, Multipotential stem cells in adult mouse gastric epithelium, Am J Physiol Gastrointest Liver Physiol. Sep. 2002;283(3):G767-77.

Bonner-Weir, S., Taneja, M., Weir, G.C., Tatarkiewicz, K., Song, K.H., Sharma, A., and O'Neil, J.J. (2000). In vitro cultivation of human islets from expanded ductal tissue. Proc. Natl. Acad. Sci. USA 97, 7999-8004.

Bonner-Weir, S., and Weir, G.C. (2005). New sources of pancreatic beta-cells. Nat. Biotechnol. 23, 857-861.

Bouwens, L., and Rooman, I. (2005). Regulation of pancreatic beta-cell mass. Physiol. Rev. 85, 1255-1270.

Chen et al, Small molecule-mediated disruption of Wnt-dependent signaling in tissue regeneration and cancer, Nat Chem Biol., Feb. 2009;5(2):100-7.

Cheng, H. & Leblond, C. P. Origin, differentiation and renewal of the four main epithelial cell types in the mouse small intestine. I. Columnar cell. Am J Anat 141, 461-79 (1974).

Dignass, A. U. & Sturm, A. Peptide growth factors in the intestine. Eur J Gastroenterol Hepatol 13, 763-70 (2001).

Dontu et al., Role of Notch signaling in cell-fate determination of human mammary stem/progenitor cells, Breast Cancer Res, 2004, 6: R605-R615.

Dor, Y., Brown, J., Martinez, O.I., and Melton, D.A. (2004). Adult pancreatic beta-cells are formed by self-duplication rather than stem-cell differentiation. Nature 429, 41-46.

Evans, G. S., Flint, N., Somers, A. S., Eyden, B. & Potten, C. S. The development of a method for the preparation of rat intestinal epithelial cell primary cultures. J Cell Sci 101 ( Pt 1), 219-31 (1992).

Fukamachi, H. Proliferation and differentiation of fetal rat intestinal epithelial cells in primary serum-free culture. J Cell Sci 103 ( Pt 2), 511-9 (1992).

Githens S, Schexnayder JA, Desai K, Patke CL. (1989) Rat pancreatic interlobular duct epithelium: isolation and culture in collagen gel. In Vitro Cell Dev Biol. 25:679-88.

Gradwohl, G., Dierich, A., LeMeur, M., and Guillemot, F. (2000). neurogenin3 is required for the development of the four endocrine cell lineages of the pancreas. Proc. Natl. Acad. Sci. USA 97, 1607-1611.

Gregorieff and Clevers, Wnt signaling in the intestinal epithelium: from endoderm to cancer, Genes Dev, 2005, 19, 877-90.

Gu, G., Dubauskaite, J., and Melton, D.A. (2002). Direct evidence for the pancreatic lineage: NGN3+ cells are islet progenitors and are distinct from duct progenitors. Development 129, 2447-2457.

Hao, E., Tyrberg, B., Itkin-Ansari, P., Lakey, J.R., Geron, I., Monosov, E.Z., Barcova, M., Mercola, M., and Levine, F. (2006). Beta-cell differentiation from nonendocrine epithelial cells of the adult human pancreas. Nat. Med. 12, 310-316.

Hofmann, C. et al. Cell-cell contacts prevent anoikis in primary human colonic epithelial cells. Gastroenterology 132, 587-600 (2007).

Hsieh et al., Truncated Mammalian Notch1 Activates CBF1;RBPJk-Represeed Genes by a Mechanism Resembling That of Epstein-Barr Virus EBNA2, Mol. Cell. Biol., 1996, 16, 952-959.

Huch et al., Urokinase-Type Plasminogen Activator Receptor Transcriptionally Controlled Adenoviruses Eradicate Pancreatic Tumors and Live Metastasis in Mouse Models, Neoplasia, 2009, pp. 518-528, vol. 11, No. 6.

Jaks V, Barker N, Kasper M, van Es JH, Snippert HJ, Clevers H, Toftgård R. (2008) Lgr5 marks cycling, yet long-lived, hair follicle stem cells. Nat Genet. 40:1291-9.

Jensen, T-box Genes in Early Embryogenesis, Developmental Dynamics, 2004, pp. 201-218, vol. 229.

Kedinger, M. et al. Intestinal epithelial-mesenchymal cell interactions. Ann N Y Acad Sci 859, 1-17 (1998).

Planutis, Kestutis et al. Regulation of norrin receptor frizzled-4 by Wnt2 in colon-derived cells, BMC Cell Biol. (2007) 8: 12.

Kirikoshi H et al. WNT10A and WNT6, Clustered in Human Chromosome 2q35 Region with Head-to-Tail Manner, Are Strongly Coexpressed in SW480 Cells, Biochem Biophys Res Com, 2001, 283: 798-805.

Korinek et al., Constitutive Transcriptional Activation by a $\beta$-Cantenin-Tef Complex in APC$^{-/-}$ Colon Carcinoma, Science, 1997, 275:1784-1787.

Korinek, V. et al. Depletion of epithelial stem-cell compartments in the small intestine of mice lacking Tcf-4. Nat Genet 19, 379-83 (1998).

Kuhnert, F. et al. Essential requirement for Wnt signaling in proliferation of adult small intestine and colon revealed by adenoviral expression of Dickkopf-1. Proc Natl Acad Sci U S A 101, 266-71 (2004).

Lefebvre VH, Otonkoski T, Ustinov J, Huotari MA, Pipeleers DG, Bouwens L.(1998) Culture of adult human islet preparations with hepatocyte growth factor and 804G matrix is mitogenic for duct cells but not for beta-cells. Diabetes. 47:134-7.

Leost, M. et al. Paullones are potent inhibitors of glycogen synthase kinase-3$\beta$ and cyclin-dependent kinase 5/p25, Eur. J. Biochem. (2000) 267, 5983-5994.

Li, L. et al. The human homolog of rat Jagged1 expressed by marrow stroma inhibits differentiation of 32D cells through interaction with Notch1. Immunity 8, 43-55 (1998).

Li, L. & Xie, T. Stem cell niche: structure and function. Annu Rev Cell Dev Biol 21, 605-31 (2005).

Liao et al Glycogen Synthase Kinase-3$\beta$ Activity Is Required for Androgen-Stimulated Gene Expression in Prostate Cancer, Endocrinology, 2004, 145(6): 2941-9.

Little et al., Engineering Biomaterials for Synthetic Neural Stem Cell Microenvironments, Chem. Rev, 2008, 108, 1787-1796.

Liu et al. A Small-Molecule Agonist of the Wnt Signaling Pathway, Angew Chem Int Ed Engl. (2005) 44, 1987-90.

Lustig B, Jerchow B, Sachs M, Weiler S, Pietsch T, Karsten U, van de Wetering M, Clevers H, Schlag PM, Birchmeier W, Behrens J. (2002) Negative feedback loop of Wnt signaling through upregulation of conductin/axin2 in colorectal and liver tumors, J. Mol Cell Biol. 1184-93.

Meijer, L. et al. GSK-3-Selective Inhibitors Derived from Tyrian Purple Indirubins, Chem. Biol. (2003) 10, 1255-1266.

Meijer et al., Pharmacological inhibitors of glycogen synthase kinase 3, Trends in Pharmacological Sciences (2004) 25, 471-480.

(56) References Cited

OTHER PUBLICATIONS

Miralles F, Czernichow P, Ozaki K, Itoh N, Scharfmann R. (1999) Signaling through fibroblast growth factor receptor 2b plays a key role in the development of the exocrine pancreas. Proc Natl Acad Sci U S A. 96:6267-72.

Ootani A, Toda S, Fujimoto K, Sugihara H. Foveolar Differentiation of Mouse Gastric Mucosa in Vitro, Am J Pathol. Jun. 2003;162(6):1905-12.

Perreault, N. & Jean-Francois, B. Use of the dissociating enzyme thermolysin to generate viable human normal intestinal epithelial cell cultures. Exp Cell Res 224, 354-64 (1996).

Pinto, D., Gregorieff, A., Begthel, H. & Clevers, H. Canonical Wnt signals are essential for homeostasis of the intestinal epithelium. Genes Dev 17, 1709-13 (2003).

Powell, D. W. et al. Myofibroblasts. II. Intestinal subepithelial myofibroblasts. Am J Physiol 277, C183-201 (1999).

Ramiya, V.K., Maraist, M., Arfors, K.E., Schatz, D.A., Peck, A.B., and Cornelius, J.G. (2000). Reversal of insulin-dependent diabetes using islets generated in vitro from pancreatic stem cells. Nat. Med. 6, 278-282.

Rooman I, Heremans Y, Heimberg H, Bouwens L. Modulation of rat pancreatic acinoductal transdifferentiation and expression of PDX-1 in vitro. Diabetologia, Jul. 2000;43(7):907-14.

Rooman I, Lardon J, Flamez D, Schuit F, Bouwens L. (2001) Mitogenic effect of gastrin and expression of gastrin receptors in duct-like cells of rat pancreas. Gastroenterology 121:940-9.

Saha et al., Designing synthetic materials to control stem cell phenotype, Curr Opin Chem Biol., 2007, 11(4): 381-387.

Saha et al., Substrate Modulus Directs Neural Stem Cell Behavior, Biophysical Journal, 2008, 95: 4426-4438.

Sasaki, T., Giltay, R., Talts, U., Timpl, R. & Talts, J. F. Expression and distribution of laminin alpha1 and alpha2 chains in embryonic and adult mouse tissues: an immunochemical approach. Exp Cell Res 275, 185-99 (2002).

Sawada et al. Selective killing of Paneth cells by intravenous administration of dithizone in rats, Int J Exp Pathol;72:407-21 (1991).

Schwitzgebel, V.M., Scheel, D.W., Conners, J.R., Kalamaras, J., Lee, J.E., Anderson, D.J., Sussel, L., Johnson, J.D., and German, M.S. (2000). Expression of neurogenin3 reveals an islet cell precursor population in the pancreas. Development 127, 3533-3542.

Seaberg, R.M., Smukler, S.R., Kieffer, T.J., Enikolopov, G., Asghar, Z., Wheeler, M.B., Korbutt, G., and van der Kooy, D. (2004). Clonal identification of multipotent precursors from adult mouse pancreas that generate neural and pancreatic lineages. Nat. Biotechnol. 22, 1115-1124.

Soriano, P. Generalized lacZ expression with the ROSA26 Cre reporter strain. Nat Genet 21, 70-1 (1999).

Spradling, A., Drummond-Barbosa, D. & Kai, T. Stem cells find their niche. Nature 414, 98-104 (2001).

Srinivas, S. et al. Cre reporter strains produced by targeted insertion of EYFP and ECFP into the ROSA26 locus. BMC Dev Biol 1, 4 (2001).

St Clair, W. H. & Osborne, J. W. Crypt fission and crypt number in the small and large bowel of postnatal rats. Cell Tissue Kinet 18, 255-62 (1985).

Stingl, J., Eaves, C. J., Zandieh, I. & Emerman, J. T. Characterization of bipotent mammary epithelial progenitor cells in normal adult human breast tissue. Breast Cancer Res Treat 67, 93-109 (2001).

Stingl, J. et al. Purification and unique properties of mammary epithelial stem cells. Nature 439, 993-7 (2006).

Suzuki, A., Nakauchi, H., and Taniguchi, H. (2004). Prospective isolation of multipotent pancreatic progenitors using flow-cytometric cell sorting. Diabetes 53, 2143-2152.

Teta, M., Rankin, M.M., Long, S.Y., Stein, G.M., and Kushner, J.A. (2007). Growth and regeneration of adult beta cells does not involve specialized progenitors. Dev. Cell 12, 817-826.

Trautmann B, Schlitt HJ, Hahn EG, Löhr M. (1993) Isolation, culture, and characterization of human pancreatic duct cells. Pancreas 8:248-54.

van de Wetering et al., Mutant E-cadherin Breast Cancer Cells Do Not Display Constitutive Wnt Signaling, Cancer Res., Jan. 1, 2001;61(1):278-84.

van Es, J. H. et al. Notch/gamma-secretase inhibition turns proliferative cells in intestinal crypts and adenomas into goblet cells. Nature 435, 959-63 (2005).

Wang, R.N., Kloppel, G., and Bouwens, L. (1995). Duct- to islet-cell differentiation and islet growth in the pancreas of duct-ligated adult rats. Diabetologia 38, 1405-1411.

Watanabe, K. et al. A Rock inhibitor permits survival of dissociated human embryonic stem cells. Nat Biotechnol 25, 681-6 (2007).

Whitehead, R. H., Demmler, K., Rockman, S. P. & Watson, N. K. Clonogenic growth of epithelial cells from normal colonic mucosa from both mice and humans. Gastroenterology 117, 858-65 (1999).

Willert K, Brown JD, Danenberg E, Duncan AW, Weissman IL, Reya T, Yates Jr 3rd, Nusse R. Wnt proteins are lipid-modified and can act as stem cell growth factors, Nature. May 22, 2003;423(6938):448-52.

Xu X, D'Hoker J, Stangé G, Bonné S, De Leu N, Xiao X, Van de Casteele M, Mellitzer G, Ling Z, Pipeleers D, Bouwens L, Scharfmann R, Gradwohl G, Heimberg H. (2008) Beta cells can be generated from endogenous progenitors in injured adult mouse pancreas. Cell. 132(2):197-207.

Yen, T. H. & Wright, N. A. The gastrointestinal tract stem cell niche. Stem Cell Rev 2, 203-12 (2006).

Partial European search report for Application No. 09151970.2 dated Dec. 6, 2009.

van der Flier, L.G., van Gijn, M.E., .., and Clevers H. Transcription factor Achaete scute-like 2 (Ascl2) controls intestinal stem cell fate Cell 136: 903-12 (2009).

Barker, N, Huch, M., . . . , and Hans Clevers. Lgr5+ve stem cells drive self-renewal in the stomach and build long-lived gastric units in vitro Cell Stem Cell, 6: 25-36 (2010).

van de Wetering M et al. The β-Catenin/TCF-4 Complex Imposes a Crypt Progenitor Phenotype on Colorectal Cancer Cells, Cell 2002;111:241-50.

Visco et al., Differential Response to Keratinocyte Growth Factor Receptor and Epidermal Growth Factor Receptor Ligands of Proliferating and Differentiating Intestinal Epithelial Cells, J. Cell. Physiol. 200, 31-44 (2004).

Chapman et al., Analysis of Spatial and Temporal Gene Expression Patterns in Blastula and Gastrula Stage, Dev. Biol. 245, 187-199 (2002).

Kadesch et al., Notch Signaling: A Dance of Proteins Changing Partners, Exp. Cell. Res. 260, 1-8 (2000).

Abud et al., Growth of intestinal epithelium in organ culture is dependent on EGF signalling, Experimental Cell Research, Feb. 15, 2005, pp. 252-262, vol. 303, No. 2, Academic Press, US.

Bjerknes, et al., Intestinal epithelial stem cells and progenitors, Methods in Enzymology, Jan. 1, 2006, pp. 337-383, vol. 419, Academic Press Inc., San Diego, CA, US.

Booth et al., Maintenance of functional stem cells in isolated and cultured adult intestinal epithelium, Experimental Cell Research, Jun. 15, 1999, pp. 359-366, vol. 249, No. 2, Academic Press, US.

Haramis et al., De novo crypt formation and juvenile polyposis on BMP inhibition in mouse intestine, Science, Mar. 12, 2004, pp. 1684-1686, vol. 303, No. 5664, Washington, DC.

Kim et al., Mitogenic Influence of Human R-Spondin1 on the Intestinal Epithelium, Science, Aug. 19, 2005, pp. 1256-1259, American Association for the Advancement of Science, US, Washington, DC.

Barker et al., Identification of stem cells in small intestine and colon by marker gene Lgr5, Nature, Oct. 25, 2007, pp. 1003-1008, vol. 449, Nature Publishing Group, London, GB.

Sato et al., Single Lgr5 stem cells build crypt-villus structures in vitro without a mesenchymal niche, Nature, May 14, 2009, pp. 262-265, vol. 459, No. 7244.

PCT International Search Report, PCT/NL2010/000017, dated Oct. 8, 2010.

Booth et al., The isolation and Culture of Adult Mouse Colonic Epithelium, Epithelial Cell Biology, Jan. 1, 1995, pp. 76-86, vol. 4, No. 2, Springer International, Berlin, DE.

Partial European Search Report for 09151970.2-2403 dated Jun. 12, 2009.

Biotechnology Journal, 2007, pp. 701-705 vol. 11-12.

(56) References Cited

OTHER PUBLICATIONS

G.I. Research, 2004, pp. 3-10, vol. 12, No. 2.

Gastroenterology, 2005, p. A702, vol. 128, No. 4, Suppl. 2.

Horikoshi et al., High-Speed Knock-In, Functional analyses of secreted proteins by High-Speed Knock-In (HSKI) system II: Intestinotrophic activities of R-spondin family proteins, 2007, 3P-1232.

Mori et al., Micropatterned Organoid Culture of Rat Hepatocytes and HepG2 Cells, Journal of Bioscience and Bioengineering, 2008, pp. 237-242, vol. 106, No. 3.

Notice of Reasons for Rejection on copending Japanese application 2011-547839, Drafting Date: Aug. 29, 2012; Dispatch Date: Sep. 3, 2012, translation also provided.

Rokutan et al., Epidermal growth factor-induced mitogen signals in cultured intestinal epithelial cells, J. Gastroenterol, 1994, pp. 59-62, vol. 29 [Suppl VII].

Schroter et al., Detection of myosin light chain phosphorylation—A cell-based assay for screening Rho-kinase inhibitors, Biochemical and Biophysical Research Communications, 2008, pp. 356-360, vol. 374.

(Japanese) Infection, inflammation and immunity 34(2), 40-52 (2004).

(Japanese) Egan et al., Notch Receptors, Partners and Regulators—From Conserved Domains to Powerful Functions, Experimental Medicine 16(3) 200-229 (1998).

Thomas et al., Role of Gastrointestinal Hormones in the Proliferation of Normal and Neoplastic Tissues, Endocrine Reviews, 2003, pp. 571-599, vol. 24, No. 5, The Endocrine Society.

Wang et al., Regulation of TRAIL Expression by the Phosphatidylinositol 3-Kinase/Akt/GSK-3 Pathway in Human Colon Cancer Cells, The Journal of Biological Chemistry, 2002, pp. 36602-36610, vol. 277, No. 39.

U.S. Appl. No. 60/339,739, filed Dec. 10, 2001, Tang et al.

[No Author Listed] An open label dose-escalation study of a self-complementary adeno-associated viral vector (scAAV2/8-LP1-hFIXco) for gene transfer in hemophilia B. ClinicalTrials.gov Archive. Jun. 29, 2010. Identifier NCT00979238. http://clinicaltrials.gov/archive/NTC00979238/2010_06_29. 3 pages.

[No Author Listed] The Wnt family of secreted proteins. R&D Systems. Jan. 1, 2004. http://www.rndsystems.com/mini_review_detail_objectname_MR04_WntFamily.aspx. 7 pages.

Amado et al., Lentiviral vectors—the promise of gene therapy within reach? Science. Jul. 30, 1999;285(5428):674-6.

Anderson, Human gene therapy. Nature. Apr. 30, 1998;392(6679 Suppl):25-30.

Azuma et al., Robust expansion of human hepatocytes in Fah-/-/Rag2-/-/Il2rg-/- mice. Nat Biotechnol. Aug. 2007;25(8):903-10. Epub Jul. 29, 2007. Author manuscript available in PMC Jul. 25, 2012.

Bainbridge et al., Effect of gene therapy on visual function in Leber's congenital amaurosis. N Engl J Med. May 22, 2008;358(21):2231-9. doi: 10.1056/NEJMoa0802268. Epub Apr. 27, 2008.

Brewer et al., Optimized survival of hippocampal neurons in B27-supplemented Neurobasal, a new serum-free medium combination. J Neurosci Res. Aug. 1, 1993;35(5):567-76.

Brinster et al., Regulation of metallothionein—thymidine kinase fusion plasmids injected into mouse eggs. Nature. Mar. 4, 1982;296(5852):39-42.

Caplen et al., Specific inhibition of gene expression by small double-stranded RNAs in invertebrate and vertebrate systems. Proc Natl Acad Sci U S A. Aug. 14, 2001;98(17):9742-7. Epub Jul. 31, 2001.

Chun et al., A new selective and potent inhibitor of human cytochrome P450 1B1 and its application to antimutagenesis. Cancer Res. Nov. 15, 2001;61(22):8164-70. Erratum in: Cancer Res Feb. 15, 2002;62(4):1232.

Clotman et al., Control of liver cell fate decision by a gradient of TGFβ signaling modulated by Onecut transcription factors. Genes & Dev. 2005;19:1849-54.

De Gouville et al., Inhibition of TGF-β signaling by an ALK5 inhibitor protects rats from dimethylnitrosamine-induced liver fibrosis. Br J Pharmacol. May 2005;145(2):166-77.

Elbashir et al., Duplexes of 21-nucleotide RNAs mediate RNA interference in cultured mammalian cells. Nature. May 24, 2001;411(6836):494-8.

Federico, Lentiviruses as gene delivery vectors. Curr Opin Biotechnol. Oct. 1999;10(5):448-53.

Fuchs, Inhibition of TGF-62 signaling for the treatment of tumor metastasis and fibrotic diseases. Curr Signal Transduction Ther. 2011;6:39-43.

Furth et al., Temporal control of gene expression in transgenic mice by a tetracycline-responsive promoter. Proc Natl Acad Sci U S A. Sep. 27, 1994;91(20):9302-6.

Furuyama et al., Continuous cell supply from a Sox9-expressing progenitor zone in adult liver, exocrine pancreas and intestine. Nat Genet. Jan. 2011;43(1):34-41. doi: 10.1038/ng.722. Epub Nov. 28, 2010.

Gao et al., Biology of AAV serotype vectors in liver-directed gene transfer to nonhuman primates. Mol Ther. Jan. 2006;13(1):77-87. Epub Oct. 10, 2005.

Geiduschek et al., Transcription by RNA polymerase III. Annu Rev Biochem. 1988;57:873-914.

Gonçalves et al., Adeno-associated virus: from defective virus to effective vector. Virol J. 2005;2:43. 17 pages.

Gossen et al., Tight control of gene expression in mammalian cells by tetracycline-responsive promoters. Proc Natl Acad Sci U S A. Jun. 15, 1992;89(12):5547-51.

Gupta et al., Compilation of small RNA sequences. Nucleic Acids Res. Apr. 25, 1991;19 Suppl:2073-5.

Herbst, Review of epidermal growth factor receptor biology. Int J Radiat Oncol Biol Phys. 2004;59(2 Suppl):21-6.

Hernandez, Small nuclear RNA genes: A model system to study fundamental mechanisms of transcription. J Biol Chem. Jul. 20, 2001;276(29):26733-6. Epub Jun. 4, 2001.

Howe et al., The responsiveness of a tetracycline-sensitive expression system differs in different cell lines. J Biol Chem. 1995 Jun. 9, 1995;270(23):14168-74.

Hu et al., Wnt/β-catenin signaling in murine hepatic transit amplifying progenitor cells. Gastroenterology. Nov. 2007;133(5):1579-91. Epub Aug. 28, 2007.

Igarashi et al., Characterization of recombinant human fibroblast growth factor (FGF)-10 reveals functional similarities with keratinocyte growth factor (FGF-7). J Biol Chem. May 22, 1998;273(21):13230-5.

Kaplitt et al., Safety and tolerability of gene therapy with an adeno-associated virus (AAV) borne GAD gene for Parkinson's disease: an open label, phase I trial. Lancet. Jun. 23, 2007;369(9579):2097-105.

Kay et al., Viral vectors for gene therapy: the art of turning infectious agents into vehicles of therapeutics. Nat Med. Jan. 2001;7(1):33-40.

Lemaigre, Mechanisms of liver development: concepts for understanding liver disorders and design of novel therapies. Gastroenterology. Jul. 2009;137(1):62-79.

Leost et al., Paullones are potent inhibitors of glycogen synthase kinase-3beta and cyclin-dependent kinase 5/p25. Eur J Biochem. Oct. 2000;267(19):5983-94.

Mader et al., A steroid-inducible promoter for the controlled overexpression of cloned genes in eukaryotic cells. Proc Natl Acad Sci U S A. Jun. 15, 1993;90(12):5603-7.

Maguire et al., Safety and efficacy of gene transfer for Leber's congenital amaurosis. N Engl J Med. May 22, 2008;358(21):2240-8. Epub 2008 Apr. 27, 2008. Author manuscript available in PMC Mar. 1, 2010.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Marin et al., Towards efficient cell targeting by recombinant retroviruses. Mol Med Today. Sep. 1997;3(9):396-403.

Mattaj et al., Changing the RNA polymerase specificity of U snRNA gene promoters. Cell. Nov. 4, 1988;55(3):435-42.

(56) References Cited

OTHER PUBLICATIONS

Mayo et al., The mouse metallothionein-I gene is transcriptionally regulated by cadmium following transfection into human or mouse cells. Cell. May 1982;29(1):99-108.
McEwen et al., Regulation of the fibroblast growth factor receptor 3 promoter and intron I enhancer by Sp1 family transcription factors. J Biol Chem. Feb. 27, 1998;273(9):5349-57.
Metzger et al., The human oestrogen receptor functions in yeast. Nature. Jul. 7, 1988;334(6177):31-6.
Mitaka, Reconstruction of hepatic organoid by hepatic stem cells. J Hepatobiliary Pancreat Surg. 2002;9(6):697-703.
Myslinski et al., An unusually compact external promoter for RNA polymerase III transcription of the human H1RNA gene. Nucleic Acids Res. Jun. 15, 2001;29(12):2502-9.
Overturf et al., Hepatocytes corrected by gene therapy are selected in vivo in a murine model of hereditary tyrosinaemia type I. Nat Genet. Mar. 1996;12(3):266-73.
Peng et al., Viral vector targeting. Curr Opin Biotechnol. Oct. 1999;10(5):454-7.
Reiser, Production and concentration of pseudotyped HIV-1-based gene transfer vectors. Gene Ther. Jun. 2000;7(11):910-3.
Resnitzky et al., Acceleration of the G1/S phase transition by expression of cyclins D1 and E with an inducible system. Mol Cell Biol. Mar. 1994;14(3):1669-79.
Russell, Update on adenovirus and its vectors. J Gen Virol. Nov. 2000;81(Pt 11):2573-604.
Sato et al., Long-term expansion of epithelial organoids from human colon, adenoma, adenocarcinoma, and Barrett's epithelium. Gastroenterology. Nov. 2011;141(5):1762-72.
Shockett et al., A modified tetracycline-regulated system provides autoregulatory, inducible gene expression in cultured cells and transgenic mice. Proc Natl Acad Sci U S A. Jul. 3, 1995;92(14):6522-6.
Snykers et al., Differentiation of neonatal rat epithelial cells from biliary origin into immature hepatic cells by sequential exposure to hepatogenic cytokines and growth factors reflecting liver development. Toxicol in Vitro. Oct. 2007;21(7):1325-31. Epub Apr. 4, 2007.
Snykers et al., In vitro differentiation of embryonic and adult stem cells into hepatocytes: state of the art. Stem Cells. Mar. 2009;27(3):577-605.
Sommerfelt, Retrovirus receptors. J Gen Virol. Dec. 1999;80 ( Pt 12):3049-64.
St Clair et al , Inhibition by ganciclovir of cell growth and DNA synthesis of cells biochemically transformed with herpesvirus genetic information. Antimicrob Agents Chemother. Jun. 1987;31(6):844-9.
Stroes et al., Intramuscular administration of AAV1-lipoprotein lipase S447X lowers triglycerides in lipoprotein lipase-deficient patients. Arterioscler Thromb Vasc Biol. Dec. 2008;28(12):2303-4. Supplementary Tables and Figures 8 pages.
Vigna et al., Lentiviral vectors: excellent tools for experimental gene transfer and promising candidates for gene therapy. J Gene Med. Sep.-Oct. 2000;2(5):308-16.
Walther et al., Viral vectors for gene transfer: A review of their use in the treatment of human diseases. Drugs. Aug. 2000;60(2):249-71.
Wang et al., A regulatory system for new use in gene transfer. Proc. Natl. Acad. Sci. USA. 1994;91:8180-4.
Williams et al., The role of the Wnt family of secreted proteins in rat oval "stem" cell-based liver regeneration: Wnt1 drives differentiation. Am J Pathol. Jun. 2010;176(6):2732-42. Epub Apr. 22, 2010.
Willis, RNA polymerase III. Genes, factors and transcriptional specificity. Eur J Biochem. Feb. 1993 15;212(1):1-11.
Zhu et al., Chemical strategies for stem cell biology and regenerative medicine. Annu Rev Biomed Eng. Aug. 15, 2011;13:73-90.
Zilberberg et al., A rapid and sensitive bioassay to measure bone morphogenetic protein activity. BMC Cell Biol. Sep. 19, 2007;8:41.
Zong et al., Notch signaling controls liver development by regulating biliary differentiation. Development. May 2009;136(10):1727-39. doi: 10.1242/dev.029140. Epub Apr. 15, 2009.
Barker et al., Identification of stem cells in small intestine and colon by marker gene Lgr5. Nature. Oct. 25, 2007;449(7165):1003-7. Epub Oct. 14, 2007.
Hodin et al., Immediate-early gene expression in EGF-stimulated intestinal epithelial cells. J Surg Res. Jun. 1994;56(6):500-4.
Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.
Nasonkin et al., Nonhuman sialic acid Neu5Gc is very low in human embryonic stem cell-derived neural precursors differentiated with B27/N2 and noggin: implications for transplantation. Exp Neurol. Oct. 2006;201(2):525-9.
Ootani et al., Sustained in vitro intestinal epithelial culture within a Wnt-dependent stem cell niche. Nat Med. Jun. 2009;15(6):701-6. Supplementary Information 16 pages.
Segev et al., Differentiation of human embryonic stem cells into insulin-producing clusters. Stem Cells. 2004;22(3):265-74.
Touhami et al., The role of NGF signaling in human limbal epithelium expanded by amniotic membrane culture. Invest Ophthalmol Vis Sci. Apr. 2002;43(4):987-94.
Petersen et al., Interaction with basement membrane serves to rapidly distinguish growth and differentiation pattern of normal and malignant human breast epithelial cells. Proc Natl Acad Sci U S A. Oct. 1, 1992;89(19):9064-8.

* cited by examiner

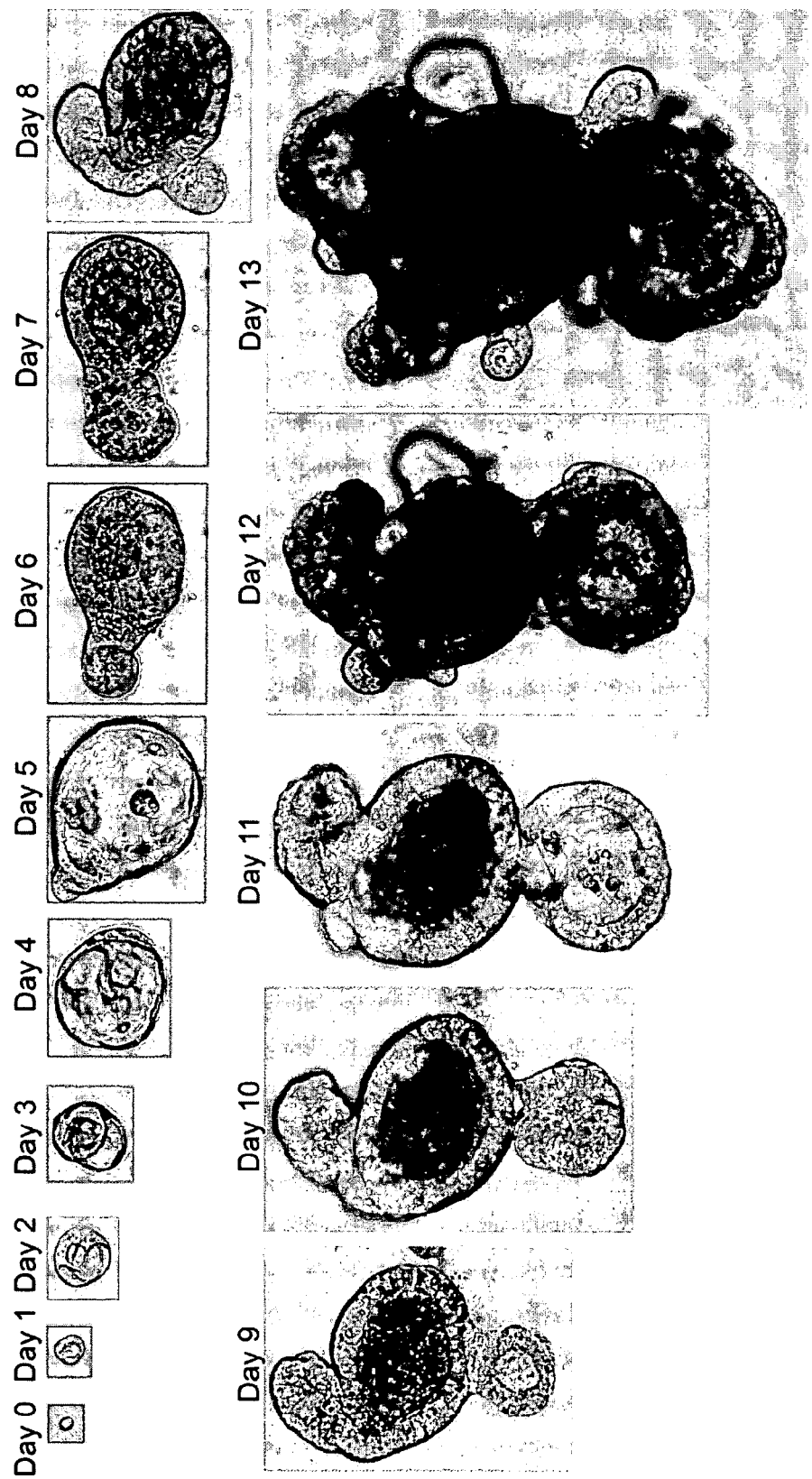

Freshly isolated colon crypts

Colon crypt organoid Day 4

Colon crypt organoid Day 14

| Control | Zinc chelator |
|---|---|
|  |  |

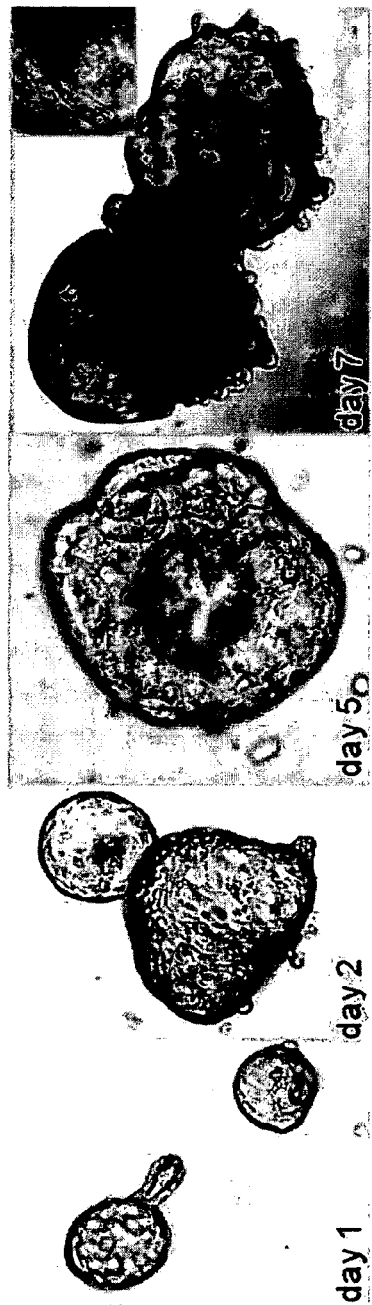
Fig 22a
Fig 22b

Pancreatic duct organoid with islet like structures (arrows)
Day 21

Islet like structure (high magnification)

Pancreatic islet-like structure

Days after transfer to DM

Day

0

1

3

5

7

10
Passage 1

SEQUENCE LISTING

<160> NUMBER OF SEQ ID NOS: 45

<210> SEQ ID NO 1
<211> LENGTH: 17
<212> TYPE: PRT
<213> ORGANISM: H. sapiens

<400> SEQUENCE: 1

Cys Asp Asp Tyr Tyr Tyr Gly Phe Gly Cys Asn Lys Phe Cys Arg Pro
1               5                   10                  15

Arg

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tattgtatct accgtgaatc ttgg                                      24

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
cagttgtccg tggctctc                                             18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tccaacctca gcgtcttc                                             18

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
tgggaatgtg tgtcaaag                                             18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aagtttgttg ttggatatgc                                           20

<210> SEQ ID NO 7
<211> LENGTH: 21

<212> TYPE: DNA
<213> ORGANISM: Artificial Sequence
<220> FEATURE:
<223> OTHER INFORMATION: Primer

<400> SEQUENCE: 7
catcttaggc tttgtatttg g                                              21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tcctcggagc ttttctacga                                                20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgtgtctctg gggacacttg                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aacaacctgc ctatgcaacc                                                20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acttggacgg gaactgacac                                                20

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
aagatcattg gcggaaag                                                  18

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gagtgctcag gatgttaag                                                 19

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gctgacagca gagaagcggc t                                              21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gacaggctct ctagctcctg g                                              21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aagttggaag aggaagtcag                                                20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
agaccttctg ctcagtcg                                                  18

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tttgtcaagc agcacctttg                                                20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tctacaatgc cacgcttctg                                                20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gaggcaagga agatgctgtc                                               20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gggcatcatt ctctgtctgg                                               20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ttactttgtg gctggattgc tt                                            22

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
agtggcgttt gtcttcattc a                                             21

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ggaaatgctt tgacacacat tc                                            22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
ggaagtcatc aaggttatta taa                                           23

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tgaatcctcg gccttctatg                                               20

<210> SEQ ID NO 27
<211> LENGTH: 22

```
<212> TYPE: DNA
<213> ORGANISM: Artificial Sequence
<220> FEATURE:
<223> OTHER INFORMATION: Primer

<400> SEQUENCE: 27
cagttaaagt tggtggcact tc                                              22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ccaacctgtg ggtgtcttct                                                 20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ttagggacct ggatgctttg                                                 20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgcatgctca atggtatggt                                                 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgtgggctct ggagaagagt                                                 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ccatgaagtg ggagtgtgtg                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33 tgggatagc atccttccag                                                  20
```

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
gcccagcaga gaaaggaatc ca                                              22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gcgcctcttt gacctcttcc                                                 20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gccaactatt ccccagctct                                                 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ggctctggaa gagtgttgct                                                 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gaggcaagga agatgctgtc                                                 20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gggcatcatt ctctgtctgg                                                 20

<210> SEQ ID NO 40
<211> LENGTH: 20
<212> TYPE: DNA
<213> ORGANISM: Artificial Sequence
<220> FEATURE:
<223> OTHER INFORMATION: Primer

```
<400> SEQUENCE: 40
gaacggggcc atggtcagca                                            20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
cataattggt cttgcatgcc                                            20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
cttgctgcag acgctcaac                                             19

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
tctgtgtaca ccacccggta                                            20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
aagcttgctg gtgaaaagga                                            20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ttgcgctcat cttaggcttt                                            20
```

CULTURE MEDIUM FOR EPITHELIAL STEM CELLS AND ORGANOIDS COMPRISING THE STEM CELLS

CROSS-REFERENCE TO RELATED APPLICATIONS

This application is the national stage under 35 U.S.C. §371 of International Application Number PCT/NL2010/000017, filed Feb. 3, 2010, designating the United States of America, and published, in English, on Aug. 12, 2010 as WO 2010/090513 A2, which claims priority under 35 U.S.C. §119(e) to U.S. provisional patent application Ser. No. 61/149,622, filed Feb. 3, 2009, and further claims priority under Article 8 of the PCT to EP 09151970.2, filed Feb. 3, 2009, and EP 09171831.2, filed Sep. 30, 2009.

TECHNICAL FIELD

The invention relates to a novel culture medium for culturing epithelial stem cells, especially intestinal and colonic epithelial stem cells, and for culturing organoids comprising the stem cells. The invention further relates to the progeny of cells and organoids that were cultured using a culture medium of the invention, and to the use of the progeny in toxicity assays or in regenerative medicine.

BACKGROUND

The self-renewing epithelium of the small intestine is ordered into crypts and villi (Gregorieff and Clevers, 2005, *Genes Dev.* 19:877-90). Cells are newly generated in the crypts and are lost by apoptosis at the tips of the villi, with a resulting epithelial turn-over time of five days in the mouse. Self-renewing stem cells have long been known to reside near the crypt bottom and to produce the rapidly proliferating transit amplifying (TA) cells capable of differentiating towards all lineages. The estimated number of stem cells is between four and six per crypt (Bjerknes and Cheng, 1999, *Gastroenterology* 116:7-14). Three differentiated cell types, enterocytes, goblet cells and enteroendocrine cells, form from TA cells and continue their migration in coherent bands along the crypt-villus axis. Each villus receives cells from multiple different crypts. The fourth major differentiated cell-type, the Paneth cell, resides at the crypt bottom.

A gene, Lgr5, was recently identified, which is specifically expressed in a fifth cell type, cycling Crypt Base Columnar (CBC) cells, which are small cells that are interspersed between the Paneth cells (indicated by black arrows in FIG. 8, Panel b) (Barker et al., 2007, *Nature* 449:1003-1007). Using a mouse in which a GFP/tamoxifen-inducible Cre recombinase cassette was integrated into the Lgr5 locus, it was shown by lineage tracing that the Lgr5+ CBC cells constitute multipotent stem cells, which generate all cell types of the epithelium even when assessed 14 months after Cre induction.

It was recently discovered that Lgr6, besides Lgr5, but not Lgr4, is also a unique marker for adult stem cells. While Lgr5 is expressed in stem cells of brain, kidney, liver, retina, stomach, intestine, pancreas, breast, hair follicle, ovary, adrenal medulla, and skin, Lgr6 is expressed in stem cells of brain, lung, breast, hair follicle, and skin.

It is generally believed that an intimate contact between epithelial stem cells and subepithelial fibroblasts is required to anchor and support epithelial stem cells and to provide the correct orientation necessary to generate a properly polarized, three-dimensional structure.

Although a variety of culture systems have been described for culturing primary epithelial stem cells, including intestinal epithelium stem cells (Bjerknes and Cheng, 2006, *Methods Enzymol.* 337-83), to date, no long-term culture system has been established that maintains the pluripotency of epithelial stem cells. Furthermore, no culture system is known that preserves the basic crypt-villus physiology of crypts that have been isolated from colon or intestine, or that preserves the basic physiology of isolated pancreatic fragments or gastric tissue fragments.

DISCLOSURE

The invention, therefore, provides a method for culturing epithelial stem cells, isolated epithelial tissue fragments comprising the epithelial stem cells, or adenoma cells, the method comprising providing an extracellular matrix, incubating an epithelial stem cell, an isolated tissue fragment comprising the epithelial stem cells, or an adenoma cell with the extracellular matrix, culturing the stem cell, isolated tissue fragment, or adenoma cell in the presence of a cell culture medium, comprising a basal medium for animal or human cells to which is added a Bone Morphogenetic Protein (BMP) inhibitor, between 5 and 500 ngram/ml or at least 5 and not higher than 500 ngram/ml of a mitogenic growth factor, whereby a Wnt agonist is added if epithelial stem cells and isolated tissue fragments are cultured.

Surprisingly, it was found by the present inventors that a method of the invention allows culturing of epithelial stem cells, isolated fragments from the small intestine, colon, stomach and pancreas comprising the stem cells and adenoma cells, while preserving the presence of stem cells that retain an undifferentiated phenotype and self-maintenance capabilities. For example, isolated crypts that are cultured according to a method of the invention develop into crypt-villus organoids, comprising a central lumen lined by a villus-like epithelium. The growth of isolated crypts was fuelled by stem cells that are present in the crypts. The resulting organoids undergo multiple crypt fission events. Even more surprising was the observation that a method of the invention allows the outgrowth of single, isolated epithelial stem cells into crypt-villus organoids in the absence of a stem cell niche. Isolated gastric fragments from the pyloric region of the stomach behaved as intestinal crypt organoids. The opened upper part of the unit was sealed and the lumen was filled with apoptotic cells. The newly formed gastric organoids underwent continuous budding events (reminiscent of gland fission) while maintaining their polarity with a central lumen. Furthermore, culturing pancreatic fragments resulted in the appearance of pancreatic islet-like structures that express insulin and other pancreatic islet-specific markers, resembling the pancreatic islets of Langerhans.

The epithelium lining the pyloric region of the small and large bowel encompasses luminal protrusions, villi, invaginations, and crypts. Each cell along the crypt-villus axis is polarized, whereby cells on the top of the intestinal villi, or in the upper positions of colonic crypts, are the most differentiated and are continuously lost into the lumen. Continuous proliferation of stem cells residing in the basis of the crypts, and massive proliferation of progenitor cells residing in the middle of the crypts, ensures proper replacement of the shed cells.

Stem cells are found in many organs of adult humans and mice. Although there may be great variation in the exact characteristics of adult stem cells in individual tissues, adult stem cells share the following characteristics: they retain an undifferentiated phenotype; their offspring can differentiate toward all lineages present in the pertinent tissue; they retain self-maintenance capabilities throughout life; and they are able to regenerate the pertinent tissue after injury. Stem cells reside in a specialized location, the stem cell niche, which supplies the appropriate cell-cell contacts and signals for maintenance of the stem cell population.

Epithelial stem cells are able to form the distinct cell types of which the epithelium is composed. Some epithelia, such as skin or intestine, show rapid cell turnover, indicating that the residing stem cells must be continuously proliferating. Other epithelia, such as the liver or pancreas, show a very slow turnover under normal conditions.

Crypts can be isolated from the duodenum, small and large intestine, including jejunum, ileum, and colon, and the pyloric region of the stomach by protocols that are known to the skilled person. For example, crypts can be isolated by incubation of isolated tissue with chelating agents that release cells from their calcium- and magnesium-dependent interactions with the basement membrane and stromal cell types. After washing the tissue, the epithelial cell layer is scraped from the submucosa with a glass slide and minced. This is followed by incubation in trypsin or, more preferred, EDTA and/or EGTA and separation of undigested tissue fragments and single cells from crypts using, for example, filtration and/or centrifugation steps. Other proteolytic enzymes, such as collagenase and/or dispase I, can be used instead of trypsin. Similar methods are used to isolate fragments of the pancreas and stomach.

Methods to isolate stem cells from epithelial tissue are known in the art. A preferred method is based on the fact that stem cells express Lgr5 and/or Lgr6 on their surface, which belong to the large G protein-coupled receptor (GPCR) superfamily. The Lgr subfamily is unique in carrying a large leucine-rich ectodomain important for ligand binding. Ligands for Lgr5 and Lgr6 are not yet described in the literature. A preferred method, therefore, comprises preparing a cell suspension from the epithelial tissue, contacting the cell suspension with an Lgr5 and/or Lgr6 binding compound, isolating the Lgr5 and/or Lgr6 binding compound, and isolating the stem cells from the binding compound. It is preferred that a single cell suspension comprising the epithelial stem cells is mechanically generated from the isolated crypts as it was found that at this stage, epithelial stem cells treated with trypsin yielded rather low survival rates.

Preferred Lgr5 and/or Lgr6 binding compounds comprises antibodies, such as monoclonal antibodies, that specifically recognize and bind to the extracellular domain of either Lgr5 or Lgr6, such as monoclonal antibodies including mouse and rat monoclonal antibodies. Using such an antibody, Lgr5 and/or Lgr6-expressing stem cells can be isolated, for example, with the aid of magnetic beads or through fluorescence-activated cell sorting, as is clear to a skilled person.

In a preferred method of the invention, epithelial stem cells are isolated from the crypts, gastric fragments or pancreatic fragments. For example, epithelial stem cells are isolated from crypts that are isolated from the bowel. Preferred epithelial stem cells are isolated from the small intestine, including duodenum, jejunum and ileum, pancreas or stomach.

Isolated stem cells are preferably cultured in a microenvironment that mimics, at least in part, a cellular niche in which the stem cells naturally reside. The cellular niche is mimicked by culturing the stem cells in the presence of biomaterials, such as matrices, scaffolds, and culture substrates that represent key regulatory signals controlling stem cell fate. The biomaterials comprise natural, semi-synthetic and synthetic biomaterials, and/or mixtures thereof A scaffold provides a two-dimensional or three-dimensional network. Suitable synthetic materials for the scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007, *Curr. Opin. Chem. Biol.* 11(4):381-387; Saha et al., 2008, *Biophysical Journal* 95:4426-4438; Little et al., 2008, *Chem. Rev.* 108: 1787-1796). As is known to a skilled person, the mechanical properties such as, for example, the elasticity of the scaffold influences proliferation, differentiation and migration of stem cells. A preferred scaffold comprises biodegradable (co)polymers that are replaced by naturally occurring components after transplantation in a subject, for example, to promote tissue regeneration and/or wound healing. It is furthermore preferred that the scaffold does not substantially induce an immunogenic response after transplantation in a subject. The scaffold is supplemented with natural, semi-synthetic or synthetic ligands, which provide the signals that are required for proliferation and/or differentiation, and/or migration of stem cells. In a preferred embodiment, the ligands comprise defined amino acid fragments. Examples of the synthetic polymers comprise PLURONIC® F127 block copolymer surfactant (BASF), and ETHISORB® (Johnson and Johnson).

A cellular niche is in part determined by the stem cells and surrounding cells, and the extracellular matrix (ECM) that is produced by the cells in the niche. In a preferred method of the invention, isolated crypts or epithelial stem cells are attached to an ECM. ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combinations of glycoproteins. The ECM can be provided by culturing ECM-producing cells, such as, for example, fibroblast cells, in a receptacle, prior to the removal of these cells and the addition of isolated crypts or epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (types I, III, and V), chondroitin sulfate proteoglycan, hyaluronic acid, fibronectin, and tenascin-C. Alternatively, the ECM is commercially provided. Examples of commercially available extracellular matrices are extracellular matrix proteins (Invitrogen) and Matrigel™ (BD Biosciences). The use of an ECM for culturing stem cells enhanced long-term survival of the stem cells and the continued presence of undifferentiated stem cells. In the absence of an ECM, stem cell cultures could not be cultured for longer periods and no continued presence of undifferentiated stem cells was observed. In addition, the presence of an ECM allowed culturing of three-dimensional tissue organoids, which could not be cultured in the absence of an ECM.

A preferred ECM for use in a method of the invention comprises at least two distinct glycoproteins, such as two different types of collagen or a collagen and laminin. The ECM can be a synthetic hydrogel extracellular matrix or a naturally occurring ECM. A most preferred ECM is provided by Matrigel™ (BD Biosciences), which comprises laminin, entactin, and collagen IV.

A cell culture medium that is used in a method of the invention comprises any cell culture medium. A preferred cell culture medium is a defined synthetic medium that is buffered at a pH of 7.4 (preferably between 7.2 and 7.6 or at least 7.2 and not higher than 7.6) with a carbonate-based buffer, while the cells are cultured in an atmosphere comprising between 5% and 10% $CO_2$, or at least 5% and not more than 10% $CO_2$, preferably 5% $CO_2$. A preferred cell culture medium is selected from DMEM/F12 and RPMI 1640 supplemented with glutamine, insulin, Penicillin/streptomycin and transferrin. In a further preferred embodiment, Advanced DMEM/F12 or Advanced RPMI is used, which is optimized for serum-free culture and already includes insulin. In this case, Advanced DMEM/F 12 or Advanced RPMI medium is preferably supplemented with glutamine and Penicillin/streptomycin. It is furthermore preferred that the cell culture medium is supplemented with a purified, natural, semi-synthetic and/or synthetic growth factor and does not comprise an undefined component such as fetal bovine serum or fetal calf serum. Supplements such as, for example, B27 (Invitrogen), N-Acetylcysteine (Sigma) and N2 (Invitrogen) stimulate proliferation of some cells and can further be added to the medium, if required.

A component that is added to the basal culture medium is a BMP inhibitor. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

"BMP inhibitor" is defined as an agent that binds to a BMP molecule to form a complex wherein the BMP activity is neutralized, for example, by preventing or inhibiting the binding of the BMP molecule to a BMP receptor. Alternatively, the inhibitor is an agent that acts as an antagonist or reverse agonist. This type of inhibitor binds with a BMP receptor and prevents binding of a BMP to the receptor. An example of a latter agent is an antibody that binds a BMP receptor and prevents binding of BMP to the antibody-bound receptor.

BMP inhibitor inhibits a BMP-dependent activity in a cell to at most 90%, more preferred at most 80%, more preferred at most 70%, more preferred at most 50%, more preferred at most 30%, more preferred at most 10%, more preferred 0%, relative to a level of a BMP activity in the absence of the inhibitor. As is known to a skilled person, a BMP activity can be determined by measuring the transcriptional activity of BMP, for example, as exemplified in Zilberberg et al., 2007, *BMC Cell Biol.* 8:41.

Several classes of natural BMP-binding proteins are known, including Noggin (Peprotech), Chordin and chordin-like proteins (R&D Systems) comprising chordin domains, Follistatin and follistatin-related proteins (R&D Systems) comprising a follistatin domain, DAN and DAN-like proteins (R&D Systems) comprising a DAN cysteine-knot domain, sclerostin/SOST (R&D Systems), decorin (R&D Systems), and alpha-2 macroglobulin (R&D Systems).

A preferred BMP inhibitor for use in a method of the invention is selected from Noggin, DAN, and DAN-like proteins including Cerberus and Gremlin (R&D Systems). These diffusible proteins are able to bind a BMP ligand with varying degrees of affinity and inhibit their access to signaling receptors. The addition of any of these BMP inhibitors to the basal culture medium prevents the loss of stem cells, which otherwise occurs after about two to three weeks of culture.

A most preferred BMP inhibitor is Noggin. Noggin is preferably added to the basal culture medium at a concentration of at least 10 ng/ml, more preferred at least 20 ng/ml, more preferred at least 50 ng/ml, more preferred at least 100 ng/ml. A most preferred concentration is approximately 100 ng/ml or 100 ng/ml. During culturing of stem cells, the BMP inhibitor is preferably added to the culture medium every second day, while the culture medium is refreshed preferably every fourth day.

A further component that is added to the basal culture medium is a Wnt agonist. The Wnt signaling pathway is defined by a series of events that occur when a Wnt protein binds to a cell-surface receptor of a Frizzled receptor family member. This results in the activation of Disheveled family proteins, which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined as an agent that activates TCF/LEF-mediated transcription in a cell. Wnt agonists are, therefore, selected from true Wnt agonists that bind and activate a Frizzled receptor family member including any and all of the Wnt family proteins, an inhibitor of intracellular β-catenin degradation, and activators of TCF/LEF. The Wnt agonist stimulates a Wnt activity in a cell by at least 10%, more preferred at least 20%, more preferred at least 30%, more preferred at least 50%, more preferred at least 70%, more preferred at least 90%, more preferred at least 100%, relative to a level of Wnt activity in the absence of the molecule. As is known to a skilled person, a Wnt activity can be determined by measuring the transcriptional activity of Wnt, for example, by pTOPFLASH and pFOPFLASH TCF luciferase reporter constructs (Korinek et al., 1997, *Science* 275:1784-1787).

A Wnt agonist comprises a secreted glycoprotein including Wnt-1/Int-1; Wnt-2/Irp (Int-1-related Protein); Wnt-2b/13; Wnt-3/Int-4; Wnt-3a (R&D Systems); Wnt-4; Wnt-5a; Wnt-5b; Wnt-6 (H. Kirikoshi et al., 2001, *Biochem. Biophys. Res. Com.* 283:798-805); Wnt-7a (R&D Systems); Wnt-7b; Wnt-8a/8d; Wnt-8b; Wnt-9a/14; Wnt-9b/14b/15; Wnt-10a; Wnt-10b/12; Wnt-11; and Wnt-16. An overview of human Wnt proteins is provided in "THE WNT FAMILY OF SECRETED PROTEINS," R&D Systems Catalog, 2004. Further Wnt agonists include the R-spondin family of secreted proteins, which is implicated in the activation and regulation of the Wnt signaling pathway and which is comprised of four members (R-spondin 1 (NU206, Nuvelo, San Carlos, Calif.), R-spondin 2 ((R&D Systems), R-spondin 3, and R-spondin-4); and Norrin (also called Norrie Disease Protein or NDP) (R&D Systems), which is a secreted regulatory protein that functions like a Wnt protein in that it binds with high affinity to the Frizzled-4 receptor and induces activation of the Wnt signaling pathway (Kestutis Planutis et al. (2007) *BMC Cell Biol.* 8:12). A small-molecule agonist of the Wnt signaling pathway, an aminopyrimidine derivative, was recently identified and is also expressly included as a Wnt agonist (Liu et al. (2005) *Angew Chem. Int. Ed. Engl.* 44:1987-90).

Known GSK-inhibitors comprise small-interfering RNAs (siRNA; Cell Signaling), lithium (Sigma), kenpaullone (Biomol International; M. Leost et al. (2000) *Eur. J. Biochem.* 267:5983-5994), 6-Bromoindirubin-30-acetoxime (L. Meijer et al. (2003) *Chem. Biol.* 10:1255-1266), SB 216763 and SB 415286 (Sigma-Aldrich), and FRAT-family members and FRAT-derived peptides that prevent interaction of GSK-3 with axin. An overview is provided by Meijer et al., (2004) *Trends in Pharmacological Sciences* 25:471-480, which is hereby incorporated by reference. Methods and assays for determining a level of GSK-3 inhibition are known to a skilled person and comprise, for example, the methods and assay as described in Liao et al. 2004, *Endocrinology* 145(6): 2941-9).

In a preferred embodiment, the Wnt agonist is selected from one or more of a Wnt family member, R-spondin 1-4, Norrin, and a GSK-inhibitor. It was found by the inventors that the addition of at least one Wnt agonist to the basal culture medium is essential for proliferation of the epithelial stem cells or isolated crypts.

In a further preferred embodiment, the Wnt agonist comprises or consists of R-spondin 1. R-spondin 1 is preferably added to the basal culture medium at a concentration of at least 50 ng/ml, more preferred at least 100 ng/ml, more preferred at least 200 ng/ml, more preferred at least 300 ng/ml, more preferred at least 500 ng/ml. A most preferred concentration of R-spondin 1 is approximately 500 ng/ml or 500 ng/ml. During culturing of stem cells, the Wnt family member is preferably added to the culture medium every second day, while the culture medium is refreshed preferably every fourth day.

In a preferred embodiment, a Wnt agonist is selected from the group consisting of R-spondin, Wnt-3a and Wnt-6. More preferably, R-spondin and Wnt-3a are both used as Wnt agonist. This combination is particularly preferred since this combination surprisingly has a synergetic effect on organoid formation. Preferred concentrations are approximately 500 ng/ml or 500 ng/ml for R-spondin and approximately 100 ng/ml or 100 ng/ml for Wnt-3a.

Yet a further component that is added to the basal culture medium is a mitogenic growth factor selected from a family of growth factors comprising epidermal growth factor (EGF; (Peprotech), Transforming Growth Factor-alpha (TGF-alpha; Peprotech), basic Fibroblast Growth Factor (bFGF; Peprotech), brain-derived neurotrophic factor (BDNF; R&D Systems), and Keratinocyte Growth Factor (KGF; Peprotech). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule, which is proteolytically cleaved to generate the 53-amino acid peptide hormone that stimulates cells. A preferred mitogenic growth factor is EGF. EGF is preferably added to the basal culture medium at a concentration of between 5 and 500 ng/ml or of at least 5 and not higher than 500 ng/ml. A preferred concentration is at least 10, 20, 25, 30, 40, 45, or 50 ng/ml and not higher than 500, 450, 400, 350, 300, 250, 200, 150, or 100 ng/ml. A more preferred concentration is at least 50 and not higher than 100 ng/ml. An even more preferred concentration is about 50 ng/ml or 50 ng/ml. The same concentrations could be used for a FGF, preferably for FGF 10 or FGF7. If more than one FGF is used, for example, FGF7 and FGF10, the concentration of a FGF is as defined above and refers to the total concentration of FGF used. During culturing of stem cells, the mitogenic growth factor is preferably added to the culture medium every second day, while the culture medium is refreshed preferably every fourth day. Any member of the bFGF family may be used. Preferably, FGF7 and/or FGF10 is used. FGF7 is also known as KGF (Keratinocyte Growth Factor).

In a further preferred embodiment, a combination of mitogenic growth factors such as, for example, EGF and KGF, or EGF and BDNF, is added to the basal culture medium. In a further preferred embodiment, a combination of mitogenic growth factors such as, for example, EGF and KGF, or EGF and FGF10, is added to the basal culture medium.

A further embodiment of a method according to the invention comprises a culture medium comprising a Rock (Rho-kinase) inhibitor. The addition of a Rock inhibitor was found to prevent anoikis, especially when culturing single stem cells. The Rock inhibitor is preferably selected from R)-(+)-trans-4-(1-aminoethyl)-N-(4-Pyridyl)cyclohexanecarboxamide dihydrochloride monohydrate (Y-27632; Sigma-Aldrich), 5-(1,4-diazepan-1-ylsulfonyl) isoquinoline (fasudil or HA 1077; Cayman Chemical), and (S)-(+)-2-methyl-1-[(4-methyl-5-isoquinolinyl)sulfonyl]-hexahydro-1H-1,4-diazepine dihydrochloride (H-1152; Tocris Bioscience). The Rho-kinase inhibitor, for example Y-27632, is preferably added to the culture medium every second day during the first seven days of culturing the stem cells. A preferred concentration for Y27632 is 10 µM.

In yet a further embodiment, a method according to the invention comprises a culture medium further comprising a Notch agonist. Notch signaling has been shown to play an important role in cell-fate determination, as well as in cell survival and proliferation. Notch receptor proteins can interact with a number of surface-bound or secreted ligands including, but not limited to, Delta 1, Jagged 1 and 2, and Delta-like 1, Delta-like 3, Delta-like 4. Upon ligand binding, Notch receptors are activated by serial cleavage events involving members of the ADAM protease family, as well as an intramembranous cleavage regulated by the gamma secretase presinilin. The resultant is a translocation of the intracellular domain of Notch to the nucleus where it transcriptionally activates downstream genes. A preferred Notch agonist is selected from Jagged 1 and Delta 1, or an active fragment or derivative thereof A most preferred Notch agonist is DSL peptide (Dontu et al., 2004, *Breast Cancer Res.* 6:R605-R615), with the sequence CDDYYYGFGCNKFCRPR (SEQ ID NO:1). DSL peptide (ANA spec) is preferably used at a concentration between 10 µM and 100 nM or at least 10 µM and not higher than 100 nM. The addition of a Notch agonist, especially during the first week of culturing, increases the culture efficiency by a factor of 2-3. The Notch agonist is preferably added to the culture medium every second day during the first seven days of culturing the stem cells.

A Notch agonist is defined as a molecule that stimulates a Notch activity in a cell by at least 10%, more preferred at least 20%, more preferred at least 30%, more preferred at least 50%, more preferred at least 70%, more preferred at least 90%, more preferred at least 100%, relative to a level of a Notch activity in the absence of the molecule. As is known to a skilled person, a Notch activity can be determined by measuring the transcriptional activity of Notch, for example, by a 4×wtCBF1-luciferase reporter construct as described (Hsieh et al., 1996, *Mol. Cell. Biol.* 16:952-959).

The invention further provides a cell culture medium comprising a basal medium for animal or human cells to which is added a Bone Morphogenetic Protein (BMP) inhibitor, a Wnt agonist; and between 5 and 500 nanogram/ml or at least 5 and not more than 500 nanogram/ml of a mitogenic growth factor selected from the group consisting of EGF, TGFα, KGF, FGF10 and a FGF. Preferably, a mitogenic factor is selected from the groups consisting of EGF, TGF-α and KGF or from EGF, TGF-α and FGF7 or from EGF, TGF-α and FGF or from EGF and KGF or from EGF and FGF7 or from EGF and a FGF or from TGFα and KGF or from TGFα and FGF7 or from TGFα and a FGF. EGF may be replaced by TGFα. Several preferred culture media are later on identified depending on the organoid to be obtained. A cell culture medium according to the invention allows the survival and/or proliferation and/or differentiation of epithelial stem cells or isolated crypts on an extracellular matrix. The term "cell culture medium" is synonymous with medium, culture medium or cell medium.

In a preferred method according to the invention, a first culture medium comprises Noggin as BMP inhibitor, both Epidermal Growth Factor and Keratinocyte Growth Factor as mitogenic growth factors, and R-spondin 1 as Wnt agonist, supplemented with B27, N2, and N-Acetylcysteine KGF could be replaced by a FGF, or by FGF10. [Leu15]-Gastrin I, Exendin and/or Nicotinamide may also be added to this first medium.

In another preferred embodiment, the culture medium, called a second culture medium, is identical as the first medium except that there is no Noggin and preferably no [Leu15]-Gastrin I, Exendin and/or Nicotinamide. The second culture medium, therefore, comprises both Epidermal Growth Factor and Keratinocyte Growth Factor as mitogenic growth factors, and R-spondin 1 as Wnt agonist, supplemented with B27, N2, and N-Acetylcysteine. KGF could also be replaced by a FGF, or by FGF10.

These two cell culture media support pancreatic fragments comprising pancreatic stem cells that are grown in these media in a Matrigel extracellular matrix to form pancreatic organoids comprising pancreatic islet-like structures on an extracellular matrix. The second medium without Noggin is a minimum medium, whereas the first one with Noggin leads to an improved medium for expanding pancreatic fragments. An expanding medium is a medium that preferably promotes survival and/or proliferation of cells during at least two days of culture.

A third medium has been designed that is able to promote or induce the differentiation of cells towards a pancreatic organoid within at least five days. One preferred differentiation marker towards the formation of a pancreatic organoid is Neurogenin-3, whose expression could be detected by RT-PCR or by immunohistochemistry. A differentiation medium such as, for example, a third or fourth medium is said to be functional when Neurogenin-3 can be detected by RT-PCR or by immunohistochemistry after at least five days of culture in the medium. This differentiation step is preferably carried out after a first expanding step in a medium as the first or second medium as defined above. This third medium is identical with the second medium identified above except that there is no FGF or KGF or FGF10. This third medium comprises Epidermal Growth Factor and R-spondin 1 as Wnt agonist, supplemented with B27, N2, and N-Acetylcysteine.

A fourth medium has been designed that is identical with the first medium, wherein the fourth medium is also supplemented with [Leu15]-Gastrin I and/or Exendin. The third medium is a minimal differentiation medium, whereas the fourth medium is an improved differentiation medium. A differentiation medium is a medium that preferably induces or promotes a specific differentiation of cells during at least five days of culture. In the case of a pancreatic organoid, differentiation may be measured by detecting the presence of a specific marker associated with the pancreatic lineage as defined earlier herein. Examples of other markers associated with the pancreatic lineage include: the secretion of insulin, which is detectable by RTPCR or immunohistochemistry after at least 7, 8, 9, or 10 days of culture in a differentiation medium.

Therefore, in a preferred method for obtaining and/or culturing a pancreatic organoid, epithelial stem cells, isolated tissue fragments comprising the epithelial stem cells or adenoma cells are cultured in a first step, either in the first or second medium, subsequently in a second step, either in the third or fourth medium. The first step may have a duration of at least two weeks and may be longer. A first step may be carried out for more than 1, 2, 3, 4, 5, 6, 7, 8, 9, or more than 10 months. The second step may have a duration of 8, 9, 10, 11, 12, 13, 14, 15, 16 days or longer. Each step is preferably carried out using an extracellular matrix as defined herein. Preferred concentrations of each compound present in each medium have already been defined herein in the description or in the examples. In a preferred embodiment, if a pancreatic organoid is to be used for regenerative medicine, one starts from epithelial cells or from an isolated pancreatic fragment. In another preferred embodiment, if a pancreatic organoid is to be used as a drug discovery system, one starts from adenoma. Accordingly, a pancreatic organoid obtainable by a method of the invention is a further aspect of the invention. Accordingly, in a further aspect, the invention provides a first, second, third, or fourth medium as defined herein.

To the best of our knowledge, this is the first time that a pancreatic organoid had been obtained that is functional and alive after at least ten months of culture (see experimental part). Functionality is preferably characterized by the secretion of insulin. Since the final amount of pancreatic organoids obtained correlates with the duration of culture, the skilled person understands that the invention is a pioneer invention and potentially opens new possibilities in, for example, regenerative medicine.

Accordingly, in a preferred method for obtaining and/or culturing a pancreatic organoid, epithelial stem cells, isolated tissue fragments comprising the epithelial stem cells or adenoma cells are cultured in contact with an extracellular matrix in a first step in a medium comprising EGF, KGF or FGF, and R-spondin 1 as Wnt agonist, supplemented with B27, N2, and N-Acetylcysteine, subsequently in a second step in a medium comprising EGF and R-spondin 1 as Wnt agonist, supplemented with B27, N2, and N-Acetylcysteine.

In a further preferred method according to the invention, a culture medium comprises Noggin as BMP inhibitor, Epidermal Growth Factor as mitogenic growth factor, R-spondin 1 and/or Wnt3a as Wnt agonist. This cell culture medium supports culturing of isolated small intestinal crypts in three-dimensional cultures comprising Matrigel as extracellular matrix.

In a further preferred method according to the invention, a culture medium comprises Noggin as BMP inhibitor, Epidermal Growth Factor as mitogenic growth factor, R-spondin 1 as Wnt agonist, Jagged-DSL peptide as Notch agonist and the Rho kinase inhibitor Y-27632. This cell culture medium supports culturing of isolated single epithelial stem cells in three-dimensional cultures comprising Matrigel as extracellular matrix.

In yet a further preferred method according to the invention, a culture medium comprises Noggin as BMP inhibitor, Epidermal Growth Factor and/or BDNF as mitogenic growth factors, R-spondin 1 and/or Wnt-3a as Wnt agonists, supplemented with at least one of B27, N2 and N-Acetylcysteine. Wnt-3a is a preferred Wnt agonist in this preferred method. This cell culture medium supports culturing of isolated colon crypts in three-dimensional cultures comprising Matrigel as extracellular matrix. This medium is able to promote survival and/or proliferation and/or differentiation of cells during at least two days of culture. A preferred differentiation marker towards the formation of a colon crypt may be selected from the following group: alkaline phosphatase indicating the presence of enterocyte, Muc2 indicating the presence of goblet cells and Neurogenic 3 or Chromogranin indicating the presence of endocrine cells. The expression of each of these markers could be detected by RTPCR or by immunohistochemistry. A medium functional for promoting survival and/or proliferation and/or differentiation of cells for obtaining a colon crypt is such that at least one of the identified markers could be detected after at least 2, 3, 4, 5, 6, 7, 8, 9, 10 days of culture or longer. A preferred medium comprises Noggin as BMP inhibitor, Epidermal Growth Factor as mitogenic growth factor, and R-spondin 1 and/or Wnt-3a as Wnt agonists, supplemented with at least one of B27, N2 and N-Acetylcysteine. This medium is called the fifth medium of the invention, which represents a further aspect of the invention.

Therefore, in a preferred method for obtaining and/or culturing a colon crypt, epithelial stem cells, isolated tissue fragments comprising the epithelial stem cells or adenoma cells are cultured in a medium as identified above, preferably the fifth medium. This method is preferably carried out using an extracellular matrix as defined herein. Preferred concentrations of each compound present in the medium have already been defined herein in the description or in the examples. Accordingly, a colon crypt obtainable by a method of the invention is a further aspect of the invention. To the best of our knowledge, this is the first time that a colon crypt had been obtained that is functional and alive after at least 1, 2, 3, 4, 5, 6, 7, 8, 9, 10, 11, or 12 months of culture (see experimental part). Functionality is preferably characterized by the presence of at least one of the markers as identified above. The invention is a pioneer invention and potentially opens new possibilities in, for example, regenerative medicine.

Accordingly, in a preferred method for obtaining and/or culturing a colon crypt, epithelial stem cells, isolated tissue fragments comprising the epithelial stem cells or adenoma cells are cultured in contact with an extracellular matrix in a medium comprising Noggin, EGF, and R-spondin 1 and/or Wnt-3 as Wnt agonist, supplemented with B27, N2, and N-Acetylcysteine.

In yet a further preferred method according to the invention, a culture medium comprises Noggin as BMP inhibitor, Epidermal Growth Factor as mitogenic growth factor, R-spondin 1 as Wnt agonist, supplemented with either Wnt-3a or KGF, and further comprising B27, N2, N-Acetylcysteine. This medium is called the sixth medium and accordingly represents a further aspect of the invention. KGF may be replaced by a FGF or by FGF10. This medium preferably comprises Noggin as BMP inhibitor, Epidermal Growth Factor and FGF10 as mitogenic growth factor, R-spondin 1 and Wnt-3a as Wnt agonist, and further comprising B27, N2, N-Acetylcysteine. FGF10 is preferred as a FGF since it gives better results than, for example, FGF7 (FIG. 32). This cell culture medium supports culturing of isolated gastric fragments or gastric organoid in three-dimensional cultures comprising Matrigel as extracellular matrix.

This sixth medium is a medium for expanding a gastric fragment. An expanding medium is a medium that preferably promotes survival and/or proliferation of cells during at least two days of culture. An additional medium, i.e., a seventh medium has been designed that is able to promote or induce the differentiation of cells towards a gastric organoid or gastric fragment within at least 2 days. This seventh medium is identical to the sixth medium identified above except that the concentration of Wnt-3a is reduced compared to the one present in the sixth medium. The concentration is reduced by at least 25%, 50%, 100%, 200%, 300%, 400%, 500%, 600% or more by comparison to the Wnt-3a concentration present in the sixth medium. This seventh medium comprises Epidermal Growth Factor and R-spondin 1 and Wnt-3a as Wnt agonist, Noggin and FGF10 supplemented with B27, N2, N-Acetylcysteine and Gastrin. Gastrin is preferably used at a concentration of 1 nM.

The seventh medium is a differentiation medium. A differentiation medium is a medium that preferably induces or promotes a specific differentiation of cells during at least 2, 3, 4, 5, 6, 7, 8, 9, 10 days of culture or longer. In the case of a gastric organoid or gastric fragment, differentiation may be measured by detecting the presence of a specific marker associated with the gastric lineage. Examples of markers associated with the gastric lineage include: MUC5AC (a pit cell marker), GASTRIN and/or SOMATOSTATIN (both, endocrine cell markers). The presence of at least one of the markers is preferably carried out using RT-PCR and/or immunohistochemistry or immunofluorescence. The presence of at least one of these markers is preferably detectable after at least six days in the differentiation conditions, more preferably at least ten days. A differentiation medium such as, for example, a seventh medium is said to be functional when at least one of the above-identified markers can be detected by RT-PCR or by immunohistochemistry after at least six days of culture in the medium. This differentiation step is preferably carried out after a first expanding step in a medium as the sixth medium as defined above.

Therefore, in a preferred method for obtaining and/or culturing a gastric fragment, epithelial stem cells isolated tissue fragments comprising the epithelial stem cells or adenoma cells are cultured in a first step, either in the sixth medium, subsequently in a second step, or in the seventh medium. Each step is preferably carried out using an extracellular matrix as defined herein. The first step may have a duration of at least three days and may be longer. A first step may be carried out for more than 3, 4, 5, 6, 7, 8, 9 days, or more. The second step may have a duration of 6, 7, 8, 9, 10, 11, 12, 13, 14, 15, 16 days or longer. Preferred concentrations of each compound present in each medium have already been defined herein in the description or in the examples. Accordingly, a gastric fragment obtainable by a method of the invention is a further aspect of the invention.

Accordingly, in a preferred method for obtaining and/or culturing a gastric fragment, epithelial stem cells, isolated tissue fragments comprising the epithelial stem cells or adenoma cells are cultured in contact with an extracellular matrix in a first step in a medium comprising Noggin as BMP inhibitor, Epidermal Growth Factor and FGF10 as mitogenic growth factor, R-spondin 1 and Wnt-3a as Wnt agonist, and further comprising B27, N2, N-Acetylcysteine, subsequently in a second step in a medium comprising Epidermal Growth Factor and R-spondin 1 and Wnt-3a as Wnt agonist, Noggin and FGF10 supplemented with B27, N2, and N-Acetylcysteine, wherein the concentration of Wnt-3 is reduced in the second step by comparison to the Wnt-3a concentration as present in the first step.

In yet a further preferred method according to the invention, a culture medium comprises Noggin as BMP inhibitor and Epidermal Growth Factor as mitogenic growth factor. This cell culture medium supports culturing of isolated adenoma fragments or isolated single adenoma cells in three-dimensional cultures comprising Matrigel as extracellular matrix.

A ligand, such as, for example, Wnt3a, can be freshly added to a culture medium. Alternatively, a ligand is expressed in a cell line by transfecting or infecting a cell line with a suitable expression construct expressing the ligand. The cell line is cultured and the culture medium comprising the secreted ligand is harvested at suitable time intervals. For example, cells will produce Wnt3a as soon as they reach confluency and stop growing. Culture medium from cells that were not transfected or infected with the expression construct is used as a control. The conditioned medium is harvested and tested, for example, in an assay, wherein luciferase expression in controlled by TCF-responsive elements to test for the presence of a Wnt agonist such as Wnt3a (Korinek et al., 1997, *Science* 275:1784-1787). The medium is diluted when used in the cultures to regenerate tissue. As is known to the skilled person, the addition of an excess of ligand sometimes is as detrimental for the culture as is the addition of too little ligand. Therefore, the actual dilution of the conditioned medium will depend on the amount of ligand that is determined in the test.

The invention further provides the use of a culture medium according to the invention for culturing epithelial stem cells or isolated organoid structures that comprise these stem cells on an extracellular matrix, whereby the stem cells preferably do not comprise human embryonic stem cells. Preferred are human adult stem cells. Furthermore, single sorted epithelial stem cells from the small intestine, colon, and stomach are also able to initiate these three-dimensional organoids in a culture medium according to the invention. The invention further provides the use of a culture medium according to the invention for culturing pancreatic fragments comprising stem cells that form pancreatic organoids comprising pancreatic island-like structures.

It is preferred that the stem cells are pancreas, stomach, intestinal or colonic epithelial stem cells, whereby most preferred stem cells are small intestinal stem cells. A culture medium according to the invention allowed the establishment of long-term culture conditions under which single crypts undergo multiple crypt fission events, while simultaneously generating villus-like epithelial domains in which all differentiated cell types are present. Using a culture method according to the invention allowed culture periods of at least seven months, at least eight months, at least nine months, and at least ten months.

Cultured crypts undergo dramatic morphological changes after taking them into culture. The upper opening of freshly isolated crypts becomes sealed and this region gradually balloons out and becomes filled with apoptotic cells, much like apoptotic cells are pinched off at the villus tip. The crypt region was found to undergo continuous budding events that create additional crypts, a process reminiscent of crypt fission. The crypt-like extensions comprise all differentiated epithelial cell types, including proliferative cells, Paneth cells, enterocytes and goblet cells. No myofibroblasts or other non-epithelial cells were identified in the organoids at any stage.

Expansion of the budding crypt structures created organoids, comprising >40 crypt-like structures surrounding a central lumen lined by a villus-like epithelium and filled with apoptotic cell bodies. The crypt-villus organoids comprise a central lumen lined by a villus-like epithelium. The lumen is opened at consecutive time intervals to release the content into the medium. The organoids can be passaged and maintained in culture for at least six months without losing the essential characteristics. Passaging preferably involves manual fragmentation of organoids.

A similar crypt-villus organoid structure is formed when single epithelial stem cells are cultured. After about one week, structures are formed that strongly resemble the crypt-villus organoid structures that are obtained with intact crypts. Histological analysis of these organoids also revealed the preservation of the basic crypt-villus architecture, the presence of all differentiated cell types, and the absence of non-epithelial elements.

In one aspect, the invention, therefore, provides crypt-villus organoids, comprising a central lumen lined by a villus-like epithelium that result from culturing of epithelial stem cells or isolated crypts in a culture medium of the invention. Preferably, the crypt-villus organoid is obtainable using a method of the invention.

In a further aspect, the invention provides pancreatic organoids generated or obtainable by culturing pancreatic fragments according to a method of the invention. Approximately 20% of the pancreatic organoids form a budding structure seven days after the start of the culture. The pancreatic ducts rapidly proliferate, in contrast to the acinar tissue, which only grows very slowly. After passaging of the pancreatic organoids, pancreatic islet-like structures that secrete insulin are observed that resemble the pancreatic islets of Langerhans that are present in healthy pancreatic tissue. The invention further provides a gastric organoid comprising a central lumen. Preferably, the gastric organoid is obtainable by a method of the invention.

Further growth factors that may be added to a culture medium, for example, to increase the presence of pancreatic islets in the organoids or to further support the culturing of isolated fragments such as gastric fragments, comprise cyclopamine (Sonic-hedgehog inhibitor; Tocris Bioscience), Activin, GLP (Glucagon-like peptide) and its derivative (Exendin 4; California Peptide Research), gastrin (Genscript), a Notch agonist (Jagged peptide, Ana Spec), Nicotinamide and a Wnt agonist such as Wnt-3a. Wnt-3a is preferably used when one starts culture with a single cell.

The invention further provides a collection of crypt-villus, gastric or pancreatic organoids, each comprising more than 10, preferably more than 20, more preferably more than 40 organoids. The crypt-villus organoids surround a central lumen lined by a villus-like epithelium. The lumen is filled with apoptotic cell bodies. The cells in the crypt-villus organoids are polarized, with stem cells residing in the basis of the structures. The top of the crypt-like structures comprise apoptotic cells that are shed into the lumen. The collection of crypt-villus organoids preferably comprises at least 10% viable cells, more preferred at least 20% viable cells, more preferred at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

In a further aspect, the invention provides the use of the crypt-villus organoids, gastric organoids or pancreatic organoids according to the invention in a drug discovery screen, toxicity assay or in regenerative medicine.

For high-throughput purposes, the crypt-villus, gastric or pancreatic organoids are cultured in multiwell plates such as, for example, 96-well plates or 384-well plates. Libraries of molecules are used to identify a molecule that affects the organoids. Preferred libraries comprise antibody fragment libraries, peptide phage display libraries, peptide libraries e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one or more genes in the progeny of the adenoma cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death. The crypt-villus, gastric or pancreatic organoids can also be used to identify drugs that specifically target epithelial carcinoma cells, but not the crypt-villus, gastric or pancreatic organoids.

The crypt-villus, gastric or pancreatic organoids can further replace the use of cell lines such as Caco-2 cells in toxicity assays of potential novel drugs or of known or novel food supplements.

Furthermore, the crypt-villus, gastric or pancreatic organoids can be used for culturing of a pathogen such as a norovirus, which presently lacks a suitable tissue culture or animal model.

Cultures comprising crypt-villus organoids are useful in regenerative medicine, for example, in post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further, use is present in the repair of the intestinal epithelium in patients with hereditary diseases of the small intestine/colon. Cultures comprising pancreatic organoids are also useful in regenerative medicine, for example, as implants after resection of the pancreas or part thereof and for treatment of diabetes such as diabetes I and diabetes II.

In an alternative embodiment, the expanded epithelial stem cells are reprogrammed into related tissue fates such as, for example, pancreatic cells including pancreatic β-cells, and liver cells. Thus far, it has not been possible to regenerate pancreatic cells or liver cells from adult stem cells. The culturing methods of the present invention will enable analysis for factors that trans-differentiate the closely related epithelial stem cell to a pancreatic cell, including a pancreatic β-cell, and a liver cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment.

In another aspect, the invention provides a method for culturing an epithelial adenoma cell, comprising providing an extracellular matrix, attaching an epithelial adenoma cell to the extracellular matrix, culturing the cell in the presence of a cell culture medium, comprising a basal medium for animal or human cells to which is added a Bone Morphogenetic Protein (BMP) inhibitor, and between 5 and 500 ngram/ml or at least 5 and not more than 500 ngram/ml of a mitogenic growth factor selected from EGF, TGF-alpha and KGF. KGF may be replaced by a FGF or FGF10.

An epithelial colon adenoma cell comprises an alteration in a gene coding for APC protein, which results in less efficient degradation of intracellular β-catenin by a complex of proteins comprising APC. Other mutations common in colon adenomas comprise mutations in β-catenin or Axin2. The overall result is enhanced TCF/LEF signaling because of an increased amount of fβ-catenin in the nucleus. A culture medium without a Wnt agonist was found to be sufficient for proliferation of adenoma cells.

The adenoma cell can be isolated from epithelial adenoma by methods known in the art, comprising the use of dissociating agents such as EDTA. Alternatively, single Lgr5- or Lgr-6-positive adenoma cells can be isolated from the adenoma by using a Lgr5-binding compound, followed by magnetic beads or FACS analyses.

The invention further provides progeny of an epithelial adenoma cell that was cultured in the presence of a cell culture medium, comprising a basal medium for animal or human cells to which is added a Bone Morphogenetic Protein (BMP) inhibitor and between 5 and 500 ngram/ml or at least 5 and not more than 500 ngram/ml of Epidermal Growth Factor (EGF). The cultured adenoma cells are not able to develop a polarized three-dimensional structure such as a crypt-villus-like architecture. Rather, adenoma cells form balloon-like structures in which cells are randomly oriented towards either the periphery or the central lumen. There is no sign of differentiation into other epithelial cell types. This result indicates a role for APC in the three-dimensional organization of the crypt-villus-like architecture.

In addition, the invention provides the use of the progeny of the adenoma cells for a targeted drug discovery screen to identify a drug that specifically affects adenoma cells compared to expanded normal epithelial cells that are cultured in the same culture medium. For high-throughput purposes, the progeny of adenoma cells is cultured in multiwell plates such as, for example, 96-well plates or 384-well plates. Libraries of molecules are used to identify a molecule that affects the progeny. Preferred libraries comprise antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. A compound that affects adenoma cells is subsequently, or in parallel, tested for affecting expanded normal epithelial cells. The term "affecting" is used to cover any change in a cell, including a reduction in, or loss of, proliferation, a morphological change, and cell death. The progeny can also be used to identify drugs that specifically target epithelial carcinoma cells, compared to epithelial adenoma cells, including reversion of the carcinoma cells.

It will be clear that the progeny can also be used in a high throughput approach for the determination of in vitro metabolic stability and metabolic profiles of drug candidates.

The invention furthermore provides the use of the progeny of adenoma cells according to the invention, of pancreatic organoids, of gastric organoids and of crypt-villus organoids of the invention, in toxicity assays. The progeny and crypt-villus organoids are easy to culture and more closely resemble primary epithelial cells than, for example, epithelial cell lines such as Caco-2 (ATCC HTB-37), 1-407 (ATCC CCL6), and XBF (ATCC CRL 8808), which are currently used in toxicity assays. It is anticipated that toxicity results obtained with primary adenoma cultures or with crypt-villus organoids more closely resemble results obtained in patients. A cell-based toxicity test is used for determining organ-specific cytotoxicity. Compounds that are tested in the test comprise cancer chemopreventive agents, environmental chemicals, food supplements, and potential toxicants. The cells are exposed to multiple concentrations of a test agent for a certain period of time. The concentration ranges for test agents in the assay are determined in a preliminary assay using an exposure of five days and log dilutions from the highest soluble concentration. At the end of the exposure period, the cultures are evaluated for inhibition of growth. Data are analyzed to determine the concentration that inhibited end point by 50 percent (TC50).

In this document and in its claims, the verb "to comprise" and its conjugations is used in its non-limiting sense to mean that items following the word are included, but items not specifically mentioned are not excluded. In addition the verb "to consist" may be replaced by "to consist essentially of," meaning that a product as defined herein may comprise additional component(s) than the ones specifically identified, the additional component(s) not altering the unique characteristic of the invention. In addition, a method as defined herein may comprise additional step(s) than the ones specifically identified, the additional step(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one." The word "about" or "approximately" when used in association with a numerical value (about 10) preferably means that the value may be the given value of 10 more or less 1% of the value.

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 9b: An example of a successfully growing single GFP$^{hi}$ cell. Panel c: Numbers of cells per single organoid averaged for five growing organoids. Panel d: Single cell suspension derived from a single-cell-derived-organoid was replated and grown for two weeks.

FIG. 17. Addition of Wnt3a increases the efficiency of organoid formation.

FIG. 22. Formation of gastric organoids in vitro (FIG. 22a) Isolated gastric glands growing into organoids. Differential interference contrast images from days 1, 2, 5 and 7 after seeding. Magnification 10× (days 1, 2, 5). Day 7 magnification 4×, inset 10×. (FIG. 22b) Cultures were passaged every four to seven days by mechanical dissociation. Cultures have been grown at least for one month. Representative images showing budding structures coming out from the organoids at different passages. Passage 1 (P1), passage 2 (P2) and passage 4 (P4) representing days 8, 11, 20, respectively.

FIG. 34. Single Lgr5+ve cells build long-lived gastric organoids in vitro.

DETAILED DESCRIPTION OF THE INVENTION

EXAMPLES

Example 1

Figure 1:
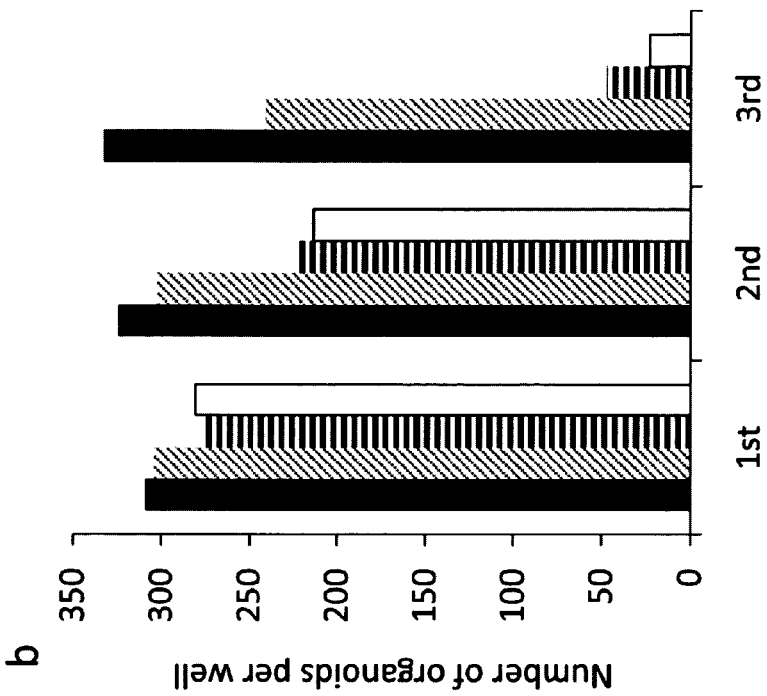
FIG. 1. Growth factor requirement of crypt culture. Panel a: 500 crypts were seeded with EGF (E; 0-50 ng/ml) and R-spondin 1 (R: 0-500 ng/ml) in triplicate; crypt organoids were counted seven days after seeding. Panel b: 500 Crypts/crypt organoids were cultured with EGF (50 ng/ml) and R-spondin 1 (500 ng/ml) with the indicated amounts of Noggin and followed for three passages. Crypt organoids were counted at each passage. The experiment was repeated three times with comparable results.
Figure 1:
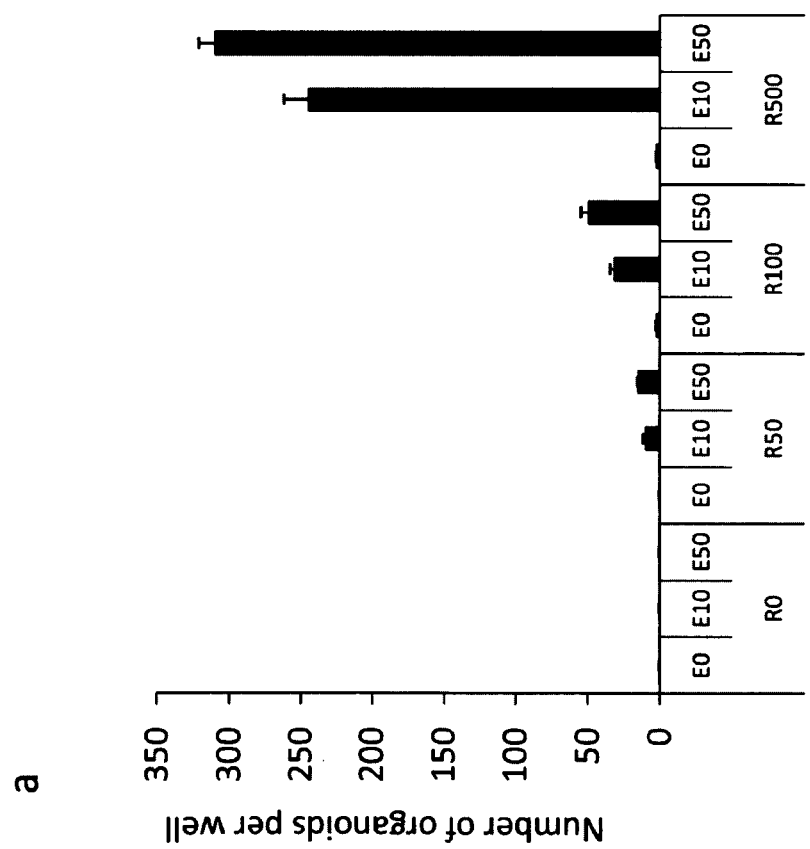

Culturing of Small Intestine Crypts and Villi In Vitro

Materials and Methods

Mice: Outbred mice of six to twelve weeks of age were used. Generation and genotyping of the Lgr5-EGFP-Ires-CreERT2 allele[1] has been previously described.[1] Rosa26-lacZ or YFP Cre reporter mice were obtained from Jackson Labs.

Crypt isolation, cell dissociation and culture: Crypts were released from murine small intestine by incubation in 2 mM EDTA/PBS for 30 minutes at 4° C. Isolated crypts were counted and pelleted. 500 crypts were mixed with 50 μl Matrigel (BD Bioscience) and plated in 24-well plates. After polymerization of Matrigel, 500 μl of crypt culture medium (Advanced DMEM/F12 with growth factors (10-50 ng/ml EGF (Peprotech), 500 ng/ml R-spondin 1[11] and 100 ng/ml Noggin (Peprotech)) was added. For sorting experiments, isolated crypts were incubated in culture medium for 45 minutes at 37° C., followed by resuspension with a glass pipette. Dissociated cells were passed through 20-μm cell strainer. $GFP^{hi}$, $GFP^{low}$ or $GFP^-$ cells were sorted by flow cytometry (MoFlo, Dako). Single viable epithelial cells were gated by forward scatter, side scatter and pulse-width parameter, and negative staining for propidium iodide. Sorted cells were collected in crypt culture medium and embedded in Matrigel including Jagged-1 peptide (Ana Spec, 1 µM) at 1 cell/well (in 96-well plate, 5 µl Matrigel). Crypt culture medium (250 µl for 48-well plate, 100 µl for 96-well plate) including Y-27632 (10 µM) was overlaid. Growth factors were added every other day and the entire medium was changed every four days. For passage, organoids were removed from Matrigel and mechanically dissociated into single-crypt domains, and transferred to new Matrigel. Passage was performed every one to two weeks with 1:5 split ratio.

Reagents: Murine recombinant EGF and Noggin were purchased from Peprotech. Human recombinant R-spondin 1,[11] Y-27632 (Sigma), 4-hydroxytamoxifen (Sigma) and Edu (Invitrogen) were used for culture experiments. The following antibodies were used for immunostaining: anti-lysozyme (Dako), anti-Synaptophysin (Dako), anti-BrdU (Roche), anti-β-catenin (BD Bioscience), anti-E-cadherin (BD Bioscience), anti-Smooth muscle actin (Sigma), anti-EphB2 and B3 (R&D), anti-villin, anti-Muc2, anti-chromogranin A (Santa Cruz), anti-caspase-3 (Cell Signaling).

Crypt Isolation: Isolated small intestines were opened longitudinally, and washed with cold PBS. The tissue was chopped into around 5 mm pieces, and further washed with cold PBS. The tissue fragments were incubated in 2 mM EDTA with PBS for 30 minutes on ice. After removal of EDTA medium, the tissue fragments were vigorously suspended by 10 ml pipette with cold PBS. The supernatant was the villous fraction and was discarded; the sediment was resuspended with PBS. After further vigorous suspension and centrifugation, the supernatant was enriched for crypts. This fraction was passed through a 70-µm cell strainer (BD bioscience) to remove residual villous material. Isolated crypts were centrifuged at 300 rpm for 3 minutes to separate crypts from single cells. The final fraction consisted of essentially pure crypts and was used for culture or single cell dissociation.

Tamoxifen induction and X-gal staining: To activate Cre-ERT2, crypts were incubated with low dose 4-hydroxytamoxifen (100 nM) for 12 hours and cultured in crypt culture medium. X-gal staining was performed as previously described.[1] No staining was seen without 4-hydroxytamoxifen treatment.

Electron microscopy analysis: As described previously,[1] Matrigel including crypt organoids were fixed in Karnovsky's fixative (2% paraformaldehyde, 2.5% glutaraldehyde, 0.1 M Na-cacodylate, 2.5 mM $CaCl_2$ and 5 mM $MgCl_2$, pH 7.4) for 5 hours at room temperature. The samples were embedded in Epon resin and were examined with a Phillips CM10 microscope (Eindhoven, The Netherlands).

Microarray analysis: Gene expression analysis of colonic crypts, small intestinal crypts and organoids. Freshly isolated small intestinal crypts from two mice were divided into two parts. RNA was directly isolated from one part (RNeasy Mini Kit, Qiagen), the other part was cultured for one week, followed by RNA isolation. We prepared labeled cRNA following the manufacturer's instruction (Agilent Technologies). Differentially labeled cRNA from small intestinal crypts and organoids were hybridized separately for the two mice on a 4×44k Agilent Whole Mouse Genome dual color Microarrays (G4122F) in two dye swap experiments, resulting in four individual arrays. Additionally, isolated colonic crypts were hybridized against differentially labeled small intestinal crypts in two dye swap experiments, resulting in four individual arrays. Microarray signal and background information were retrieved using Feature Extraction (V.9.5.3, Agilent Technologies). All data analyses were performed using ArrayAssist (5.5.1, Stratagene Inc.) and Microsoft Excel (Microsoft Corporation). Raw signal intensities were corrected by subtracting local background. Negative values were changed into a positive value close to zero (standard deviation of the local background) in order to allow calculation of ratios between intensities for features only present in one channel (small intestinal crypts or organoids) or (small intestinal crypts or colonic crypts). Normalization was performed by applying a Lowess algorithm and individual features were filtered if both (small intestinal crypts or organoids) or (small intestinal crypts or colonic crypts) intensities were changed or if both intensities were less than two times the background signal. Furthermore, non-uniform features were filtered. Data are available at GEO (Gene Expression Omnibus, number GSE14594) upon publication. Unsupervised hierarchical clustering was performed on normalized intensities (processed signal in Feature Extraction) of small intestinal/colonic crypts and organoids using Cluster 3 (distance: city block, correlation: average linkage) and visualized with TreeView. Genes were considered significantly changed if they were consistently in all arrays more than three-fold enriched in organoids or crypts.

Imaging analysis: The images of crypt organoids were taken with either confocal microscopy (Leica, SP5), inverted microscope (Nikon DM-IL) or stereomicroscope (Leica, MZ16-FA). For immunohistochemistry, samples were fixed with 4% paraformaldehyde (PFA) for 1 hour at room temperature, and Paraffin sections were processed with standard technique.[1] Immunohistochemistry was performed as previously described.[1] For whole-mount immunostaining, crypts organoids were isolated from matrigel using with Dispase (Invitrogen), and fixed with 4% PFA, following by permeabilization with 0.1% Triton-X. EdU staining was performed following the manufacturer's protocol (Click-IT, Invitrogen). DNA was stained by DAPI or ToPro-3 (Molecular Probe). Three-dimensional images were acquired with confocal microscopy (Leica, SP5) and reconstructed with Volocity Software (Improvision).

Results

The intestinal epithelium is the most rapidly self-renewing tissue in adult mammals. We have recently demonstrated the presence of approximately six cycling Lgr5+ stem cells at the bottoms of small intestinal crypts.[1] We have now established long-term culture conditions under which single crypts undergo multiple crypt fission events, while simultaneously generating villus-like epithelial domains in which all differentiated cell types are present. Single sorted Lgr5+ stem cells can also initiate these crypt-villus organoids. Tracing experiments indicate that the Lgr5+ stem cell hierarchy is maintained in organoids. We conclude that intestinal crypt-villus units are self-organizing structures, which can be built from a single stem cell in the absence of a non-epithelial cellular niche.

The self-renewing epithelium of the small intestine is ordered into crypts and villi.[2] Cells are newly generated in the crypts and are lost by apoptosis at the tips of the villi, with a turnover time of five days in the mouse. Self-renewing stem cells have long been known to reside near the crypt bottom and to produce the rapidly proliferating transit amplifying (TA) cells. The estimated number of stem cells is between four and six per crypt. Enterocytes, goblet cells and enteroendocrine cells develop from TA cells and continue their migration in coherent bands along the crypt-villus axis. The fourth major differentiated cell-type, the Paneth cell, resides at the crypt bottom. We have recently identified a gene, Lgr5, which is specifically expressed in cycling Crypt Base Columnar cells that are interspersed between the Paneth cells.[1] Using a mouse in which a GFP/tamoxifen-inducible Cre recombinase cassette was integrated into the Lgr5 locus, we showed by lineage tracing that the Lgr5+ cells constitute multipotent stem cells, which generate all cell types of the epithelium,[1] even when assessed 14 months after Cre induction.[3]

Although a variety of culture systems has been described,[4-7] no long-term culture system has been established that maintains basic crypt-villus physiology.[2]

Figure 2:
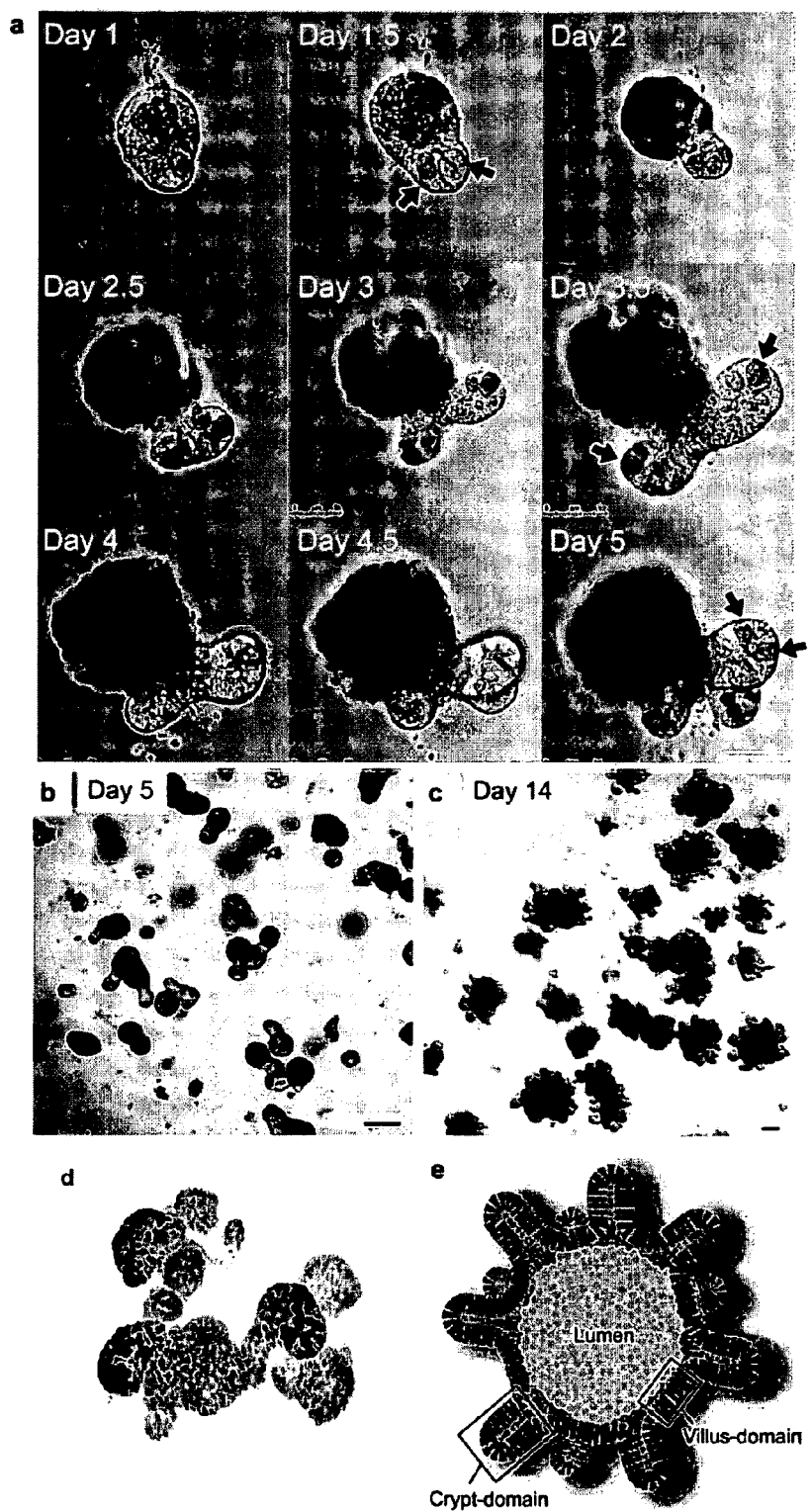
FIG. 2. Establishment of intestinal crypt culture system. Panel a: Time course of an isolated single crypt growing into an organoid. Differential interference contrast image reveals granule-containing Paneth cells at crypt bottoms (arrows). Panels b, c: Single isolated crypts efficiently faun crypt organoids. Through repeated crypt fission, the structures generate numerous octopus-like crypt organoids at day 14. Panel d: Three-dimensional reconstructed confocal image of a single organoid after a three-week culture. Lgr5-GFP$^+$ stem cells (light grey) are localized at the tip of crypt-like domains. Counterstaining for DNA: ToPro-3 (dark grey). Panel e: Schematic representation of a crypt organoid. The organoid consists of a central lumen lined by villus-like epithelium and a number of surrounding crypt-like domains. Dark grey cells at the tip of the crypt domain indicates the position of Lgr5$^+$ stem cells, which are present in each crypt domain. Scale bar indicates 50 μm.
Figure 3:
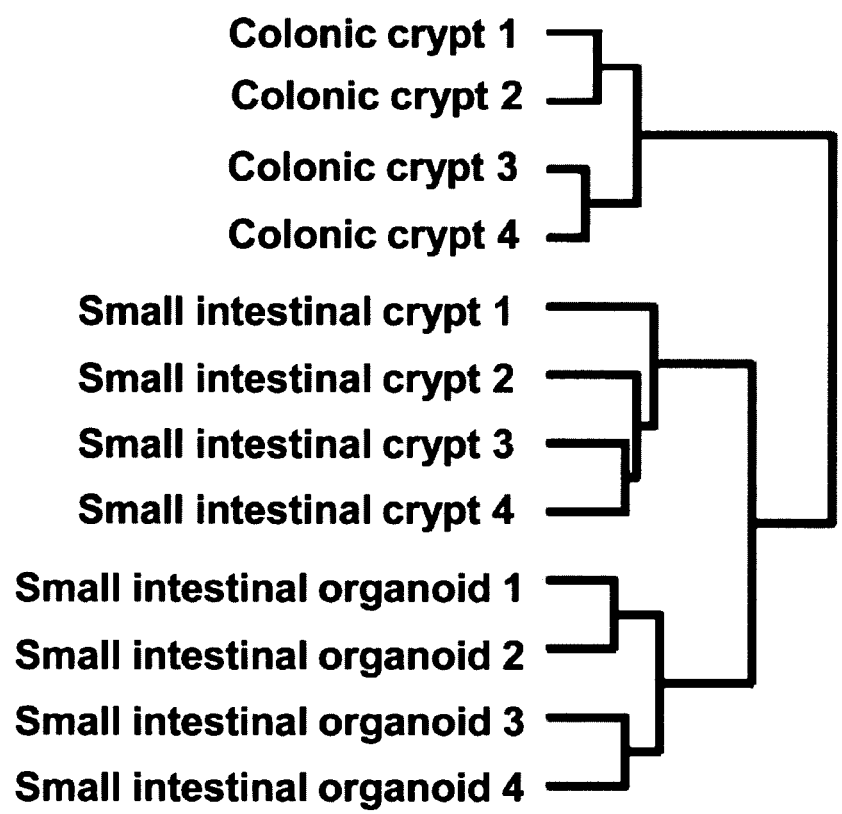
FIG. 3. Cluster analysis of gene-expression profiling. Cluster analysis of expression levels using freshly isolated colonic and small intestinal crypts as well as small intestinal organoids showed high degree of similarity between small intestinal organoids and the tissue they were derived from, small intestinal crypts. Colonic crypts clustered on a separate branch, indicating a different gene expression pattern of this closely related tissue. Of note, only 1.2% of all genes expressed were significantly enriched in organoids relative to small intestinal crypts, while, vice versa, 2% were enriched in small intestinal crypts. Ingenuity Pathway analysis on these differential genes revealed the specific presence of a lymphocyte signature in freshly isolated crypts, while no significant pathway could be identified in the small number of genes enriched in the organoids (not shown). We conclude that the latter group represents biological noise, while the lymphocyte signature derives from contaminating intraepithelial immune cells, lost upon culture.

Mouse crypt preparations were suspended in Matrigel. Crypt growth required EGF and R-spondin 1 (FIG. 1, Panel a). Passaging revealed a requirement for Noggin (FIG. 1, Panel b). The cultured crypts behaved in a stereotypical manner (FIG. 2, Panel a). The upper opening rapidly became sealed, and the lumen filled with apoptotic cells. The crypt region underwent continuous budding events, reminiscent of crypt fission.[17] Paneth cells were always present at the bud site. The majority of crypts could be cultured (FIG. 2, Panel b). Further expansion created organoids, comprising >40 crypt-domains surrounding a central lumen lined by a villus-like epithelium ("villus domain") (FIG. 2, Panels c-e). E-cadherin staining revealed a single cell layer (data not shown). Weekly, organoids were mechanically dissociated and replated at 1/5 of the pre-plating density. Organoids were cultured for >6 months without losing the characteristics described below. Expression analysis by microarray revealed that organoids remained highly similar to freshly isolated small intestinal crypts, when compared, for instance, to fresh colon crypts (FIG. 3).

Figure 4:
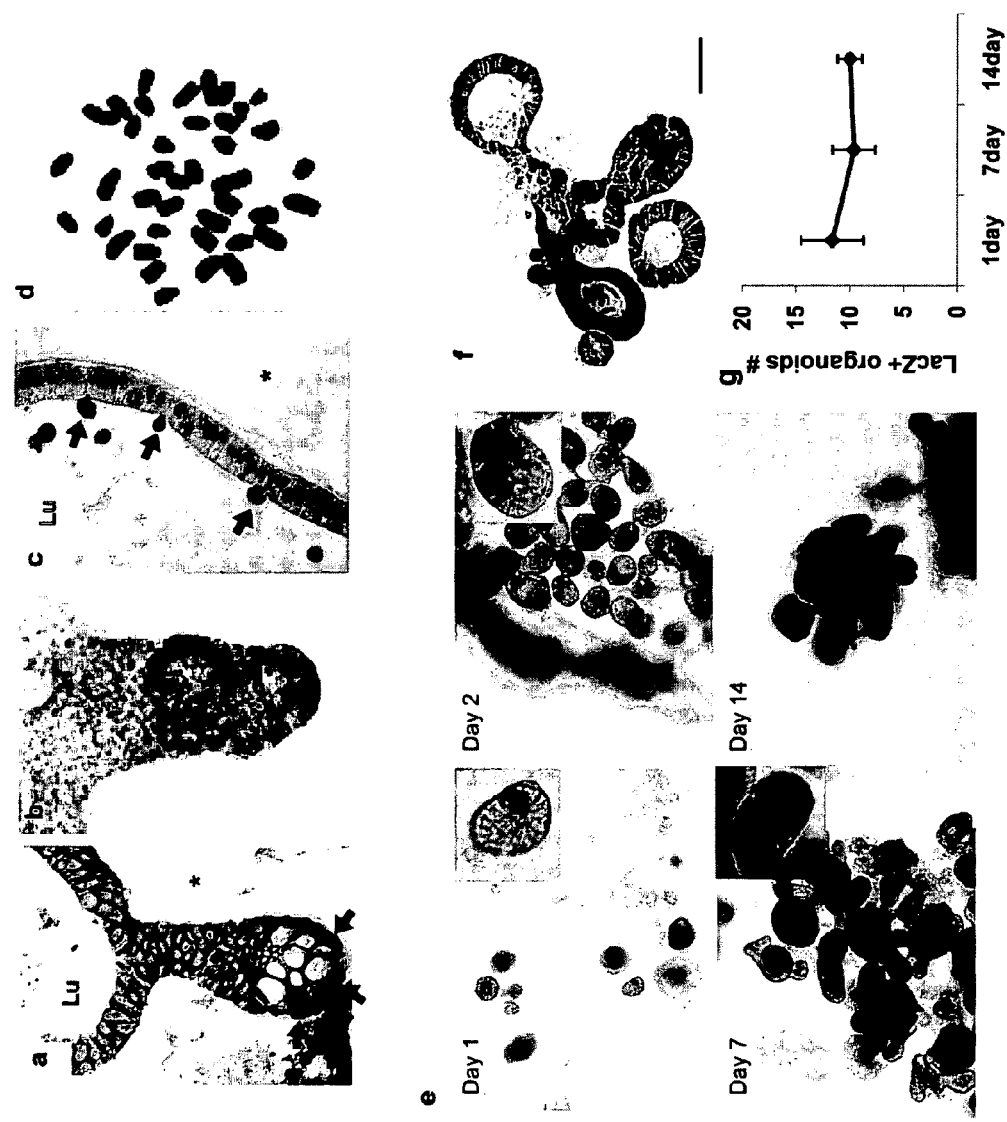
FIG. 4. Crypt organoids preserve basic crypt-villus characteristics. Panels a-e: The Wnt activation code is preserved in crypt domains. Panel a: Nuclear β-catenin (dark grey, arrows) was only seen in crypt domains. Higher resolution image in FIG. 5. Asterisk, matrigel; Lu, lumen. Panel b: EphB2 (light grey) is expressed in a gradient on CBC cells and TA cells. Note Lgr5-GFP$^+$ stem cells as indicated by white arrow. Panel c: Caspase-3$^+$ apoptotic cells (dark grey, arrows) shedding into the central lumen lined by enterocytes. Panel d: 40 chromosomes in a spread of cells from a >3 months old crypt culture. Panels e-g: Lineage tracing of Lg5$^+$ stem cells in vitro. Panel e: Crypts from Lgr5-EGFP-ires-CreERT2/Rosa26-lacZ reporter mice were stimulated by tamoxifen in vitro for 12 hours, and cultured for the indicated days. LacZ staining (dark grey) shows that scattered single LacZ$^+$ cells (day 1) generated entire LacZ$^+$ crypts in vitro (Days 2-14). Insets show higher magnification of stained crypt organoids. Panel f: Histological analysis shows an entire LacZ$^+$ crypt-domain (dark grey/black) feeds into the villus domain. Panel g: The percentage of crypt organoids with LacZ$^+$ cells remained steady over time, indicating that Lgr5$^+$ cells possess long-term stem cell activity. 500 crypts were seeded in triplicate, and LacZ$^+$ crypt organoids were counted. Error bars are standard deviation of triplicates. The experiment was repeated three times with similar results.
Figure 5B:
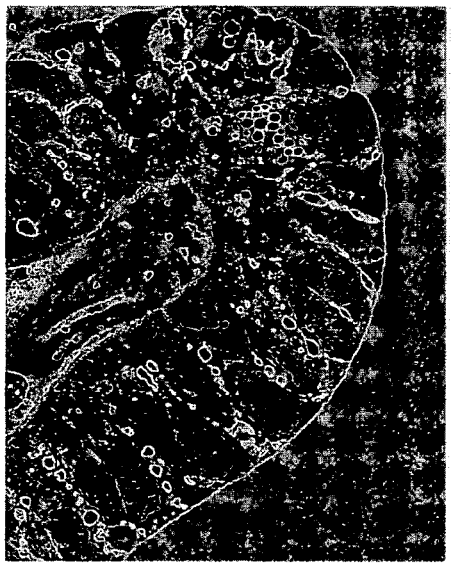
FIG. 5. Higher resolution image of FIG. 4, Panel a, and FIG. 11, Panels m and p.
Figure 5C:
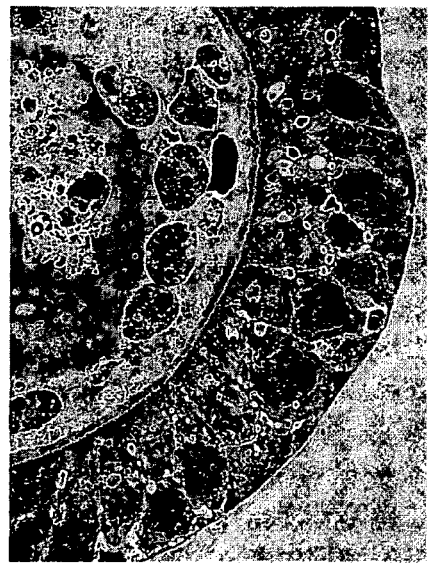
Figure 5A:
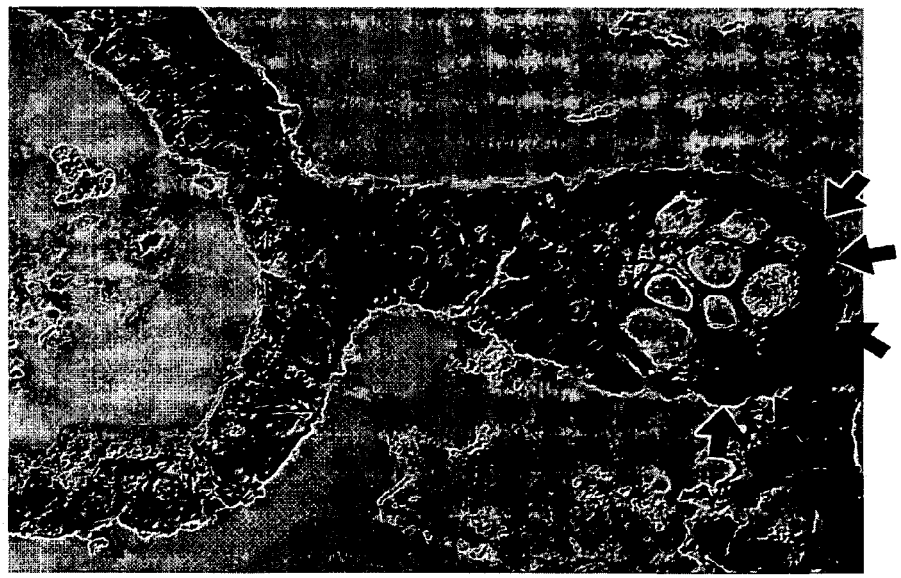
Figure 6:
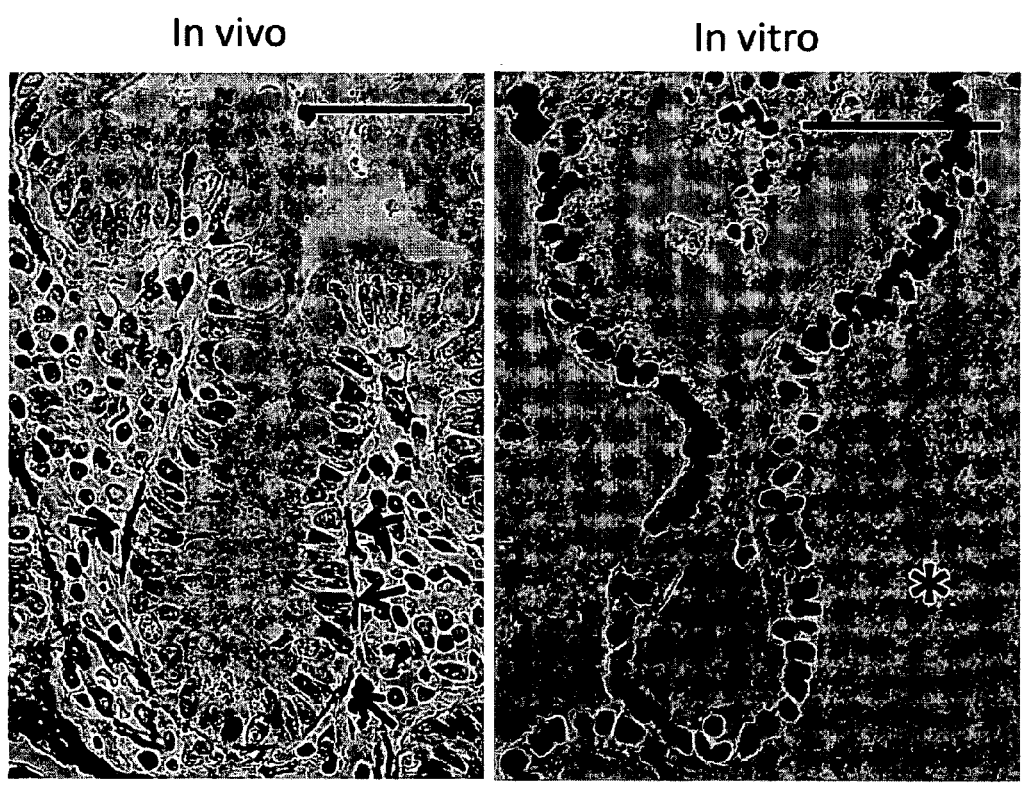
FIG. 6. No evidence of subepithelial fibroblasts in crypt organoids. Panel a: Immunostaining for smooth muscle actin (SMA; dark grey, examples indicated by black arrows) demonstrates the presence of subepithelial fibroblasts beneath the epithelial layer. Panel b: Absence of SMA+ cells in matrigel (asterisk) indicates the absence of subepithelial fibroblasts in the culture system. Scale bar; 50 μm.

Culture of Lgr5-EGFP-ires-CreERT2 crypts revealed Lgr5-GFP+ stem cells intermingled with Paneth cells at the crypt base. Wnt activation, as evidenced by nuclear β-catenin (FIG. 4, Panel a, FIG. 5) and expression of the Wnt target genes Lgr5 (FIG. 2, Panel d) and EphB2[18] (FIG. 4, Panel b) was confined to the crypts. Apoptotic cells were shed into the central lumen, a process reminiscent of the shedding of apoptotic cells at villus tips in vivo (FIG. 4, Panel c). Metaphase spreads of >3-month-old organoids consistently revealed 40 chromosomes/cell (n=20) (FIG. 4, Panel d). Surprisingly, we found no evidence for the presence of myofibroblasts or other non-epithelial cells (FIG. 6).

Figure 7:
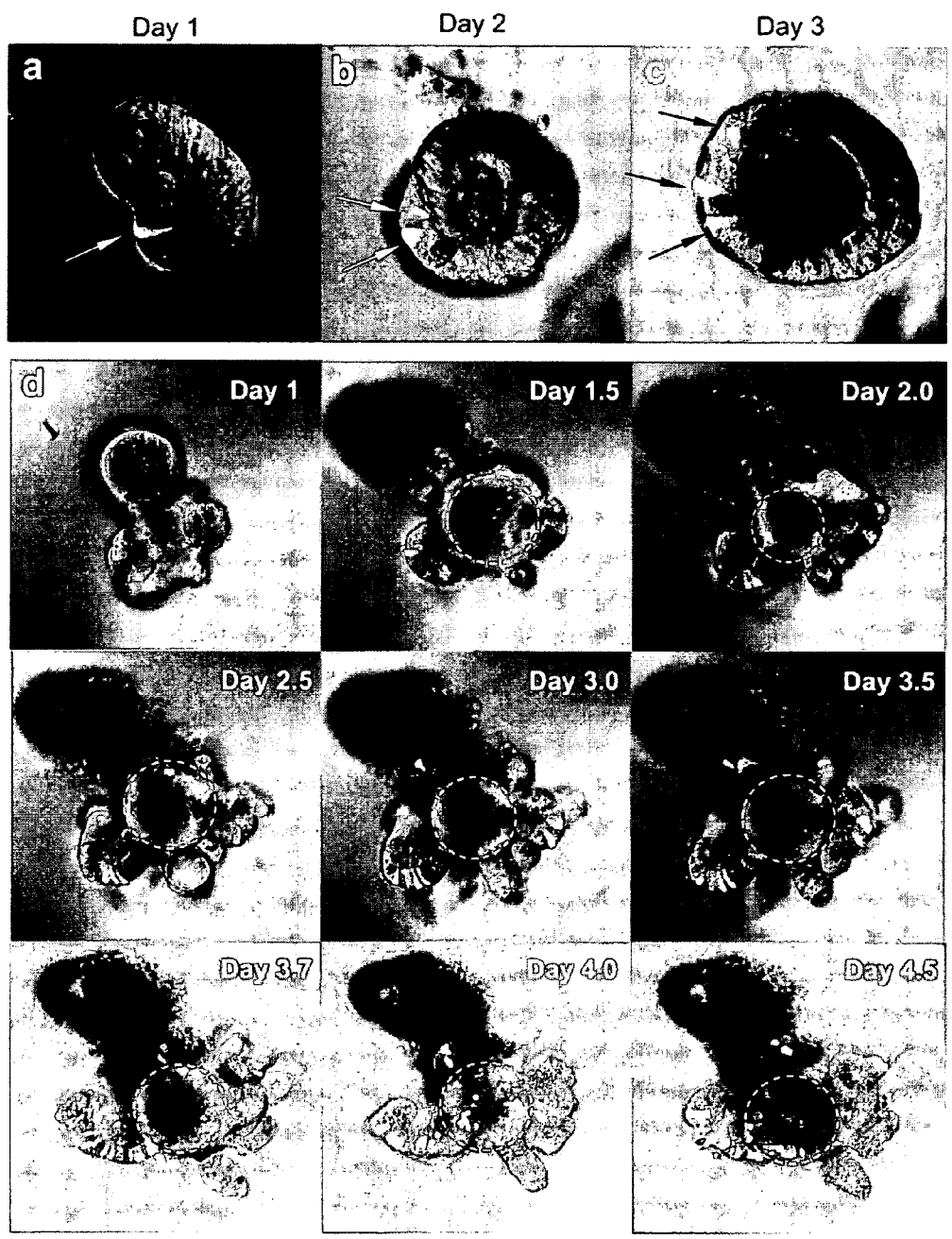
FIG. 7. Panels a-c: A crypt from an Lgr5-EGFP-ires-CreERT2/Rosa26-YFP reporter mouse was stimulated by tamoxifen in vitro for 12 hours, and imaged for the indicated days. Lgr5$^+$ cells are light grey and indicated by the white arrows. Panel d: Seven-day-old organoids derived from Lgr5-EGFP-ires-CreERT2/Rosa26-YFP crypts were stimulated by tamoxifen in vitro for 12 hours, and cultured and imaged for the indicated days. YFP fluorescence (light grey) shows that scattered single YFP$^+$ cells (day 1) generated multiple offspring in vitro over the next five days. The villus domain burst during Day 1-1.5, followed by new villus domain formation (white circle). Note that YFP+ cells are migrating toward villus domain.

We cultured crypts from Lgr5-EGFP-ires-CreERT2 mice crossed with the Cre-activatable Rosa26-LacZ reporter to allow lineage tracing. Directly after induction by low-dose tamoxifen, we noted single labeled cells (FIG. 4, Panels e, g). More than 90% of these generated entirely blue crypts (FIG. 4, Panels e-g), implying that the Lgr5-GFP+ cells indeed retained stem cell properties. Crypts from the Cre-activatable Rosa26-YFP reporter[19] mouse allowed lineage tracing by confocal analysis. Directly after tamoxifen treatment, we noted single labeled cells that induced lineage tracing over the following days, both in freshly isolated crypts (FIG. 7, Panels a-c) and in established organoids (FIG. 7, Panel d).

Figure 8:
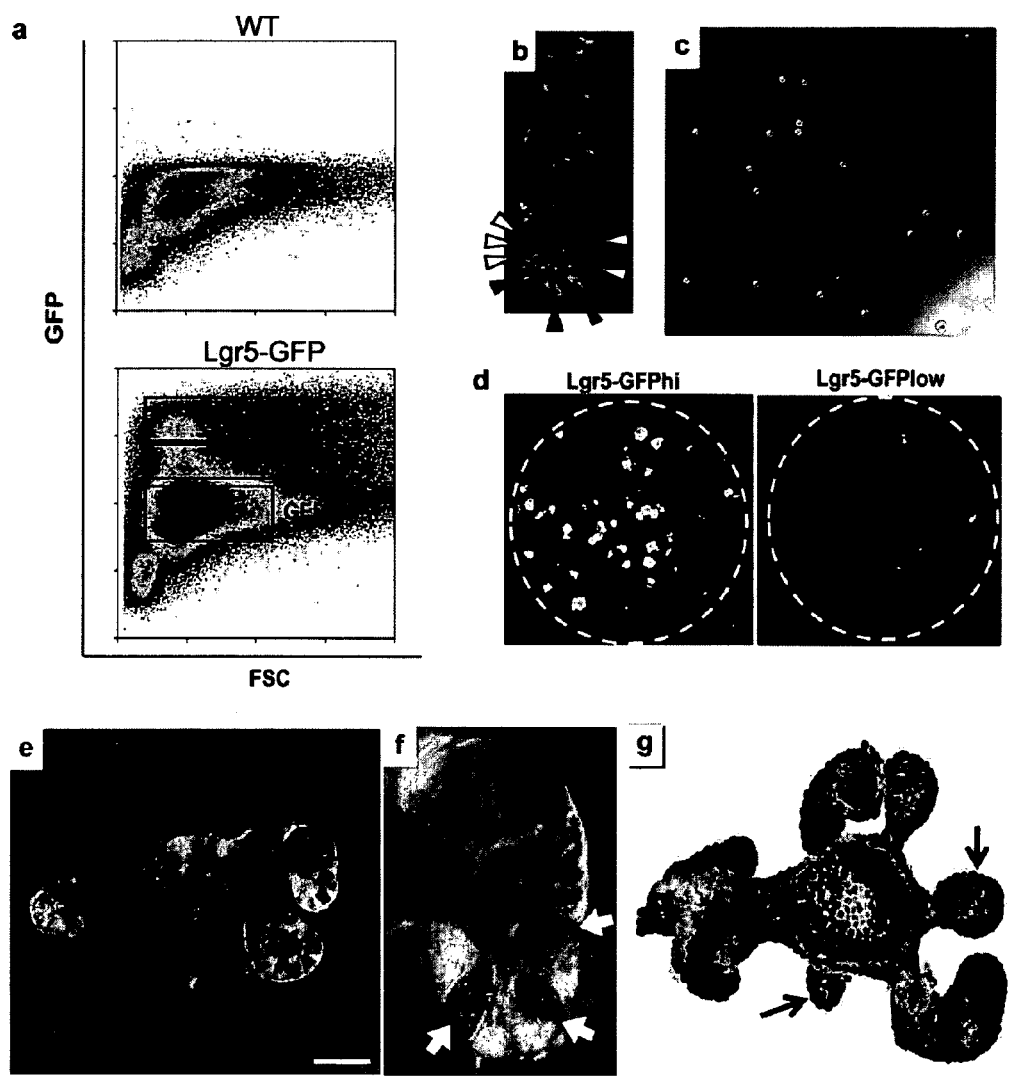
FIG. 8. Single sorted Lgr5$^+$ stem cells generate entire crypt-villus structures. Panel a: Lgr5-GFP$^+$ cells prepared from an Lgr5-EGFP-ires-CreERT2 intestine (bottom) compared to wild-type littermate (top). GFP$^+$ cells were divided into two populations; GFP$^{hi}$ and GFP$^{low}$. Panel b: Confocal microscopic analysis of a freshly isolated crypt shows GFP$^{hi}$ in CBC cells (black arrowheads) and GFP$^{low}$ above CBC (white arrowheads). Panel c: Sorted GFP$^{hi}$ cells. Panel d: 1000 sorted GFP$^{hi}$ cells (left) and GFP$^{low}$ cells (right) after a 14-day culture. Panels e-f: Fourteen days after sorting, single GFP$^{hi}$ cells form crypt organoids, with Lgr5-GFP$^+$ cells (light grey cells) and Paneth cells (white arrows) located at crypt bottoms. Scale bar; 50 µm. Panel f: Higher magnification of crypt bottom in Panel e. Panel g: To visualize proliferating cells, the organoids were cultured with the thymidine analog EdU (light grey, examples indicated by white arrows) for 1 hour, after which they were fixed. Note that only crypt domains incorporated EdU. Counterstain: DAPI (dark grey).

Recently, mammary gland epithelial structures were established from single stem cells in vitro.[21] When single Lgr5-GFP$^{hi}$ cells were sorted, these died immediately. The Rho kinase inhibitor Y-27632 significantly decreased this cell death. A Notch agonistic peptide[24] was found to support maintenance of proliferative crypts.[23] Under these conditions, significant numbers of L 5-GFP$^{hi}$ cells survived and formed large crypt organoids. Organoids formed rarely when GFP$^{low}$ daughter cells were seeded (FIG. 8, Panel d). Multiple Lgr5-GFP$^{hi}$ cells were intermingled with Paneth cells at crypt bottoms (FIG. 8, Panels e and f). EdU (thymidine analog) incorporation revealed S-phase cells in the crypts (FIG. 8, Panel g).

Figure 9:
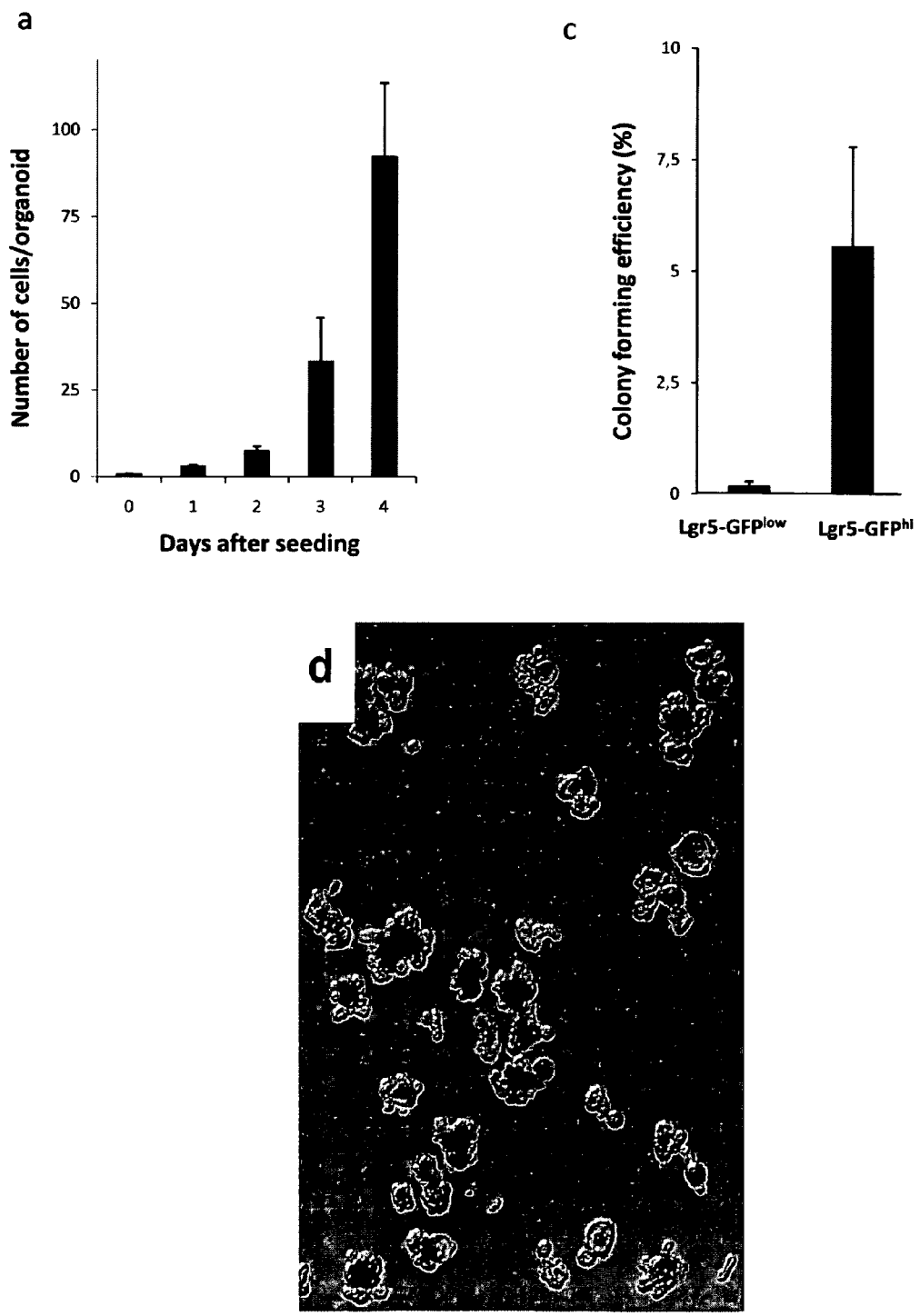
FIG. 9. Panel a: Colony-forming efficiency of single cells sorted in individual wells. The average is given for four individual experiments, of which, in each experiment, 100 cells were visually verified and then followed for growth.
Figure 10:
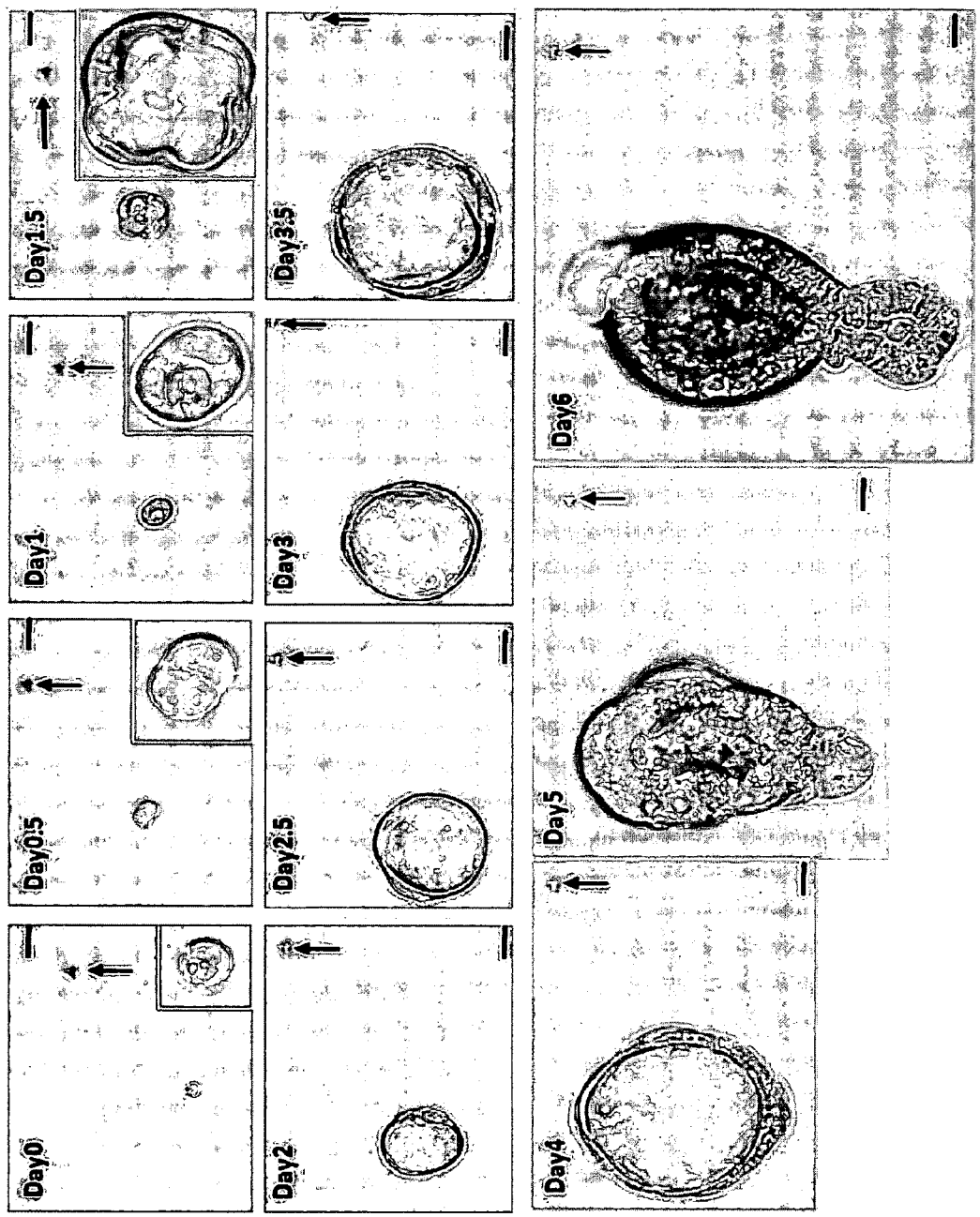
FIG. 10. Colony-forming potency of a single cell sorted in an individual well. An example of a successfully growing single GFP$^{hi}$ cell. The arrows point to a dust particle as a landmark. Scale bar: 50 µm.

We sorted cells at 1 cell/well, visually verified the presence of single cells and followed the resulting growth. In each of four individual experiments, we identified and followed 100 single cells. On average, approximately 6% of the Lgr5-GFP$^{hi}$ cells grew out into organoids, while the remaining cells typically died within the first 12 hours, presumably due to physical and/or biological stress inherent to the isolation procedure. GFP$^{low}$ cells rarely grew out (FIG. 9, Panel a). FIG. 9, Panel b and FIG. 10 illustrate the growth of an organoid from a single Lgr5-GFP$^{hi}$ cell. By four days of culture, the structures consisted of around 100 cells, consistent with the 12-hour cell cycle of proliferative crypt cells[25] (FIG. 9, Panel c). After two weeks, the organoids were dissociated into single cells and replated to form new organoids (FIG. 9, Panel d). This procedure could be repeated at least four times on a two-weekly basis, without apparent loss of replating efficiency.

Figure 11:
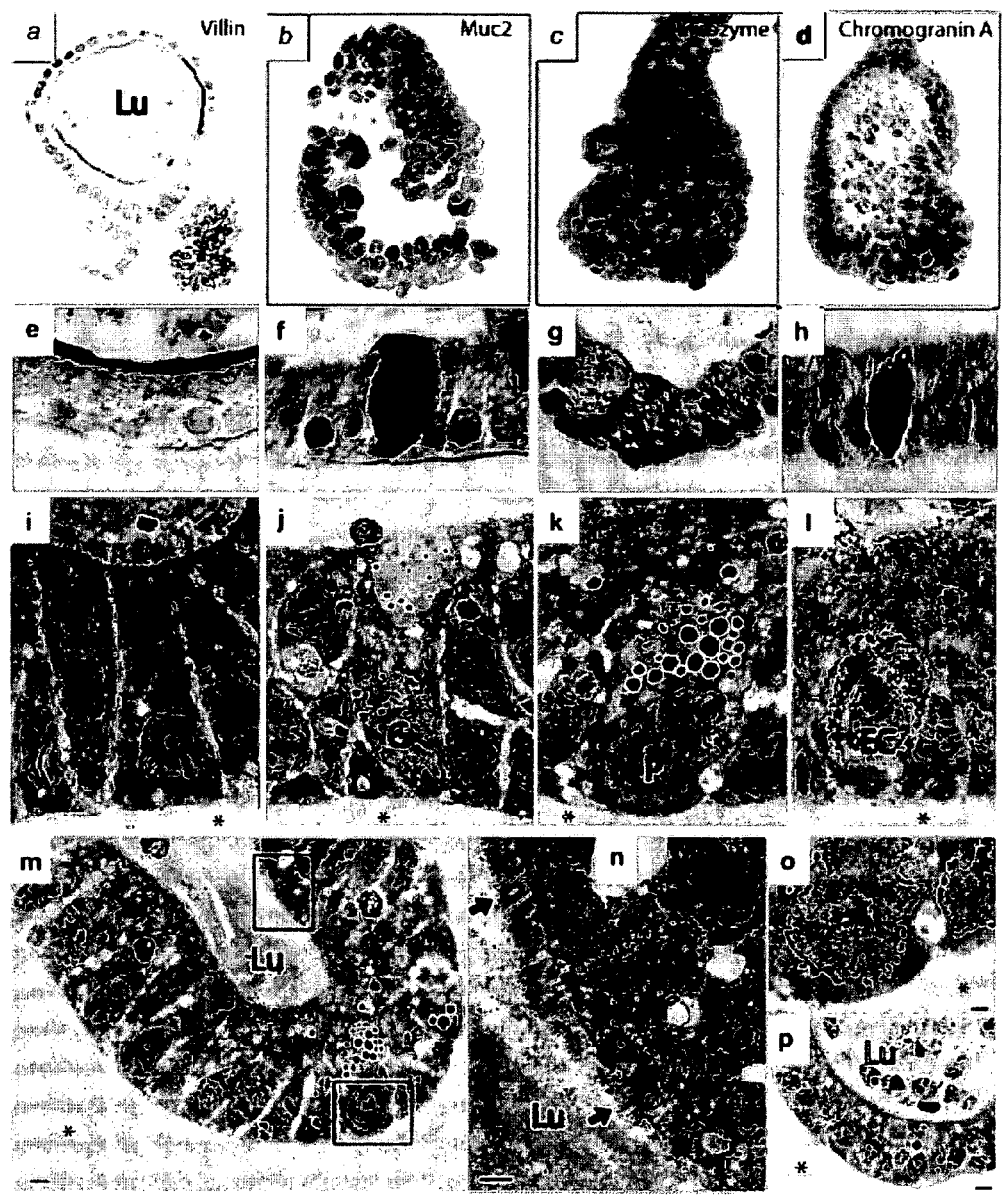
FIG. 11. Composition of single stem cell-derived organoids. Panels a-d: Three-dimensional reconstructed confocal image for Panel a: Villi in light grey (apex of enterocytes lining central lumen), Panel b: Muc2 staining indicated by white arrows (goblet cells), Panel c: lysozyme in light grey (Paneth cells), Panel d: Chromogranin A in light grey (enteroendocrine cells). Nucleus was counterstained with DAPI. Panels e-g: Paraffin section staining Panel e: Alkaline phosphatase in black (apex of enterocytes lining central lumen), Panel f: PAS in dark grey (goblet cells), Panel g: lysozyme in dark grey (Paneth cells), Panel h: Synaptophysin in dark grey (enteroendocrine cells). Panels i-p: Electron microscopy sections of crypt organoids demonstrates the presence of enterocytes (Panel i), goblet cells (Panel j), Paneth cells (Panel k) and enteroendocrine cells (Panel 1). Panels m-o: Low power crypt image illustrates absence of stromal cells. Panels n and o: Higher magnification of Panel m. Panel n: Maturation of brush border towards the luminal compartment of the organoid, as indicated by the difference of length of microvilli (black arrows). Panel p: Low power image of villus domain. Lu, lumen of crypt organoid filled with apoptotic bodies and lined by polarized enterocytes. G, goblet cells; EC, enteroendocrine cells; P, Paneth cells; asterisk, matrigel. Scale bar: 5 µm (Panels m, p), 1 µm (Panels n, o).
Figure 12:
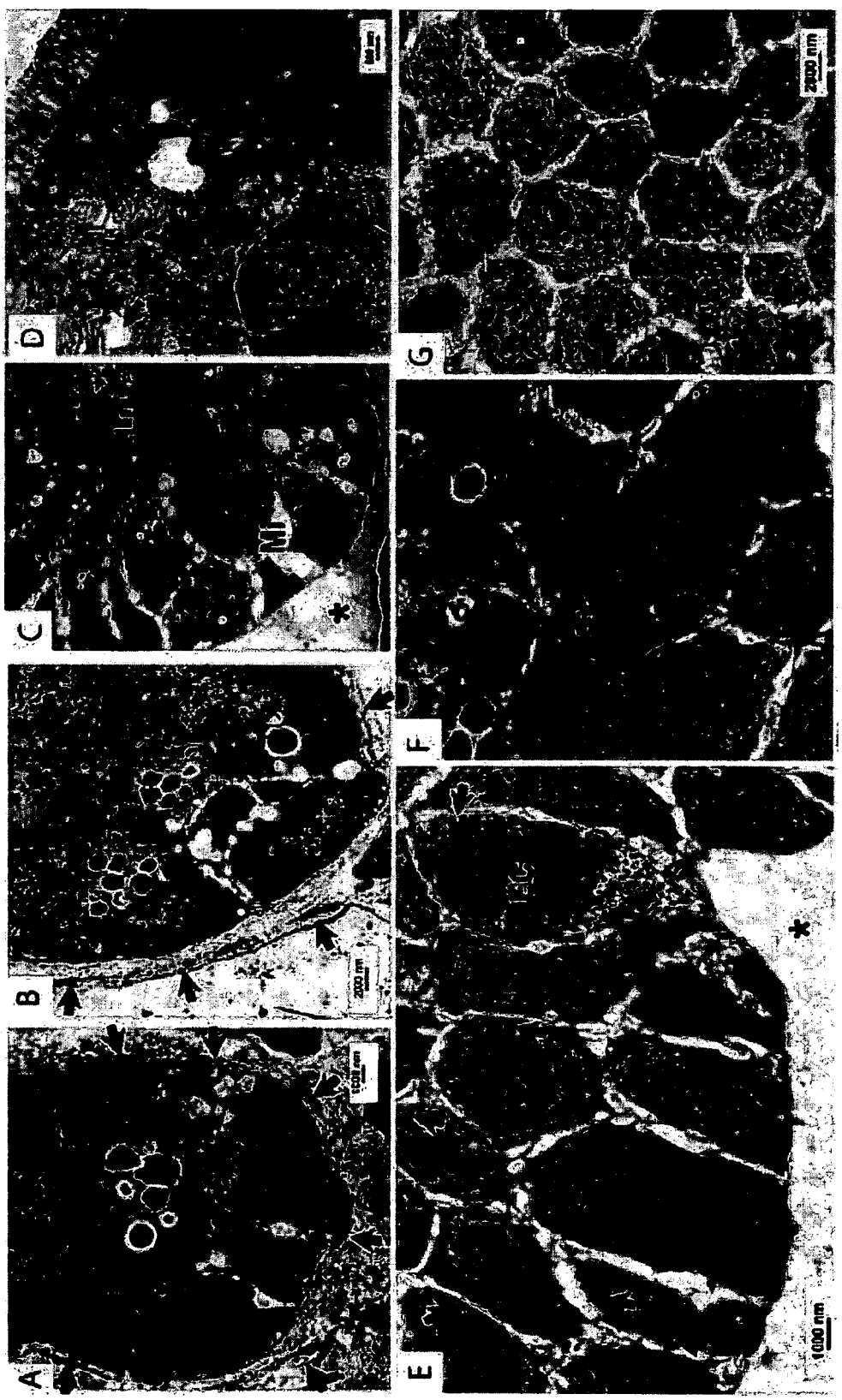
FIG. 12. Comparison of electron microscopic images between in vivo crypt and in vitro cultured crypt. Panels A and B: Normal intestine at the base of the crypt with the connective tissue underneath (arrows). For comparison, see Panels C-G of the organoids also taken at the base of a crypt. Panel D: High magnification image from the apical membrane; there are intercellular clefts (arrows) between the membranes of two adjacent cells. Note the desmosome (arrow head) followed by an intercellular cleft. Panel E: High magnification from the basal site where the membrane of two adjacent cells can be followed by intracellular clefts. These images are comparable to Panels A and B from the intestine of a normal mouse. The cause of these intercellular clefts may be osmotic shock during aldehyde fixation. Panels F and G: All cells that make up the organoid are in a healthy state and lack large vacuoles or other signs of stress. One can observe mitosis figures (Panel C) and in each cell, many nuclear pores (Panel F, arrows) and intact mitochondria. ER and Golgi (Panel G) can be seen without any evidence of swelling. There is no sign of karyorexis, karyolysis or karyopyknosis. Therefore, no sign of cell lysis or apoptosis is observed. Cells in the lumen of the organoid show the expected apoptotic features as one can observe in the gut of a normal mouse. Panel F shows another example of an enteroendocrine cell. Mi: mitotic cells, Lu: lumen, EC: enteroendocrine cells, G: Golgi.

The single stem cell-derived organoids appeared indistinguishable from those derived from whole crypts. Paneth cells and stem cells were located at crypt bottoms (FIG. 8, Panels e, f, FIG. 11, Panels c, g). Fully polarized enterocytes as evidenced by Villin+ mature brush borders and apical alkaline phosphase lined the central lumen (FIG. 11, Panels a, e, i). Goblet cells (Muc2+, FIG. 11, Panel b; PAS+, FIG. 11, Panel f) and enteroendocrine cells (chromogranin A+, FIG. 11, Panel d; synaptophysin+, FIG. 11, Panel h) were scattered throughout the organoid structure. Four types of mature cells were recognized by electron microscopy (FIG. 11, Panels i-l). Non-epithelial (stromal/mesenchymal) cells were absent, an observation confirmed by EM imaging (FIG. 11, Panels i-p, FIG. 12, Panels C-G). Both the crypts (FIG. 11, Panels m, o) and the central luminal epithelium (FIG. 11, Panel p) consisted of a single layer of polarized epithelial cells resting directly on the matrigel support. High resolution images of these EM pictures are given in FIG. 5. Organoid stained for E-cadherin in red and counter-stained with nuclei in blue, reveals the single-layered nature of the organoid epithelium (data not shown).

It is well known that epithelial crypts are in intimate contact with subepithelial myofibroblasts[26-28] and it is generally believed that the latter cells create a specialized cellular niche at crypt bottoms.[27, 29, 30] Such a niche would create a unique environment to anchor and support the intestinal stem cells. We now show that a self-renewing epithelium can be established by a limited set of growth signals that are uniformly presented. Despite this, the isolated stem cells autonomously generate asymmetry in a highly stereotypic fashion. This rapidly leads to the formation of crypt-like structures with de novo-generated stem cells and Paneth cells located at their bottoms and filled with TA cells. These crypt-like structures feed into villus-like luminal domains consisting of postmitotic enterocytes, where apoptotic cells pinch off into the lumen, reminiscent of cell loss at villus tips. The paradoxical observation that single cells exposed to a uniform growth-promoting environment can generate asymmetric structures is particularly evident upon scrutiny of the Wnt pathway. While all cells are exposed to R-spondin 1, only cells in crypts display hallmarks of active Wnt signaling, i.e., nuclear β-catenin and the expression of Wnt target genes. Apparently, differential responsiveness to Wnt signaling rather than differential exposure to extracellular Wnt signals lies at the heart of the formation of a crypt-villus axis.

In summary, we conclude that a single Lgr5$^{+ve}$ intestinal stem cell can operate independently of positional cues from its environment and that it can generate a continuously expanding, self-organizing epithelial structure reminiscent of normal gut. The described culture system will simplify the study of stem cell-driven crypt-villus biology. Moreover, it may open up new avenues for regenerative medicine and gene therapy.

Example 2

Culturing of Colon Crypts and Villi In Vitro

Material and Methods
Wnt3a-Conditioned Medium

A Wnt3a ligand-expressing cell line and the same cell line, without the Wnt3a ligand (control medium) are cultured for a period of three to four weeks. The cells will produce Wnt3a as soon as they stop growing at confluency. The medium will be harvested and tested in the TOPflash assay, a luciferase assay using a TCF-responsive elements-luc construct (TOP) and the same construct, but with mutations in the TCF-responsive elements (FOP). The ratio between TOP/FOP should be more than 20 for the medium to be used in cultures. The medium is diluted 25%-50% when used in the cultures to regenerate tissue.

Freshly isolated colon was opened and washed with PBS or DMEM, and cut into small pieces. The fragments were incubated with 2 mM EDTA/PBS for 1 hour at 4° C. under gentle rocking. Following removal of EDTA solution, the tissue fragments were vigorously suspended in 10 ml of cold PBS with a 10 ml pipette. The first supernatant-containing debris was discarded and the sediment was suspended with 10 ml to 15 ml PBS. After further vigorous suspension of the tissue fragments, the supernatant is enriched in colonic crypts. The fragments were pelleted and mixed with matrigel and cultured as small intestinal organoid culture system. The matrigel was incubated for five to ten minutes at 37° C. After matrigel polymerization, 500 μl of tissue culture media (50% Advanced-DMEM/F12/50% Wnt-3a-conditioned medium supplemented with 200 ng/ml N-Acetylcysteine, 50 ng/ml EGF, 1 μg/ml R-spondin 1, 100 ng/ml Noggin, 100 ng/ml BDNF (Peprotech) was added. The entire medium was changed every two to three days. For passage, the organoids were removed from the Matrigel using a 1000 μl pipette and were dissociated mechanically into small fragments and transferred to fresh Matrigel. Passage was performed in 1:4 split ratio at least once every two weeks. Under these conditions, cultures have been maintained for at least three months.

Results

Figure 13:
FIG. 13. Colon-derived crypts can be maintained in culture as well. Single isolated crypts derived from colon efficiently form crypt organoids using the same culturing conditions as used for small intestinal crypts. Through repeated crypt fission, the structures generate numerous octopus-like crypt organoids at day 14.
Figure 14A:
FIG. 14. Addition of BDNF increases culture efficiency. Single isolated colon crypts were cultured in the presence of EGF, Noggin, R-spondin and BDNF. Images of colon crypt organoids taken at days 0, 4 and 14 after the start of the culture.
Figure 14B:
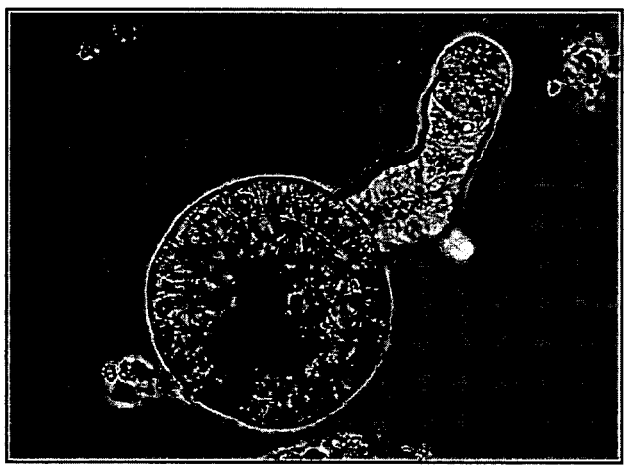
Figure 14C:
Figure 15:
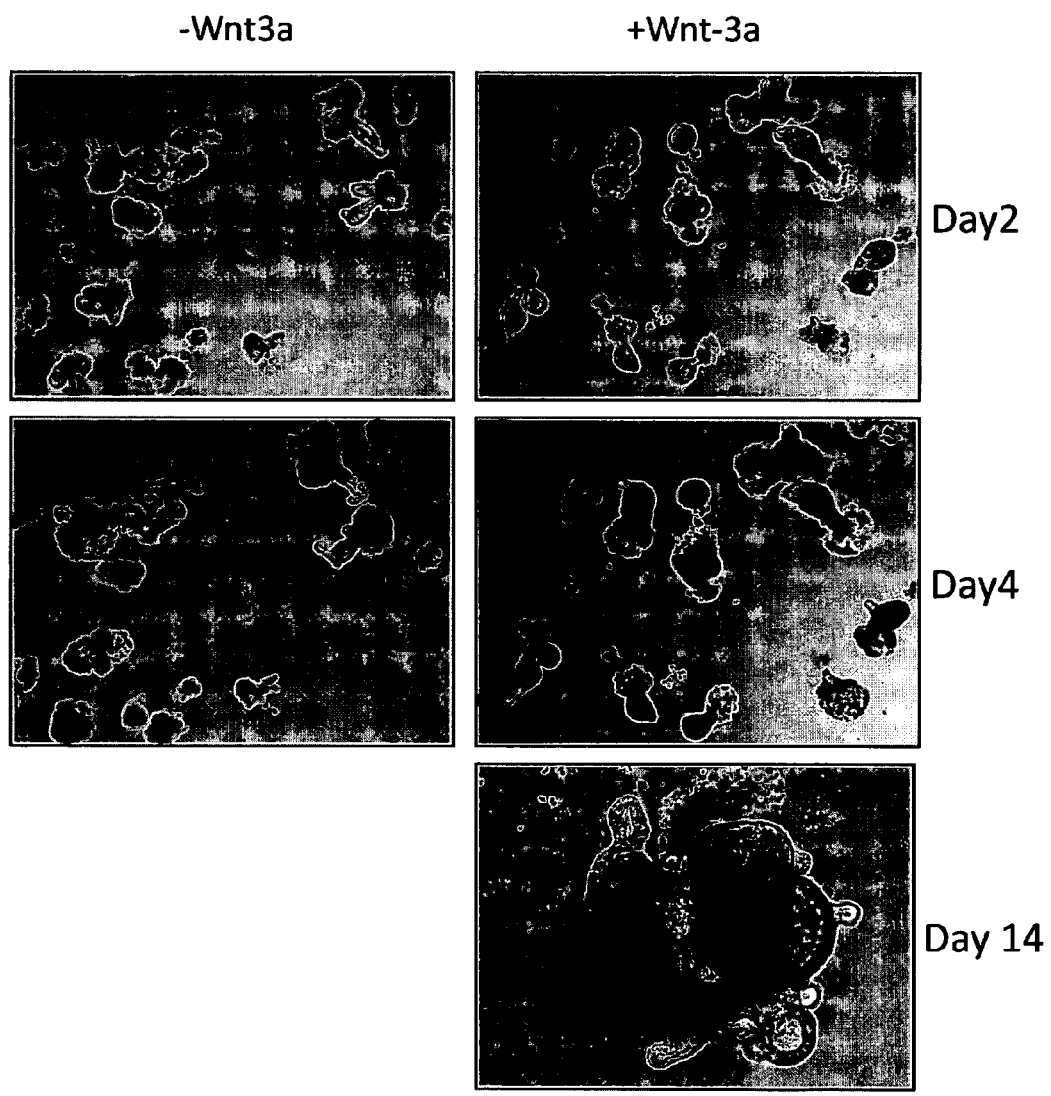
FIG. 15. Addition of Wnt3a further increases culture efficiency of colon crypt organoids. Single isolated colon crypts were cultured in the presence of EGF, Noggin, R-spondin. The use of Wnt3a-conditioned medium (+Wnt3a) increased culture efficiency up to 30%, compared to culturing colon organoids in control medium (−Wnt3a).

Colonic organoids grow slower and less efficient as compared with small intestinal organoids. With the same growth factors condition as small intestine, less than 5% of colonic crypts isolated from distal colon grew and formed organoid structure (FIG. 13). It was difficult to grow colonic crypts from proximal part of colon. Since we found up-regulation of trkB, the receptor of BDNF (brain-derived neurotrophic factor) in the microarray analysis (colon Lgr5-GFP hi cells vs colon Lgr5-GFP low cells), we determined the effect of BDNF for colonic organoids. We constantly observed around two-fold higher culture efficiency in BDNF+ culture than BDNF- culture. Typically, one colon organoid would contain approximately ten crypt domains (FIG. 14). Consistent with their origin, no Paneth cells could be detected. Compared with small intestinal organoids, colonic crypt possesses no Wnt-3a-producing Paneth cells in the crypt base, therefore, supplementation of Wnt-3 increases culture efficiency of colonic crypts but not that of small intestinal crypts. Typically, we obtained up to 30% culture efficiency when we added Wnt-3a-conditioned medium (FIG. 15).

In conclusion, both small intestine-derived and colon-derived crypts can be maintained and propagated in vitro using the above-described conditions, making this the first culture method ever described to result in the generation of intestinal epithelium in an artificial system.

Example 3

Culturing of Adenomas In Vitro

Materials and Methods
(See Example 1.)
Results

Figure 16:
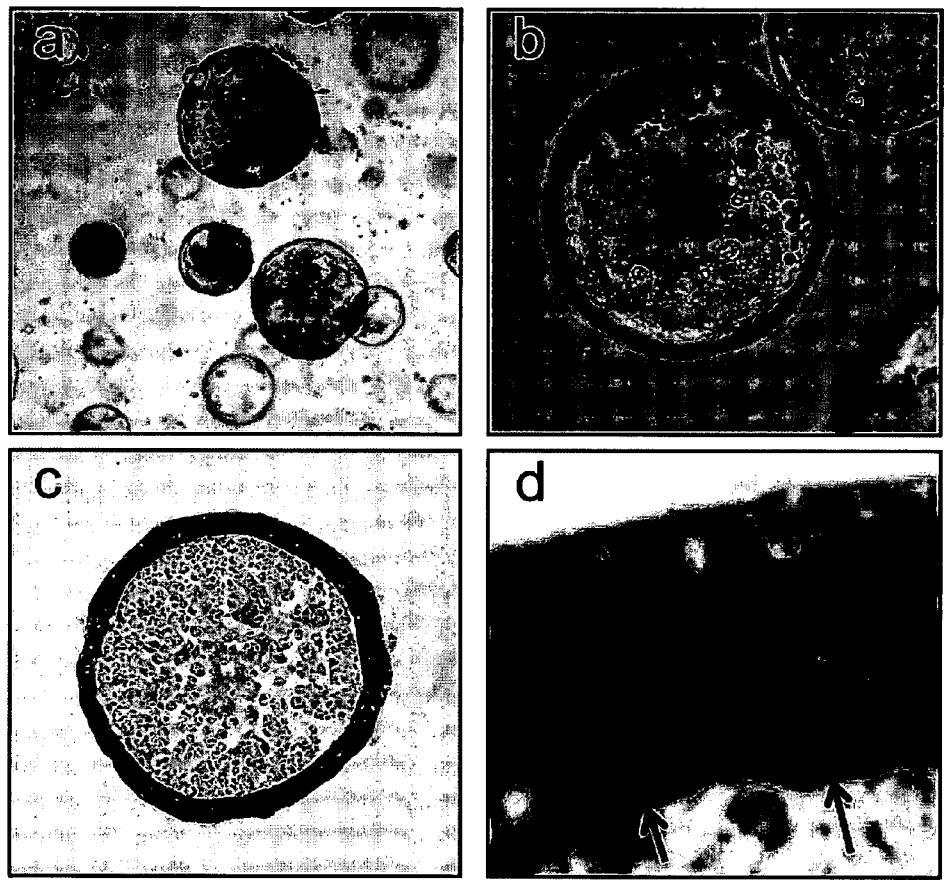
FIG. 16. Adenoma isolated from APC−/− mice can grow in vitro. Single isolated adenoma from APC−/− mice were dissociated and cultured using conditions as described above with the exception that R-spondin was not included in the culture media. Panel a: Adenoma organoids as shown here on day 4 generally grow as a simple cyst, containing one central lumen containing apoptotic cells. Panel b: A larger magnification of one adenoma organoid. Panel c: One adenoma organoid was stained with β-Catenin (dark grey) and hematoxylin (light grey in lumen). The outer layer of the organoid consists of epithelial cells with a nuclear β-Catenin staining. The inner lumen contains dead cells that have taken up hematoxylin, staining dark grey. Panel d: A larger magnification of the outer layer of epithelial cells showing clear nuclear β-Catenin.

Adenomas have been historically difficult to culture in vitro. Since the above-described conditions were used to successfully culture healthy crypts derived from small intestine as well as colon, it was determined whether similar conditions could sustain adenomas in vitro. After isolation of adenoma from APC−/− mice using 2.5 mM EDTA, single adenomas were cultured under similar conditions as described above. Importantly, these conditions were adequate to maintain growth of the adenomas in vitro, however, R-spondin had become redundant. This can be easily explained by the fact that it no longer is necessary to induce the Wnt signaling pathway, since the absence of APC in these cells will automatically result in nuclear β-Catenin. This makes R-spondin, a Wnt agonist, redundant in culturing adenomas in vitro. FIG. 16, Panel a, and in larger magnification in FIG. 16, Panel b, show that, in contrast to noinial crypt organoids in which you can see crypt budding with central lumen, adenoma organoids simply grow as cysts. Dead cells are shed off into the lumen, as can be concluded from the presence of a large quantity of dead cells inside the lumen. In not crypt organoids, nuclear β-catenin is only seen in base of crypt-domain (see FIG. 4, Panel a). In adenoma organoids (FIG. 16, Panel c, and a larger magnification in FIG. 16, Panel d), nuclear β-catenin was seen in every epithelial cell, consistent with the genetic APC mutation. These organoids can be passaged indefinitely.

It was further tested whether single Lgr5+ sorted cells derived from the adenomas in Lgr5-EGFP-Ires-CreERT2/APCflox/flox mice were able to foam similar adenoma organoids in vitro using the aforementioned culture conditions (without R-spondin). Indeed, this was the case and the organoids obtained were highly comparable in structure to those that were obtained using complete adenomas as starting material for the in vitro culture (data not shown).

Example 4

Testing the Effect of Other Wnt Agonists

To determine whether other Wnt agonists have the same effect as R-spondin does, namely facilitate formation of crypt-villus organoids in vitro, soluble Wnt3a was added to Lgr5+ sorted single cells and the effect on crypt-villus formation in vitro was assessed.

Materials and Methods

Lgr5-GFP$^{hi}$ cells were sorted and cultured with or without Wnt3a (100 ng/ml) in addition to conventional single cell culture condition (EGF, noggin, R-spondin, Notch ligand and Y-27632, as described above for single cells). We seeded 100 cells/well and counted the number of organoids 14 days after seeding.

Isolated crypts were incubated with 1 μM Newport Green-DCF (MolecularProbes) in PBS+0.1% Pluronic 127 (Sigma) for three minutes at room temperature, followed by PBS wash. After this, crypts were embedded in Matrigel and cultured using the standard conditions as described above.

Results

Figure 17A:
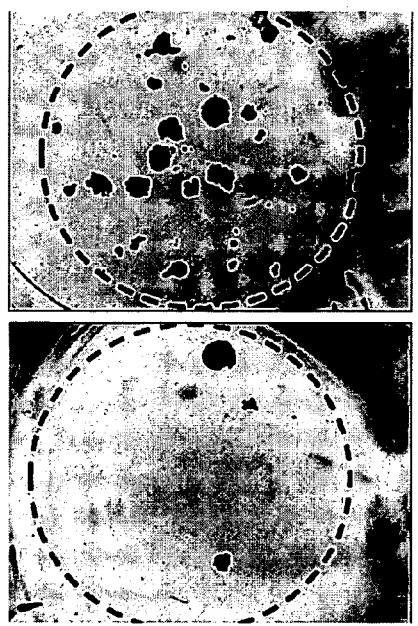
FIG. 17a: Lgr5-GFP$^{hi}$ cells were sorted and cultured with or without Wnt3a (100 ng/ml) in addition to conventional single-cell culture condition (EGF, noggin, R-spondin, Notch ligand and Y-27632, as described above for single cells). These images of dishes with cultured organoids in the presence and absence of Wnt3a are representative.
Figure 17B:
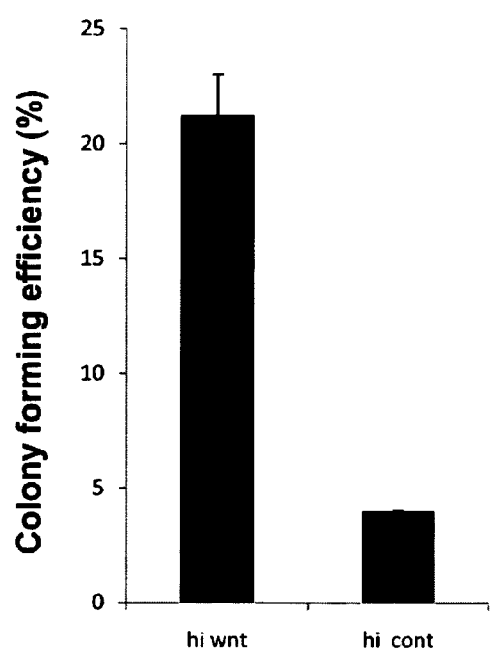
FIG. 17b: 100 cells/well were seeded and the number of organoids were 14 days after seeding. The number of organoids/dish is represented in this graph.
Figure 18:
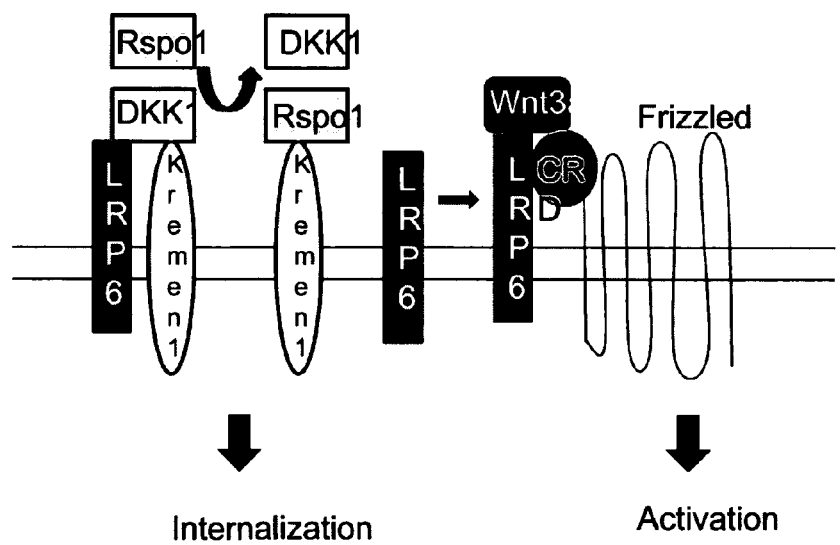
FIG. 18. Model for R-spondin 1 function. Wnt/β-catenin signaling is initiated upon binding of a canonical Wnt ligand to Frizzled and association with LRP5/6 receptors. In the absence of R-spondin 1, Wnt signaling is limited by the amount of LRP6 on the cell surface, which is kept low by DKK1/Kremen1-mediated internalization. R-spondin 1 enhances Wnt signaling by antagonizing DKK1/Kremen1-mediated LRP6 turnover, resulting in increased cell surface levels of LRP6. This figure was taken from *PNAS* 104:14700, 2007.

The addition of Wnt3a in the absence of R-spondin did not have any effect on colony formation: little to no colonies were formed in the absence of R-spondin. However, in the presence of R-spondin, an increased efficiency in organoid formation was observed only in the presence of Wnt3a (FIG. 17). This indicates that both factors support each other in their ability to stimulate and support differentiation of stem cells into all cells necessary for the formation of a complete epithelial cell layer. The current hypothesis is that R-spondin is responsible for inhibition of internalization of a co-receptor of Frizzled, LRP6, prior to signaling through Frizzled. Upon binding of the Wnt factor to Frizzled and the co-receptor LRP6, the Wnt signaling pathway is activated.[31] When LRP6 is present on the cell surface, Wnt activation will take place (FIG. 18). Therefore, if R-spondin is not present in the culture medium, Wnt3a will not be able to activate the Wnt pathway, since LRP6 is internalized and not available for signaling in combination with the Wnt factor, thereby preventing activation of the Wnt pathway.

Figure 19:
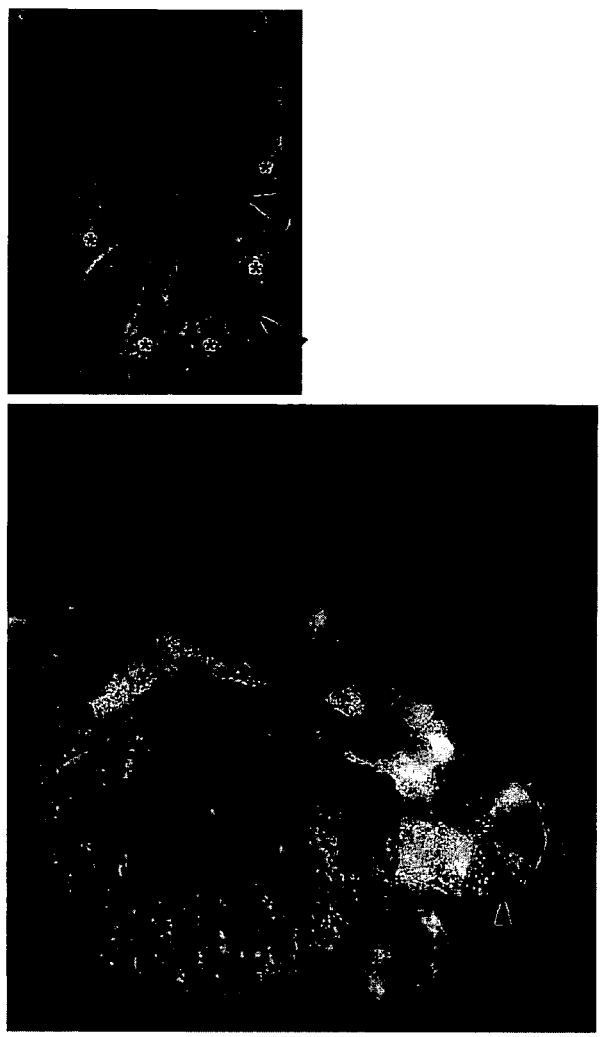
FIG. 19. Paneth cells are located adjacent to Lgr5$^+$ stem cells in the small intestines. Crypts were isolated from the small intestine of Lgr5-EGFP-ires-CreERT2 knock-in mice. Examples of representative crypts are presented here. The GFP$^+$ cells are Lgr5$^+$ (light grey, indicated by black arrows) and these are generally located adjacent to Paneth cells (indicated by *).
Figure 20:
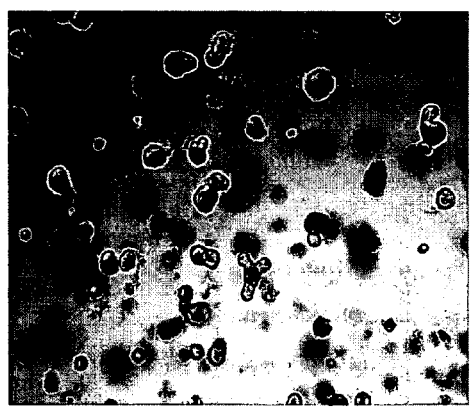
FIG. 20. In the absence of viable Paneth cells, efficiency of organoid formation is reduced. Isolated crypts were incubated with 1 µM Newport Green-DCF (Molecular probe) in PBS+0.1% Pluronic 127 (Sigma) for three minutes at room temperature, followed by PBS wash. After this, crypts were embedded in Matrigel and cultured using the standard conditions as described above.
Figure 20:
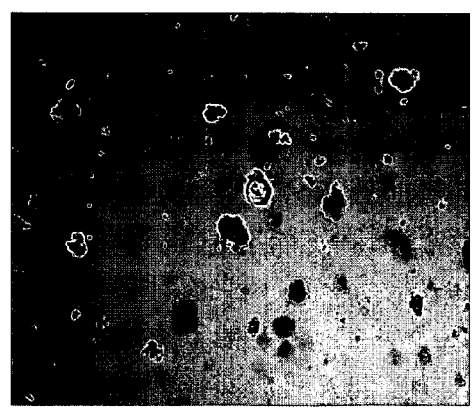

Wnt3a is a soluble factor that, under physiological circumstances, is produced by Paneth cells. These cells are generally located adjacent to the stem cells (FIG. 19) and it is hypothesized that these cells support the maintenance of the ongoing differentiation of the intestinal epithelial cell layer. Other Wnt factors that are also secreted by Paneth cells are Wnt6, 9b and 11. It is anticipated that Wnt6 will have the same effect on stem cell differentiation as Wnt3a does. These findings support the notion that Paneth cells are important for the formation of a stem cell niche. These data are surprising, since a stem cell niche has been extensively speculated on, but so far, no experimental data have supported the existence of such a niche. Additional support for the presence of a stem cell niche comes from an experiment in which Paneth cells were selectively killed. Crypts were isolated from the mouse small intestine and cultured in vitro in the presence of a zinc chelator[32] that specifically eradicates Paneth cells. This was used at such low concentrations and for such a short time that it only affects the Paneth cells and not other cells within the crypt. After treatment with the zinc chelator, organoid formation was assessed. A significant reduction of organoid formation was observed when Paneth cells were no longer present in the original crypts (FIG. 20). In the presence of Wnt3a, this reduction was partially restored (data not shown). This supports a role for the Paneth cell in the maintenance of a stem cell niche, which supports the differentiation of the Lgr5+ stem cells in the crypt.

Example 5

Culture Conditions Support the Growth of Stomach Organoids as Well

The stomach consists of three topographic regions (fundus, corpus, and antrum) and two functional glandular areas (oxyntic and pyloric). The oxyntic gland area comprises 80% of the organ whereas the pyloric area comprises the 20% of the organ. The mammalian gastric epithelium is organized into gastric units consisting of a planar surface epithelium, a short pit and a long gland. The pit is lined by mucous-secreting cells whereas the gland is composed of secreting cells separated in three regions: the isthmus, the neck and the base. The gastric epithelium is constantly renewed. Tracing studies performed in our laboratory have shown that LGR5-positive cells located at the gland base fulfill the definition of sternness (Barker et al. under preparation).

So far, gastric monolayer cultures have not been able to recapitulate the features of the gastric unit, which is formed by several differentiated gastric cells. Furthermore, the three-dimensional culture method systems reported only reconstruct highly differentiated gastric surface mucous cells, without showing any endocrine cells. Moreover, these cultures had only been carried out over a period of seven days, thus indicating a lack of self-renewing capacity (A. Ootani, S. Toda, K. Fujimoto, H. Sugihara, *Am. J. Pathol.* 2003 June; 162(6):1905-12). Here, we have developed a method to isolate gastric units from the pyloric region of the murine stomach and have been able to develop a three-dimensional culture system that shows longer-lived maintenance.

Materials and Methods

Gastric Unit Isolation

Isolated stomachs were opened longitudinally and washed in cold Advanced-DMEM/F12 (Invitrogen). Under the stereoscope, the pyloric region was excised and isolated from the body and forestomach and the pyloric mucosa was carefully separated from the muscle layer with tweezers. Then, the tissue was chopped into pieces of around 5 mm and further washed with cold isolation buffer ($Na_2HPO_4$ 28 mM+$KH_2PO_4$ 40 mM+NaCl 480 mM+KCl 8 mM+Sucrose 220 mM+D-Sorbitol 274 mM+DL-Dithiotreitol 2.6 mM). The tissue fragments were incubated in 5 mM EDTA with isolation buffer for two hours at 4° C. under gentle rocking. Following removal of EDTA solution, the tissue fragments were vigorously suspended in 10 ml of cold isolation buffer with a 10 ml pipette. The first supernatant containing dead cells was discarded and the sediment was suspended with 10 ml to 15 ml cold isolation buffer. After further vigorous suspension of the tissue fragments, the supernatant is enriched in gastric units. Every ten to twenty suspensions, the supernatant is replaced for fresh cold isolation buffer and is kept on ice and checked for the presence of gastric units. This procedure is repeated until the complete release of the gastric units, usually four to five times. Enriched gastric unit suspensions are centrifuged at 600 rpm for two to three minutes to separate the isolated gastric units from single cells and the sediment is used for culture.

Gastric Culture

Entire gastric units containing the gland, isthmus and pit regions were isolated from the pyloric region of murine stomach by incubating with 5 mM EDTA at 4° C. for two hours as indicated in the previous section. Isolated gastric units were counted and pelleted. 100 gastric units were mixed with 25 µl of Matrigel (BD Bioscience), seeded on 48-well tissue culture plates and incubated for five to ten minutes at 37° C. until complete polymerization of the Matrigel. After polymerization, 250 µl of tissue culture media (Advanced-DMEM/F12 supplemented with B27, N2, 200 ng/ml N-Acetylcysteine, 50 ng/ml EGF, 1 µg/ml R-spondin 1, 100 ng/ml Noggin, 100 ng/ml Wnt3A, 50 or 100 ng/ml KGF) was added. The entire medium was changed every two days. For passage, the organoids were removed from the Matrigel using a 1000 µl pipette and were dissociated mechanically into small fragments and transferred to fresh Matrigel. Passage was performed in 1:4 split ratio once or twice per week. Under these conditions, cultures have been maintained for at least one month.

Reagents

Advanced DMEM/F12 and supplements N2 and B-27 Serum-Free Supplement were purchased from Invitrogen and N-Acetylcysteine from Sigma. Murine recombinant EGF, Noggin and human KGF were purchased from Peprotech, and Wnt3A recombinant protein from Stem Cell Research. From the mentioned growth factors, different concentrations have only been tested for R-spondin 1 and KGF. At 50 ng/ml, R-spondin 1 inhibits culture growth. KGF can be used either at 50 or 100 ng/ml but the budding efficiency is higher in the 100 ng/ml condition.

Wnt3A-conditioned media was prepared as previously described (K. Willert, J. D. Brown, E. Danenberg, A. W. Duncan, I. L. Weissman, T. Reya, J. R. Yates 3rd, R. Nusse, *Nature* 2003 May 22; 423(6938):448-52).

Immunohistochemistry and Imaging Analysis

For X-gal staining, organoids were directly fixed in the matrigel with 0.25% glutaraldehyde (Sigma) in 100 mM $MgCl_2$ in PBS, for one to two hours at room temperature. After, cultures were washed three times with washing solution (0.01% Sodium Deoxycholate+0.02% NP40+5 mM $MgCl_2$ in PBS) and incubated for 16 hours at 37° C. with 1 mg/ml X-Gal (Invitrogen) in the presence of 0.21% $K_4Fe(CN)_6$ and 0.16% $K_3Fe(CN)_6$. After washing in PBS, cultures were post fixed with 2% PFA in PBS for 15 minutes at room temperature. All reagents were acquired from Sigma.

For immunohistochemistry, organoids were isolated from the matrigel using trypsine (Tryple Select, Invitrogen), fixed with 4% PFA for one hour at room temperature and embedded in paraffin. Paraffin sections were processed with standard techniques and immunohistochemistry was performed as previously described. The following antibodies were used anti-mouse Ki67 (clone MM1, Monosan) (1:200), anti-rabbit cleaved caspase-3 (Cell Signaling Technology) (1:400) and anti-human gastric mucin 5AC (Novocastra clone 45M1) (1:200). Citrate buffer antigen retrieval was performed in all cases. Sections were counterstained with Mayer's haematoxylin.

The images of gastric organoids and isolated gastric glands were taken with either inverted microscope (Nikon DM-IL) or confocal microscopy (Leica SP5).

Results

So far, gastric cultures have been grown in monolayers. Monolayer cultures, however, lack the ability to recapitulate the features of the entire gastric unit, which is formed by several differentiated gastric cells (pit mucous cells, enteroendocrine cells and proliferating mucous-free cells). Recently, our laboratory has demonstrated by in vivo lineage tracing, that the Lgr5-positive cells present at the bottom of the intestinal crypts are true intestinal stem cells (N. Barker, J. H. van Es, J. Kuipers, P. Kujala, M. van den Born, M. Cozijnsen, A. Haegebarth, J. Korving, H. Begthel, P. J. Peters, H. Clevers, *Nature* 2007; 449:1003-7). As the intestinal epithelium, the gastric epithelium is constantly renewed. Lgr5-positive cells have been found at the bottom of the pyloric gastric gland units and tracing studies have shown that these LGR5-positive cells fulfill the definition of stemness by showing self-renewal and multipotency capability (Barker et al. under preparation). Since we have been able to culture intestinal crypts from single Lgr5+ cells in three-dimensional structures, it was determined whether similar conditions could sustain the growth of pyloric gastric units in vitro.

Figure 21A:
(FIG. 21a) GFP (arrows, indicating GFP-positive cells) and DIC image of isolated gastric glands from the pyloric region of the stomach of Lgr5-GFP mice. Nuclei are stained with DAPI. Magnification 63× (FIG. 21b) 100 gastric glands/well were seeded in duplicates with EGF (E), R-spondin 1 (R), Noggin (N), EGF+R-spondin 1 (ER), EGF+Noggin (EN), EGF+R-spondin 1+Noggin (ERN), EGF+R-spondin 1+Noggin+Wnt3A (ERNW) or EGF+R-spondin 1+Noggin+Wnt3A+KGF (ERNWK). The number of gastric organoids was counted 2, 5 and 7 days later. Results are shown as mean±SEM of two independent experiments.
Figure 21B:
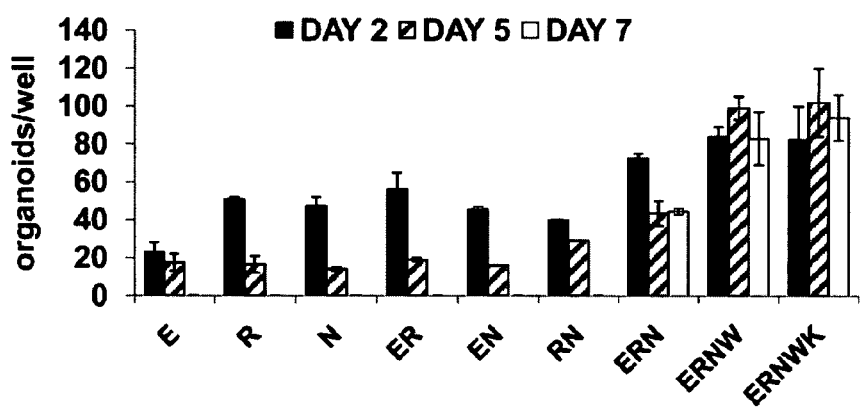
FIG. 21. Efficiency of gastric organoid culture.
(FIG. 21c) 100 gastric glands/well were seeded in duplicates with Wnt3A recombinant protein (ENRWK) or Wnt3A-conditioned media (ENRWCMK) supplemented with the other growth factors described in FIG. 21a. The number of budding organoids was counted at day 7 after seeding and at day 2 after the first passage.
Figure 21C:
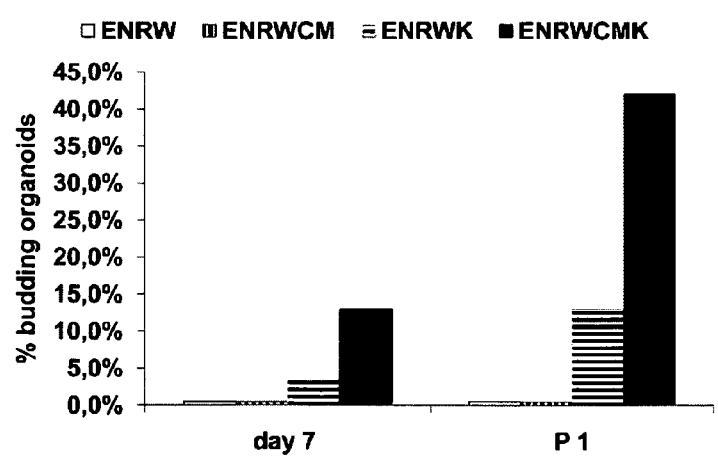

After isolation of gastric gland units using 5 mM EDTA, gastric glands (FIG. 21a) were suspended in Matrigel. Gastric culture growth required EGF (50 ng/ml), Noggin (100 ng/ml), R-spondin 1 (1 ug/ml) and Wnt3A (100 ng/ml) (FIG. 21b). KGF (50 or 100 ng/ml) was essential for the formation of budding events and, therefore, the expansion of the cultures. Thus, the cultured pyloric units behaved as the intestinal crypt organoids. The opened upper part of the unit is sealed and the lumen is filled in with apoptotic cells. The newly formed gastric organoids underwent continuous budding events (reminiscent of gland fission) while maintaining their polarity with the gastric glands budding with a central lumen. When Wnt3A-conditioned media, which shows ten to one hundred times higher Wnt activity when compared to the recombinant Wnt3A recombinant protein, was used, a significant increase in the efficiency of budding formation was detected (FIG. 21c), revealing a Wnt dose-dependence for the budding formation and morphogenesis.

Figure 23:
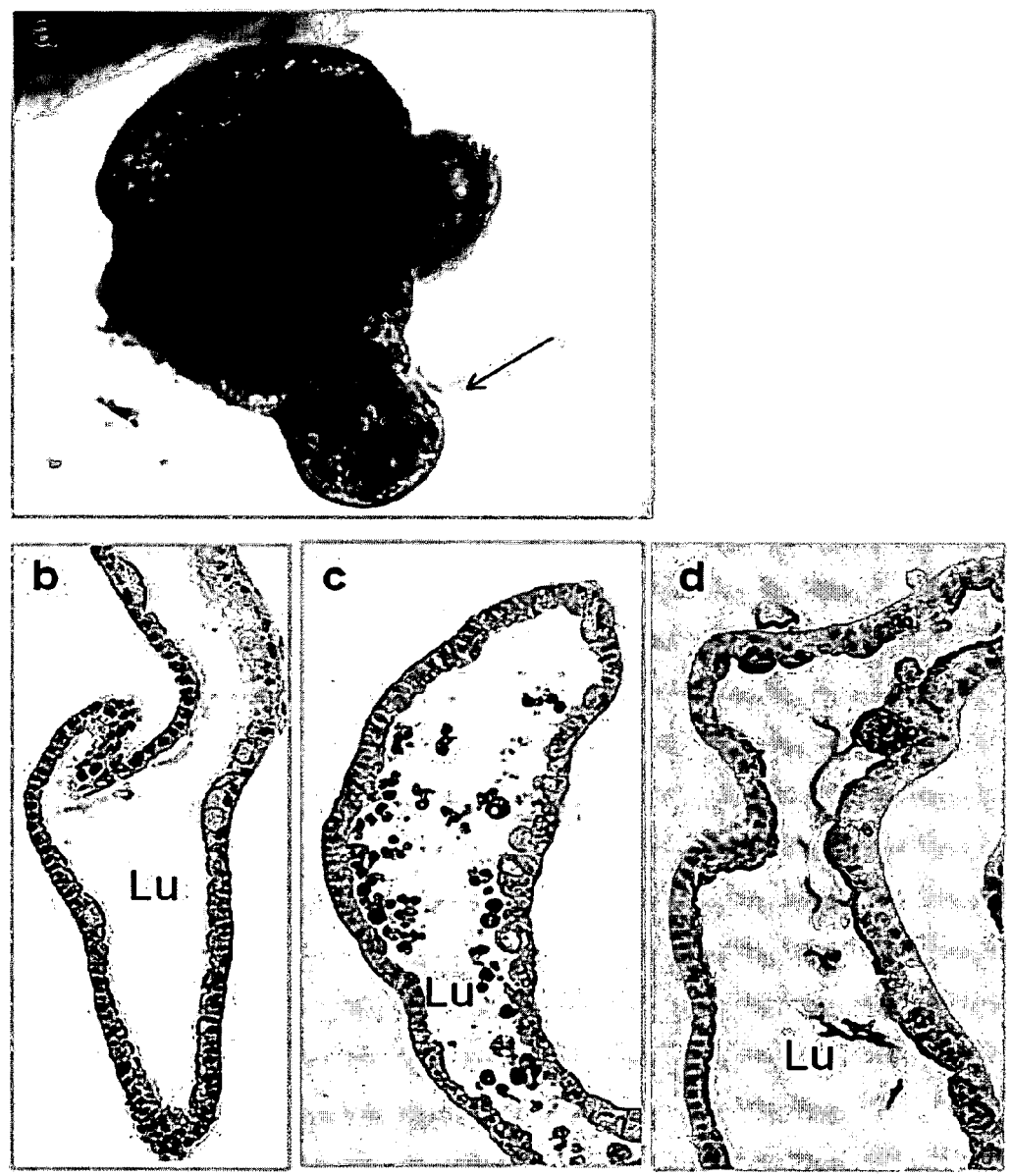
FIG. 23. Markers of gastric glands (Panel a) gastric cultures from Lgr5-LacZ mice. Lac Z expression was detected in the gastric budding at day 5 after seeding (see arrow, indicating LacZ-positive (dark grey) cells), indicating the presence of Lgr5-positive cells. Magnification 20×. (Panel b) Ki67 staining (black) shows positive proliferating cells at the base of the gland-like structure. (Panel c) caspase-3 (dark grey) apoptotic cells present inside the lumen of the organoid (Panel d) Gastric mucin 5AC-positive (dark grey) cells present in the gastric organoids. Lu, organoid lumen. Magnification 20×.

Organoids have been cultured for at least one month without losing the properties described. Weekly, organoids are passaged 1:4 by mechanical dissociation (FIG. 22). Culture of Lgr5-LacZ pyloric gastric units revealed the presence of Lgr5-positive stem cells in the gastric organoids (FIG. 23, Panel a). As evidenced by Ki67 staining, proliferating cells are located at the base of the gland-like structures (FIG. 23, Panel b) while apoptotic caspase 3-positive cells are found extruded into the lumen (FIG. 23, Panel c). The gastric mucin 5AC (MUC5AC) is a specific marker of the gastric pit cells, also named as foveolar cells. MUC5AC-positive cells are found in the organoids, indicating the presence of at least one differentiated gastric cell lineage (FIG. 23, Panel d). However, no endocrine-derived cells have been detected. Therefore, additional factors are required. These would include gastrin-releasing peptide, activators or inhibitors of the Hedgehog and Notch families, other activators of the Wnt pathway and other inhibitors of the BMP family, activators of the TGF family.

Example 6a

Pancreas Organoids can be Grown In Vitro

Material and Methods

Freshly isolated pancreas was cut into small pieces, and incubated in DMEM (Invitrogen) with digestive enzyme mixture (300 U/ml Collagenase typeXI (Sigma), 0.01 mg Dispase I (Roche) and 0.1 mg DNase) for 10 minutes in orbital shaker (80 rpm, 37° C.). After incubation, the tissue fragments were mildly dissociated by mechanical pipetting. Undigested fragments were settled down for one minute with normal gravity, and the supernatant was transferred to a new tube. The supernatant was passed through a 70 μm cell strainer, and the residue was washed with DMEM. The fragments remaining on the cell strainer were harvested by rinsing the inverted cell strainer with DMEM, and pelleted. The fragments mostly consist of pancreatic acinar tissue and included pancreatic ducts. The pellet was mixed with matrigel and cultured as small intestinal organoid culture system (see materials and methods of Example 1). The matrigel was incubated for five to ten minutes at 37° C. After polymerization of matrigel, 500 μl of tissue culture media (Advanced-DMEM/F12 supplemented with B27, N2, 200 ng/ml N-Acetylcysteine, 50 ng/ml EGF, 1 μg/ml R-spondin 1, 100 ng/ml Noggin, 50 or 100 ng/ml KGF (Peprotech) was added. The growth factors were added every two days. The entire medium was changed every four to six days. For passage, the organoids were removed from the Matrigel using a 1000 μA pipette and were dissociated mechanically into small fragments and transferred to fresh Matrigel. Passage was performed in 1:4 split ratio once or twice per week. Under these conditions, cultures have been maintained for at least two months.

Results

Figure 24A:
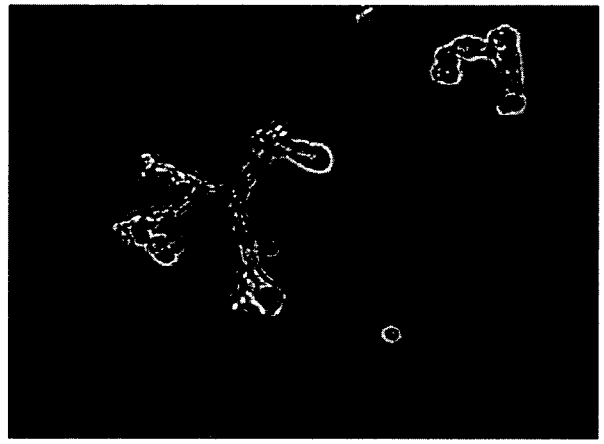
FIG. 24. Pancreatic ducts can form pancreatic-like organoids in vitro. Freshly isolated pancreatic ducts were cultured in the presence of EGF, Noggin, R-spondin-1 and KGF. Differential interference contrast images from days 0, 4 and 14 after seeding.
Figure 24B:
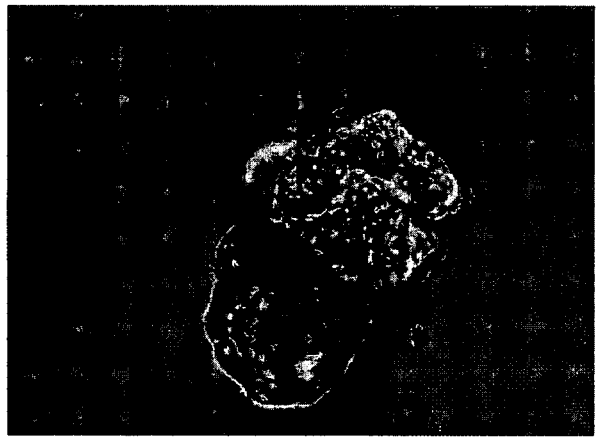
Figure 24C:
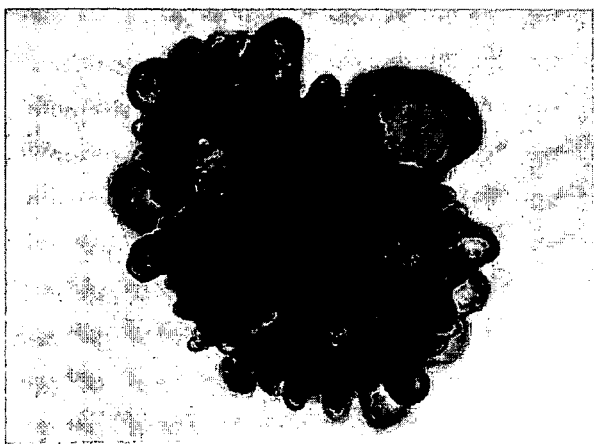

Pancreatic tissue formed simple cyst structure three to four days after culture in the presence of EGF. Noggin and R-spondin synergistically increased the size of cyst structure, but did not affect morphogenesis of organoids. KGF significantly induced budding formation as well as culture efficiency. Using the optimal combination of growth factors (EGF, Noggin, R-spondin 1 and KGF), more than 80% of pancreatic duct grew in the best combination of growth factors Once the pancreatic ducts had been taken in culture, the ducts quickly sealed both ends of the structure and form a simple structure. Approximately 20% of organoids started to form a budding structure 7 days after the start of the culture (FIG. 24). The pancreatic ducts rapidly proliferate, in contrast to the acinar tissue, which only grows very slowly.

Figure 25A:
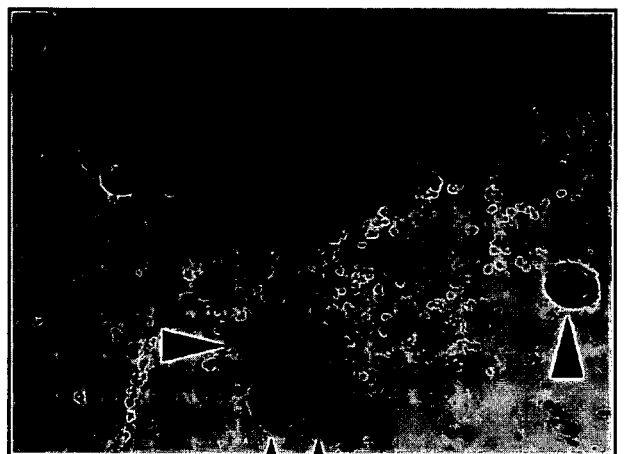
FIG. 25. Pancreatic islet-like structures form after approximately three weeks of in vitro culture. Differential interference contrast images from day 21 after seeding.
Figure 25B:
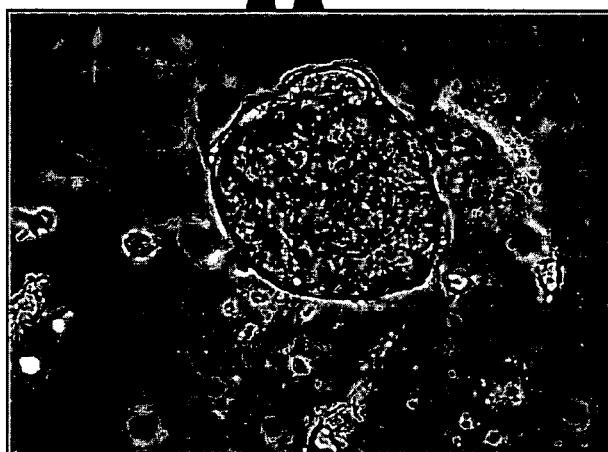
Figure 25C:
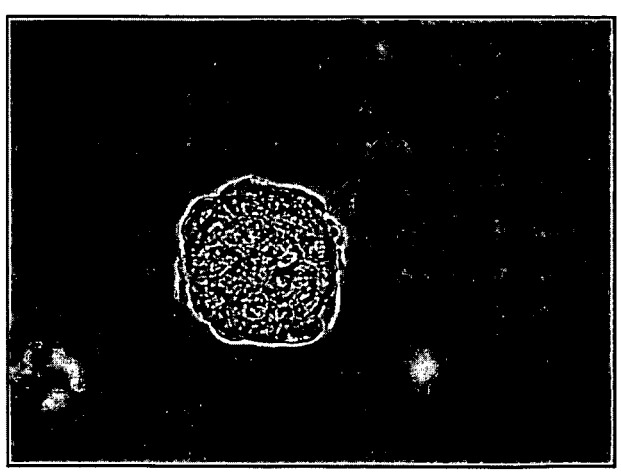

Interestingly, after passage of the organoids, approximately two to three weeks after the start of the culture, pancreatic islet-like structure were observed (FIG. 25). These islet-like structures are generally not observed before passage. The islets survive for at least seven days, but proliferate very slowly or not at all. These islet-like structures resemble the pancreatic islets of Langerhans that are present in healthy pancreas tissue. Such islets contain, among others, alpha cells and beta cells that produce glucagon and insulin, respectively. The observed islet-like structures contain cells that express insulin, neurogenin 3, and Pdx-1. Several growth factors will be tested to determine whether they increase the presence of pancreatic β cells in the organoids that are derived from pancreas tissue. Candidate growth factors comprise cyclopamine (Sonic-hedgehog inhibitor), Activin, GLP (Glucagon-like peptide) and its derivative (Exendin 4), gastrin and Nicotinamide.

Example 6b

Pancreas Organoids can be Grown In Vitro

Material and Methods

Freshly isolated pancreas was cut into small pieces, and incubated in DMEM (Invitrogen) with digestive enzyme mixture (300 U/ml Collagenase typeXI (Sigma), 0.01 mg/ml Dispase I (Roche) and 0.1 mg/ml DNase) for 10 minutes in orbital shaker (80 rpm, 37° C.). After incubation, the tissue fragments were mildly dissociated by mechanical pipetting. Undigested fragments were settled down for one minute with normal gravity. The undigested fragments were further digestive with the digestive enzyme mixture for ten minutes. This digestion procedure was repeated until the undigested fragments mostly consisted of pancreas ducts. Pancreas duct structures were manually picked up from undigested fragments under the microscopy. The pancreas ducts were mixed with matrigel and cultured as small intestinal organoid culture system (see materials and methods of Example 1). The matrigel was incubated for five to ten minutes at 37° C. After polymerization of matrigel, 500 W of tissue culture media (Advanced-DMEM/F12 supplemented with 1× Glutamax, Penicilin/Streptomycin, 10 mM Hepes, B27, N2, 10 mM N-Acetylcysteine, 10 nM [Leu$^{15}$]-Gastrin 1,100 nM Exendin4, 10 mM Nicotinamide, 50 ng/ml EGF, 1 µg/ml R-spondin 1, 100 ng/ml Noggin, 50 or 100 ng/ml FGF7 (KGF) or FGF10 (Peprotech) was added. The culture medium was changed every two days. For passage, the organoids were removed from the Matrigel using a 1000 µl pipette and were dissociated mechanically into small fragments and transferred to fresh Matrigel. Passage was performed in 1:4 split ratio once or twice per week. Under these conditions, cultures have been maintained for at least for ten months.

Results

Pancreatic tissue formed simple cyst structure three to four days after culture in the presence of EGF. Noggin and R-spondin synergistically increased the size of cyst structure, but did not affect morphogenesis of organoids. FGF7 (KGF)/FGF10 significantly induced budding formation as well as culture efficiency. Using the optimal combination of growth factors (EGF, Noggin, R-spondin-1 and FGF7 (KGF)/FGF10), more than 80% of pancreatic duct grew in the best combination of growth factors Once the pancreatic ducts had been taken in culture, the ducts quickly sealed both ends of the structure and formed a simple structure. Approximately 80% of organoids started to form a budding structure seven days after the start of the culture (FIG. 24). The pancreatic ducts rapidly proliferate, in contrast to the acinar tissue, which only grows very slowly.

Interestingly, after passage of the organoids, approximately two to three weeks after the start of the culture, pancreatic islet-like structures were observed (FIG. 25). These islet-like structures are generally not observed before passage. The islets survive for at least 14 days, but proliferate very slowly or not at all. These islet-like structures resemble the pancreatic islets of Langerhans that are present in healthy pancreas tissue. Such islets contain, among others, alpha cells and beta cells that produce glucagon and insulin, respectively. The observed islet-like structures contain cells that express insulin, neurogenin 3, and Pdx-1. Several growth factors will be tested to determine whether they increase the presence of pancreatic β cells in the organoids that are derived from pancreas tissue. Candidate growth factors comprise cyclopamine (Sonic-hedgehog inhibitor), Activin, GLP (Glucagon-like peptide) and its derivative (Exendin 4), Gastrin and Nicotinamide.

Example 7

Unimpeded Expansion of Adult Pancreatic Progenitors In Vitro by Driving a Wnt/Lgr5 Regenerative Response Materials and Methods
Mice, Reagents and Tissues Pancreatic tissue was obtained from the following mice: Axin-LacZ knock in (Lustig et al., *Mol. Cell. Biol.* 2002), Lgr5-LacZ Knockin (Barker et al., 2007), Lgr5-GFP (Barker et al., 2007). Axin-LacZ mice were injected IP with 100 µg of purified human R-spondin 1 (kindly provided by A. Abo, Nuvelo Inc., CA, USA) and sacrificed 48 hours later for LacZ expression analysis in the pancreas.

Pancreatic duct ligation was performed as described in rats (Wang et al., 1995) with some minor modifications: The experimental procedure for PDL was the following: animals are anesthetized with a mixture of fluanisone:fentanyl:midazolam injected intraperitoneally at a dosage of 3.3 mg/Kg, 0.105 mg/Kg and 1.25 mg/Kg, respectively. Animals are placed in supine position and the abdominal surface is shaved and cleaned with antiseptic solution (iodine solution). Following, a median incision at the upper anterior abdominal wall from the xiphisternum is performed and the pancreas is exposed. Under a dissecting microscope, the pancreatic splenic lobe is localized and the pancreatic duct is ligated with a 7-0 polypropylene suture monofilament at approximately 1 mm distal to the junction with the gastric lobe duct. Following surgery, the analgesic buprenorphine is administered s.c. at a dose 0.01-0.05 mg/Kg. Following, the abdominal wall and skin was closed with 5-0 silk sutures.

Freshly isolated pancreas was treated as described under Example 6, resulting in pancreatic fragments that were cultured under conditions as described below. The main pancreatic duct and first branch of ducts are mechanically isolated. The fragments were cut into small pieces and incubated in DMEM (Invitrogen) with digestive enzyme mixture (300 U/ml Collagenase type XI (Sigma), 0.01 mg/ml Dispase I (Roche) and 0.1 mg/ml DNase) for 30 minutes in orbital shaker (80 rpm, 37° C.). After the digestion, most of acinar cells were released from the fragments. Undigested fragments mostly consisting of pancreatic duct cells were settled down for one minute with normal gravity, and the supernatant was discarded. After three times washing with PBS, the undigested fragments were incubated with 2 mM EDTA/PBS for 30 minutes at room temperature. The fragments were vigorously pipetted and settled down for one minute with normal gravity. The supernatant enriched with duct cells were transferred to new tubes and washed with PBS three times. The duct cells were pelleted and mixed with the Matrigel. The matrigel was incubated for five to ten minutes at 37° C. After polymerization of matrigel, 500 µl of Expansion medium (Advanced-DMEM/F12 supplemented with 1× Glutamax, Penicillin/Streptomycin, 10 mM Hepes, B27, N2, 1 mM N-Acetylcysteine, 10 nM [Leu$^{15}$]-Gastrin 1,100 nM Exendin4, 10 mM Nicotinamide, 50 ng/ml EGF, 1 µg/ml R-spondin 1, 100 ng/ml Noggin, 50 or 100 ng/ml FGF7 (KGF) or FGF10 (Peprotech) was added. The entire medium was changed every two days. For passage, the organoids were removed from the Matrigel using a 1000 µl pipette and were dissociated mechanically into small fragments and transferred to fresh Matrigel. Passage was performed in 1:4 split ratio once per week. Under these conditions, cultures have been maintained for at least for two months. For differentiation, expansion medium were changed into differentiation medium (Advanced-DMEM/F12 supplemented with Glutamax, Penicillin/Streptomycin, 10 mM Hepes, B27, N2, 200 ng/ml N-Acetylcysteine, 10 nM [Leu$^{15}$]-Gastrin 1,100 nM Exendin4, 50 ng/ml EGF, 1 µg/ml R-spondin 1, 100 ng/ml Noggin).

FGF10 was obtained from Peprotech. BrdU was obtained from Sigma.

Q-P CR

RNA was isolated by RNA easy mini kit (Quiagen), and reverse transcribed using Moloney Murine Leukemia Virus reverse transcriptase (Promega). cDNA was amplified in a thermal cycler.

```
Primers used are shown below.
                                            (SEQ ID NO: 2)
mmTBP (forward): TATTGTATCTACCGTGAATCTTGG (SEQ ID NO: 3)
mmTBP (reverse): CAGTTGTCCGTGGCTCTC (SEQ ID NO: 4)
Lgr5 (forward) TCCAACCTCAGCGTCTTC (SEQ ID NO: 5)
Lgr5 (reverse) TGGGAATGTGTGTCAAAG
(Tm = 57° C.)
```

PCR

All primers were designed to flank or span intron sequences in order to distinguish genomic DNA.

```
Hprt
(F) AAGTTTGTTGTTGGATATGC        (SEQ ID NO: 6)

(R) CATCTTAGGCTTTGTATTTGG       (SEQ ID NO: 7)
(Tm) 57° C., 106 bp
```

```
Ngn3
(F) TCCTCGGAGCTTTTCTACGA        (SEQ ID NO: 8)

(R) TGTGTCTCTGGGGACACTTG        (SEQ ID NO: 9)
(Tm) 60° C., 239 bp/373 bp (genomic band)

Pax6
(F) AACAACCTGCCTATGCAACC        (SEQ ID NO: 10)

(R) ACTTGGACGGGAACTGACAC        (SEQ ID NO: 11)
TM 60° C., 206 bp

Glucokinase
(F) AAGATCATTGGCGGAAAG          (SEQ ID NO: 12)

(R) GAGTGCTCAGGATGTTAAG         (SEQ ID NO: 13)
(Tm) 57° C. 193 bp

Chromogranin A
(F) GCTGACAGCAGAGAAGCGGCT       (SEQ ID NO: 14)

(R) GACAGGCTCTCTAGCTCCTGG       (SEQ ID NO: 15)
(Tm) 60° C. 231 bp

Glut2 (slc2a2)
(F) AAGTTGGAAGAGGAAGTCAG        (SEQ ID NO: 16)

(R) AGACCTTCTGCTCAGTCG          (SEQ ID NO: 17)
(Tm) 57° C. 124 bp

Insulin
(F) TTTGTCAAGCAGCACCTTTG        (SEQ ID NO: 18)

(R) TCTACAATGCCACGCTTCTG        (SEQ ID NO: 19)
(Tm) 57° C., 214 bp

Somatostatin
(F) GAGGCAAGGAAGATGCTGTC        (SEQ ID NO: 20)

(R) GGGCATCATTCTCTGTCTGG        (SEQ ID NO: 21)
(Tm) 57° C., 214 bp

Glucagon
(F) TTACTTTGTGGCTGGATTGCTT      (SEQ ID NO: 22)

(R) AGTGGCGTTTGTCTTCATTCA       (SEQ ID NO: 23)
(Tm) 57° C., 149 bp
```

Image Analysis

The images of crypt organoids were taken by either confocal microscopy with a Leica SP5, an inverted microscope (Nikon DM-IL) or a stereomicroscope (Leica, MZ16-FA). For immunohistochemistry, samples were fixed with 4% paraformaldehyde (PFA) for one hour at room temperature, and paraffin sections were processed with standard techniques (Barker et al., *Nature* 2007). Immunohistochemistry was performed as described previously (Barker et al., *Nature* 2007). For whole-mount immunostaining, pancreas organoids were isolated from Matrigel using Dispase (Invitrogen), and fixed with 4% PFA, followed by permeabilization with 0.1% Triton X-100. Following antibodies were used for immunohistochemistry; anti-BrdU (Amersham), anti-Ki67 (Dako), anti-Insulin (Sigma), anti-C-peptide (Cell signaling), anti-Ngn3 (Developmental hybridoma studies bank).

DNA was stained with DAPI or ToPro-3 (Molecular Probes). Three-dimensional images were acquired with confocal microscopy. The staining with X-gal was performed as described under Example 5 under immunohistochemistry and imaging analysis.

FACS

Pancreatic organoids were cultured in the presence or absence of R-spondin (1 µg/ml) were removed from matrigel mechanically or enzymatically (TrypLE). Isolated organoids were further digested by TrypLE for ten minutes at 37 C.

Dissociated cells were passed through a 40-1.1m cell strainer (BD bioscience) and stained with APC conjugated anti-Ep-CAM (eBioscience). LacZ was stained by FluoReporter kit (Invitrogen) following manufacturer's protocol. Single viable cells were gated with pulse-width, side scatter parameter and propidium iodide staining.

In Vitro Expansion of Single Axin2-LacZ-Positive Pancreatic Cells

Pancreas was isolated from mice seven days after PDL treatment, and pancreas ducts were isolated as described above. Isolated pancreas ducts were incubated with TrypLE Express (Invitrogen) for 20 minutes at 37° C., followed by passing through 40 μm cell strainer (BD bioscience). Cells were stained with EpCAM-APC and fluorescent substrate for LacZ (FluoroReporter kit) as described in Example 7. Cells were analyzed and single viable epithelial cells were sorted by flow cytometer (MoFlo; Dako Cytomation), and collected in the EM medium. Sorted cells were pelleted, mixed with Matrigel and cultured with EM medium including 50% Wnt-conditioned medium and 10 mM Y-27632 for four days. Culture medium was changed into EM medium without Wnt and Y-27632 after four days.

Results

Single Wnt-dependent Lgr5$^+$ stem cells derived from the small intestine can be cultured to faun continuously expanding gut-like organoids (Sato et al., 2009). In healthy adult pancreas, the Wnt pathway is inactive and, consequently, Lgr5 is not expressed. Upon injury by partial duct ligation (PDL), we find that the Wnt pathway becomes robustly activated, while Lgr5 expression appears at the buds of regenerating ducts. Under conditions modified from the intestinal culture system, freshly isolated adult duct fragments initiate expression of Lgr5 and form budding cysts which expand ten-fold weekly for >30 weeks. Removal of growth stimuli converts these cysts into structures with immature islet morphology, expressing endocrine and B-cell markers. Single Wnt-stimulated cells from injured pancreas can also initiate these long-term cultures. We conclude that the Hayflick limit does not apply to adult progenitor cells when cultured under optimized conditions. Thus, culture methods favoring expansion of organ-specific adult stem cells may represent an alternative to ES– or iPS-based tissue generation.

While development of the exocrine and endocrine compartments of the embryonic pancreas are understood in great detail (Jensen, 2004), much less is known about the generation of islet cells in the postnatal pancreas (Bonner-Weir and Weir, 2005; Bouwens and Rooman, 2005). Genetic lineage tracing has provided proof that pre-existing β cells, rather than stem/progenitor cells, generate new β cells in adult mice, both under normal physiological conditions and after partial pancreatectomy (Dor et al., 2004; Teta et al., 2007). The existence of multipotent progenitor cells in the ductal lining of the pancreas of adult mice has been recently described, which can be activated in injured pancreas to increase the functional β cell mass (Xu et al., 2008). Controlled injury was obtained by performing PDL on the pancreas of adult mice carrying a promoter reporter of Ngn3, which encodes a master switch for embryonic islet cell progenitors (Apelqvist et al., 1999; Gradwohl et al., 2000; Gu et al., 2002; Schwitzgebel et al., 2000) and which is silent in normal postnatal pancreas (Gu et al., 2002). Differentiation of these β cell progenitors is Ngn3-dependent and gives rise to all islet cell types, including glucose-responsive β cells (Xu et al., 2008). It is currently not known which signals drive the appearance of these progenitors upon injury. Such insights appear important as they may guide the design of in vitro approaches to progenitor expansion.

Figure 26A:
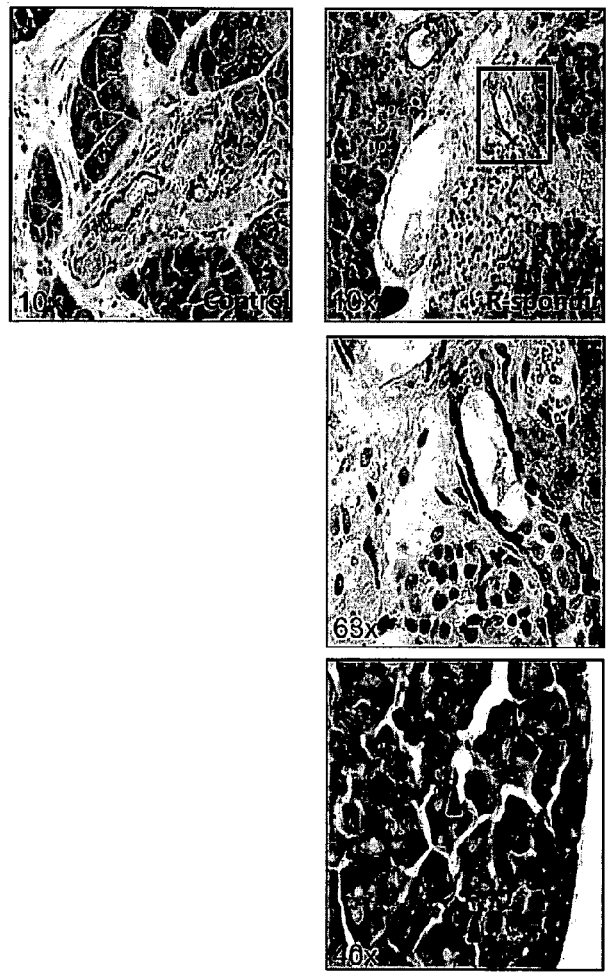
FIG. 26. Axin-LacZ mice were injected with vehicle alone (FIG. 26a, left panel) or R-spondin (FIG. 26a, right top panel). After two days, the pancreas was isolated and the presence of LacZ expression was determined by staining with X-gal. The middle right panel of A shows a larger magnification of a duct that shows positive staining for LacZ, indicating the expression of Axin-LacZ along the lining of the pancreatic duct. The bottom panel shows that small duct cells in centroacinar or intercalated duct cells expressed Axin2-LacZ (examples of which are indicated by black arrows). Magnifications are shown in the corner of each image. Pancreatic duct ligation was performed in wild-type mice. At different times after PDL, the pancreas was isolated and tissue sections obtained from the PDL and non-PDL area were stained with H&E. Magnifications are shown for each time point (FIG. 26c). Pancreatic duct ligation was performed in wt and Axin2-LacZ mice. Seven days after PDL, the pancreas was isolated and Axin2-LacZ expression was determined by staining with X-gal of fixed tissue sections (FIG. 26d) or whole mounted organ fragments (FIG. 26e). The white circles indicate ligated portion of the pancreas. Expression of Ki67 (examples indicated by arrows) in pancreas tissue sections five days after PDL. Magnifications are shown (FIG. 26f). Incorporation of BrdU (examples indicated by arrows) in pancreas tissue two days after in vivo treatment with R-spondin. Magnifications are shown (FIG. 26g). Lgr5 mRNA expression was determined by Q-PCR in pancreas tissue obtained from mice undergoing PDL or a sham operation. In the PDL pancreas, the PDL area and non-PDL area was subjected to Q-PCR. The fold increase of Lgr5 expression compared to TATA box binding protein (tbp), a housekeeping gene, is shown (FIG. 26h). Thirteen days after PDL, the pancreas was isolated and Lgr5-LacZ expression was determined by staining with X-gal of fixed tissue sections. Examples of stained cells are indicated by black arrows (FIG. 26i).
Figure 26C:
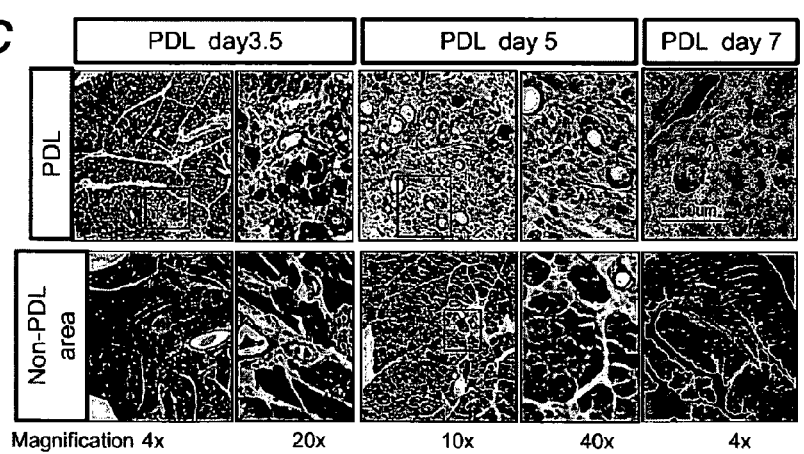
Figure 26D:
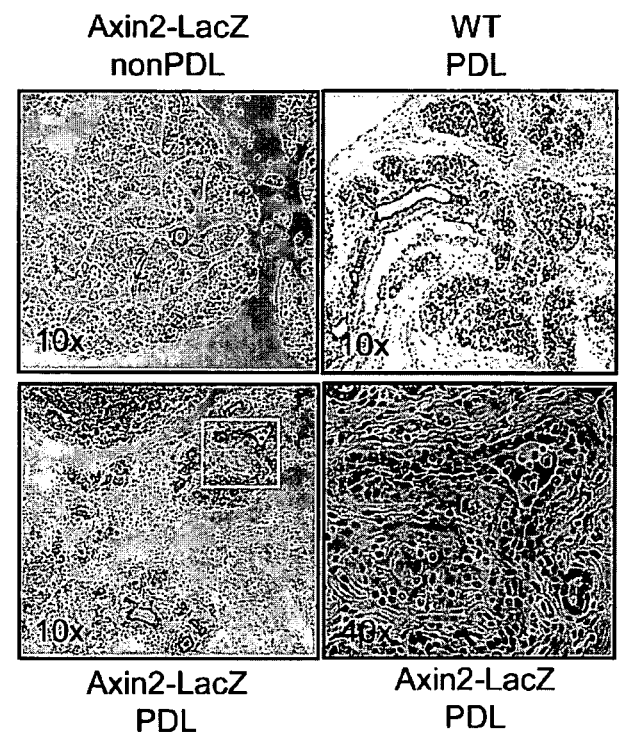
Figure 26E:
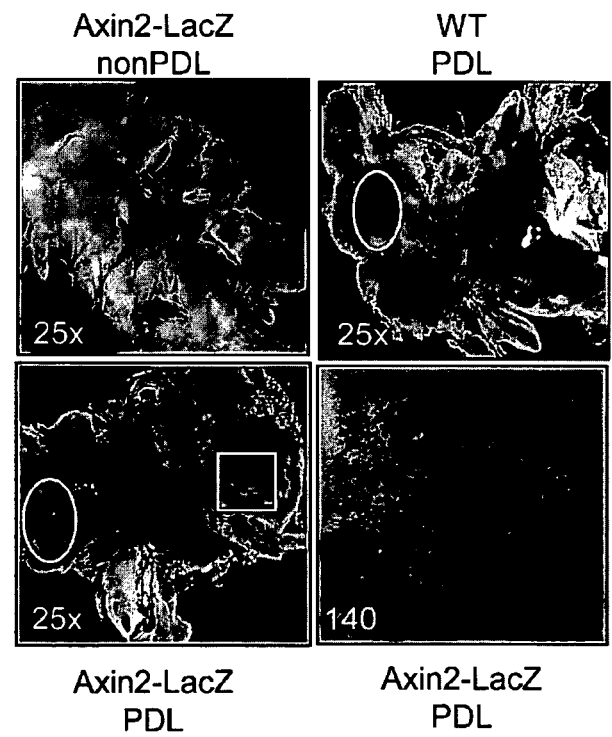
Figure 26F:
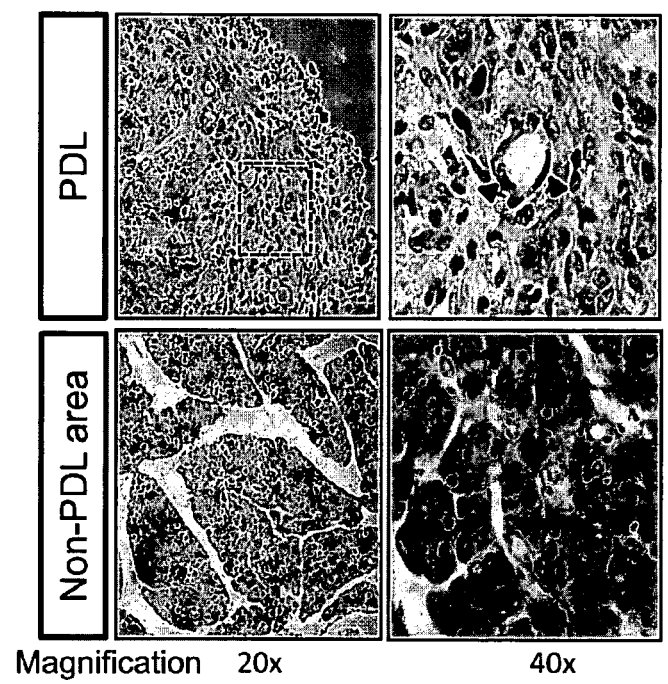
Figure 26G:
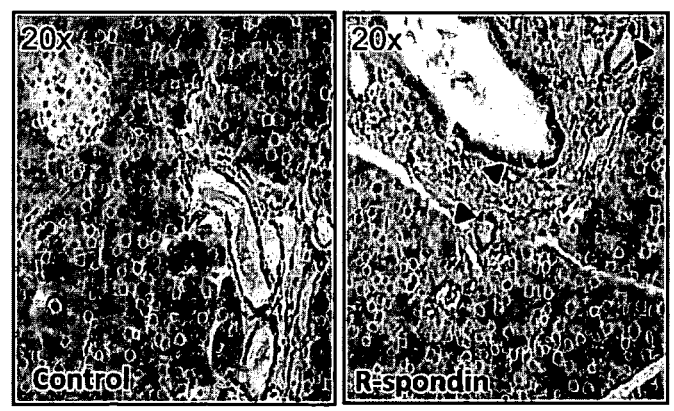

To determine whether Wnt signaling plays a role in the induction of β cell progenitors, the expression of the Axin2-LacZ allele was followed in the adult pancreas. The Axin2-LacZ allele has proven to represent a faithful, general reporter for Wnt signaling (Lustig et al., *Mol. Cell. Biol.* 2002). As expected, the reporter was inactive in adult pancreas (FIG. 26*a*). However, when we injected the Wnt agonist Rspo1 (Kim et al, 2005) into Axin2-LacZ mice to activate the Wnt signaling pathway, we noticed the presence of Wnt-responsive cells along the ducts, but not in acini or islets of the pancreas (FIG. 26*b*). Since β cell progenitors have previously been detected only upon injury of the pancreas, we then tested if a Wnt response was physiologically activated in these cells upon injury by performing PDL. FIG. 26*c* shows H&E staining of pancreas tissue sections isolated from the PDL and non-PDL area. As has been reported previously (Abe et al., 1995), the acinar cells become apoptotic after five days and are replaced by newly formed duct structures by a mechanism not completely understood. After seven days, an increase in islet number (islet neogenesis) as well and in islet size is also observed (as indicated by an asterisk). This indicates that the PDL was successful. Indeed, the Axin2-LacZ reporter was specifically activated along the ducts of the ligated part of the pancreas, while the unligated part did not show this response (FIGS. 26*d* and 26*e*). Moreover, the proliferative response, as determined by Ki67 staining, was mostly restricted to the ducts of the ligated part, whereas in ducts of the unligated part, no nuclear Ki67 could be detected (FIG. 26*f*). This resembled the detection of proliferative, BrdU-positive cells in the pancreas after treatment with R-spondin (FIG. 26*g*).

Figure 26H:
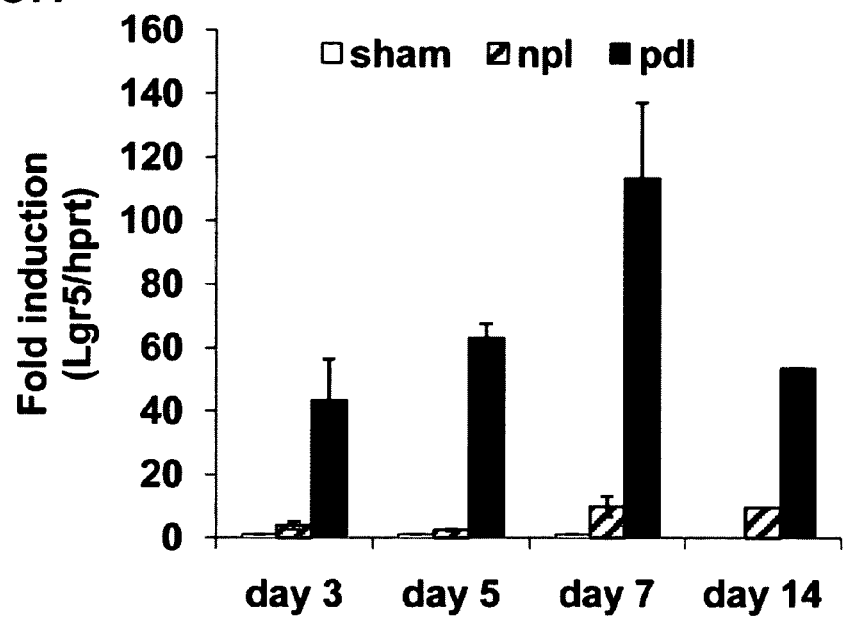
Figure 26I:
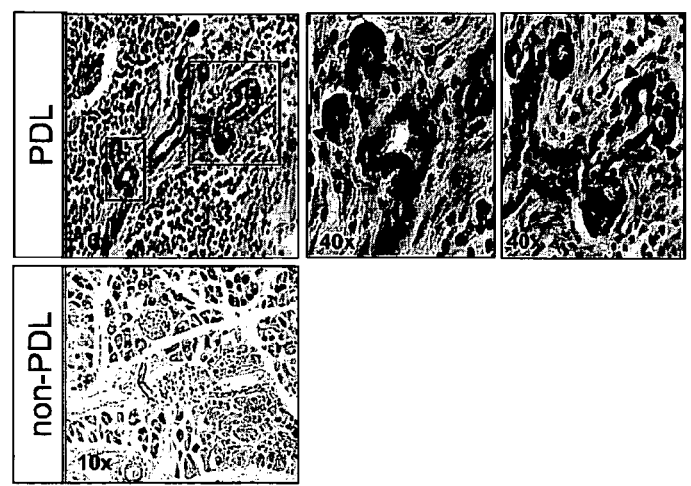

We have previously shown in the intestines that a certain population of Wnt responsive cells are stem cells (Barker et al., 2007). A marker for that population of cells was Lgr5. The Lgr5 gene is, like Axin2, a Wnt-responsive gene. Yet in the intestine and the skin it is only expressed in Wnt-stimulated stem cells but not in transit amplifying cells (Barker et al., 2007; Jaks et al., 2008)). It is, therefore, considered to be a genuine stem cell marker. We hypothesized that, similar to the Lgr5+ cells in the intestines, Lgr5+ cells in the pancreas may also be the origin of the β cell progenitors as detected after injury. To test this hypothesis, we performed PDL in the pancreas of Axin-LacZ and Lgr5-LacZ mice and determined Lgr5 mRNA expression and LacZ staining. Interestingly, Lgr5 became readily detectable by qPCR in a post-PDL time course (FIG. 26*h*). Moreover, PDL in Lgr5-LacZ knockin mice resulted in specific activity of the reporter in the buds of regenerating ducts (indicated by the asterisk), as demonstrated by X-gal staining (FIG. 26*i*). The appearance of Lgr5 expression at sites of active regeneration suggested that Lgr5 might not only mark stem cells in physiological self-renewal (e.g., in the intestine, stomach or hair follicle), but that its expression may also herald the activation by Wnt of regenerative stem cells/progenitors upon injury.

Given the appearance of the Wnt-dependent Lgr5 stem cell marker, we reasoned that adult pancreas progenitors may by expanded in the previously defined gut organoid culture conditions (Sato et al., 2009). Cultures of heterogeneous populations of pancreas cells have been previously established and typically include growth factors such as EGF (Githens et al., *In Vitro Cell Dev. Biol.* 1989), FGF10 (Miralles et al., *Proc. Natl. Acad. Sci. U.S.A.* 1999) and HGF (Lefebvre et al., *Diabetes* 1998; Suzuki et al., *Diabetes* 53, 2004) and serum supplements such as Gastrin (Rooman et al., *Gastroenterology* 2001), Nicotinamide (Rooman et al., *Diabetologia* 2000) and others. A number of such cultures resulted in the in vitro generation of cells with β cell-like phenotypes (Bonner-Weir et al., 2000; Seaberg et al., 2004; Suzuki et al., 2004) that under certain conditions were able to reverse hyperglycemia when transplanted in diabetic mice (Hao et al., 2006; Ramiya et al., 2000). Most of these approaches start with mixed cell populations that undergo senescence over time. It appears fair to say that no robust, long-term culture system exists today that maintains robust expansion of defined, non-transformed adult pancreas progenitors over long periods of time that maintain the capacity to differentiate along the endocrine lineage.

Figure 27A:
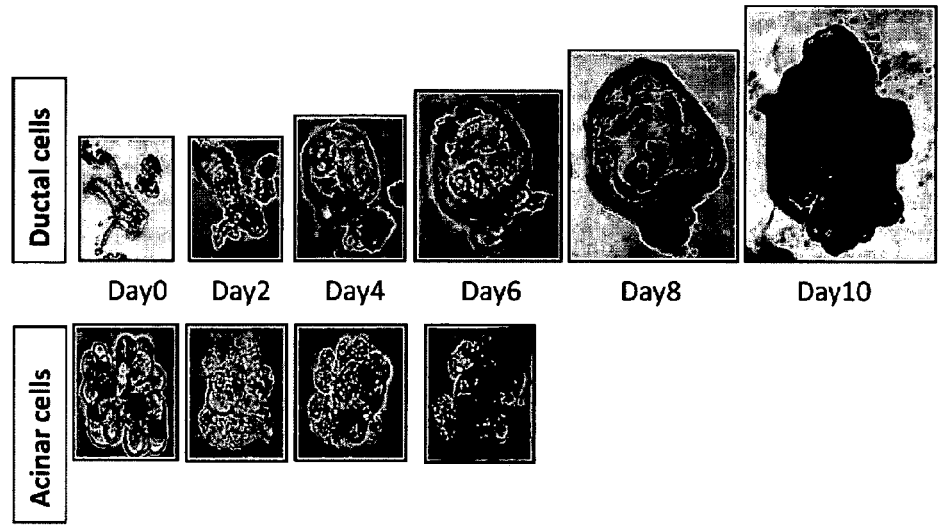
FIG. 27. Images of pancreatic ductal fragments grown in vitro in EM taken at different time points after isolated from a wild-type mouse (FIG. 27a, top panel). Centroacinar cells did not grow for periods longer than seven days, after which they disintegrated (FIG. 27a, bottom panel). Pancreatic fragments were grown in the presence or absence of EGF (50 ng/ml), R-spondin (1 µg/ml), FGF10 (100 ng/ml) or Noggin (100 ng/ml). Images of the cultures were taken seven and fourteen days after the start of the culture with freshly isolated pancreatic fragments. Cultures without EGF did not survive for longer than ten days (FIG. 27b). Pancreatic fragments isolated from Axin2-LacZ mice were cultured in the absence or presence of R-spondin (1 µg/ml) for three days. X-gal staining showed expression of Wnt-responsive Axin-LacZ in the ductal cells after three and fourteen days only in the presence of R-spondin (examples indicated by white arrows). No X-gal staining was detected in the acinar or islet cells (FIG. 27c). Ductal fragments were isolated from Lgr5-LacZ mice and cultured for three days in the absence or presence of R-spondin. Expression of Lgr5-LacZ, as indicated by X-gal staining, shows Lgr5+ cells on the tips of the buds, similar to its expression after PDL (FIG. 27d). FACS staining of cells obtained from pancreatic fragments cultured in the presence of a Wnt agonist, R-spondin. Cells were stained for EpCAM, a pan-epithelial cell marker, and LacZ (Fluorescein-di-galactopyranoside, FDG). The percentage of Lgr5+ cells is significantly increased when pancreatic fragments are cultured in the presence of a Wnt signal (FIG. 27e).
Figure 27B:
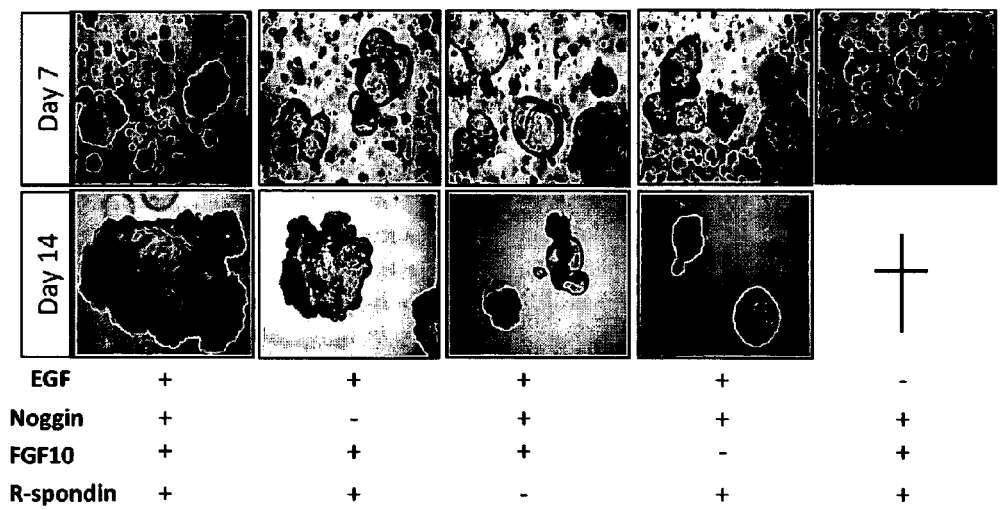

We first attempted to grow purified duct fragments in Expansion Medium (EM). As shown in FIG. 27a, small duct fragments immediately underwent expansion into cyst-like structures undergoing continuous budding, while islets (data not shown) and acini (bottom panel) gradually disintegrated. The cultures expand ten-fold/week (and are passaged weekly) for over 30 weeks. Multiple growth factors have been tested to determine the required signals for optimal expansion of pancreatic cells in vitro (FIG. 27b). Clearly, in the absence of EGF, cultures disintegrated after seven days. Also the absence of R-spondin or FGF10 reduced the viability of the cultures after 14 days. In contrast, Noggin, a BMP inhibitor, did not have any effect on the sustained growth of pancreatic fragments. The addition of Nicotinamide, Exendin4, Gastrin to the expansion medium was not essential but resulted in an increase in culture efficiency (data not shown).

Figure 27C:
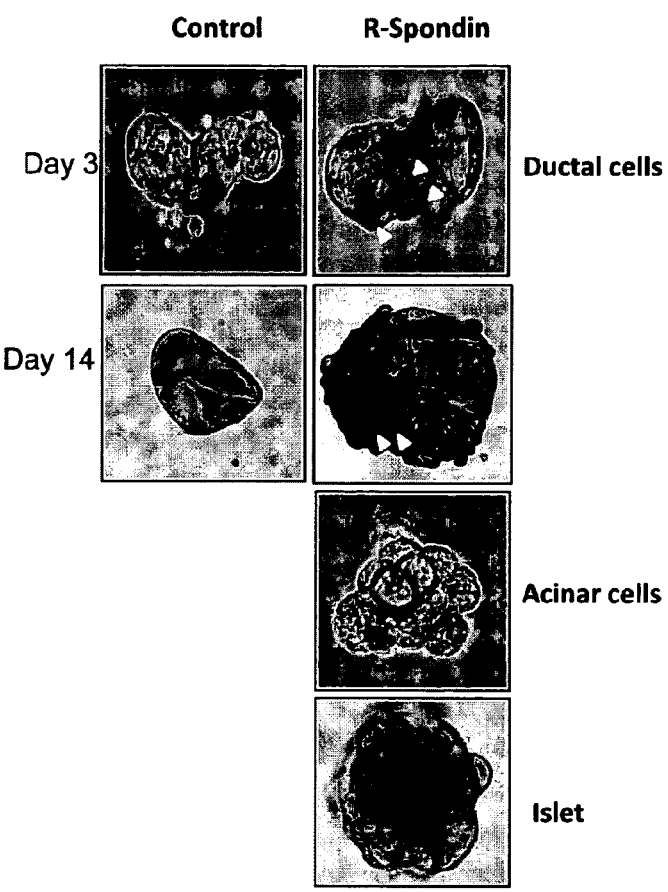
Figure 27D:
Figure 27E:
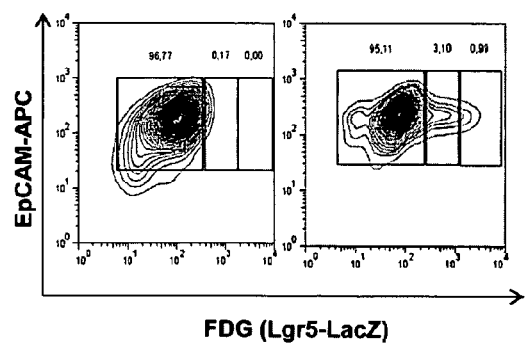

Since we demonstrated that Wnt signaling was activated upon PDL, the effect of addition of a Wnt agonist to freshly isolated pancreatic fragments in vitro on sustained growth was determined. When ducts were isolated from Axin2-LacZ mice, the entire budding cysts stained blue only in the presence of the Wnt agonist R-spondin 1 (FIG. 27c), resembling the situation in vivo after PDL (FIGS. 26d and 26e). No blue staining was observed in freshly isolated islets or acini from Axin2-LacZ pancreas. In line with the in vivo observations upon PDL, only the buds of Lgr5-LacZ cysts stained blue (FIG. 27d). Moreover, culturing of pancreatic Lgr5-LacZ organoids for 14 days in the presence of R-spondin increased the percentage of Lgr5+ cells significantly (FIG. 27e). Importantly, when pancreatic fragments were cultured in the absence of R-spondin in EM, organoids cease to proliferate within one month, whereas in the presence of R-spondin, they can be expanded for an unlimited time period. These observations imply that Wnt-responsive progenitors located near ducts fueled the growth of the budding cysts, which were subsequently maintained by Lgr5-expressing cells with stem cell-like properties.

Figure 28:
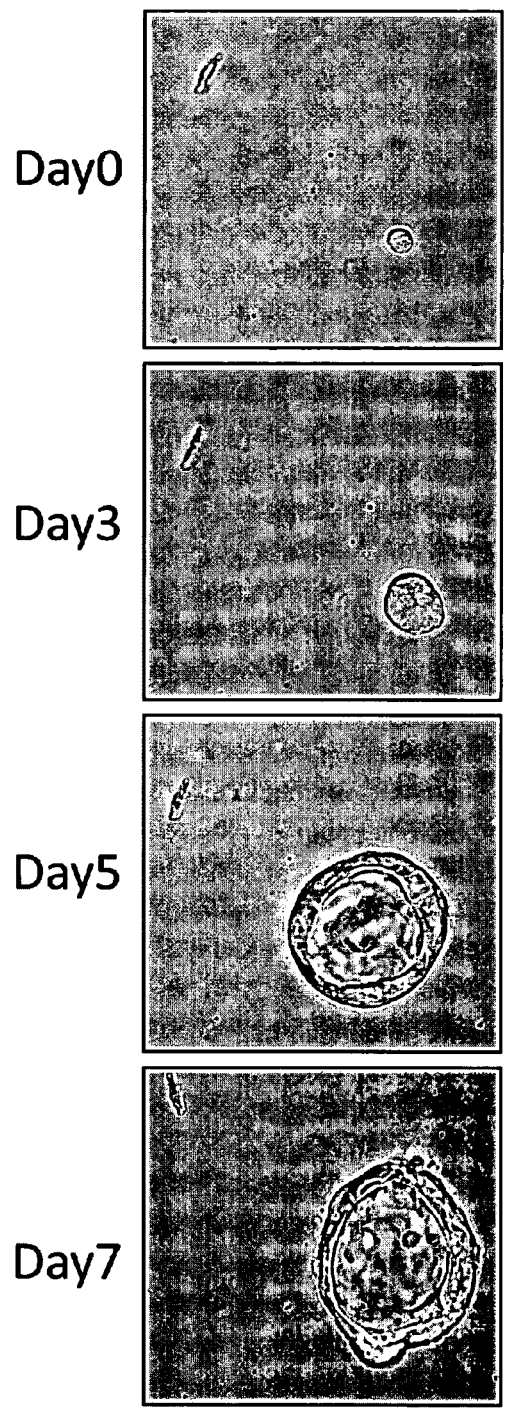
FIG. 28. Pancreas was isolated from mice seven days after PDL treatment and pancreatic cells were stained with EpCAM-APC and fluorescent substrate for LacZ (FluoroReporter kit), sorted and cultured in EM including 50% Wnt3A-conditioned medium and 10 mM Y-27632 for four days. Culture medium was changed into EM medium without Wnt and Y-27632 after four days. Pictures were taken on the indicated days and a 40× magnification is shown.

To test this notion directly, we sorted Axin2-LacZ-positive cells from mice seven days post PDL and found that these cells efficiently initiated budding cysts that were indistinguishable from duct-initiated cysts (FIG. 28). The single cells require the presence of Wnt3a in the medium. Comparison of culture efficiency in the presence of absence of Wnt3A after single cell dissociation showed that the single cells cultured in the absence of Wnt3A initially grow as small cyst structures, but stop proliferation after two to four days. This is not the case for pancreas cultures started from isolated pancreas fragments. Interestingly, the Wnt3A could be removed after four days, indicating that either this signal was no longer necessary to stimulate growth or that the production of Wnt3A was initiated by cells derived from the single sorted cells the culture had started with.

Figure 29A:
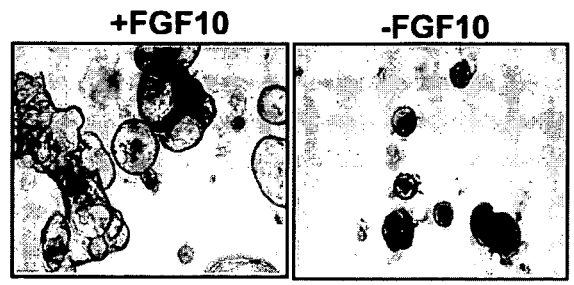
FIG. 29. Pancreatic organoids were transferred from EM to DM. The effect of removal of FGF 10 from the expansion medium, resulting in DM, induced differentiation into islets. Pancreatic organoids were cultured for ten days in DM after which islet-like structures could be detected in vitro. Pictures of the cultures in the presence and absence of FGF10 are shown (FIG. 29a) and shows increased expression of certain differentiation markers, Ngn3 and somatostatin as measured by PCR. Hprt is a housekeeping gene (FIG. 29b). At several time points after the transfer to DM, expression of a number of markers was assessed by PCR (FIG. 29c). Change in morphology from pancreatic cysts to β cell-like structures (FIG. 29d) accompanied the appearance of certain β cell markers, such as Insulin and C-peptide as detected by immunofluorescence (FIG. 29e). The presence of R-spondin in DM is essential for the regeneration of β cell progenitors, as indicated by positive immunofluorescent staining for Ngn3 (examples are indicated by white arrows) (FIG. 29f).
Figure 29B:
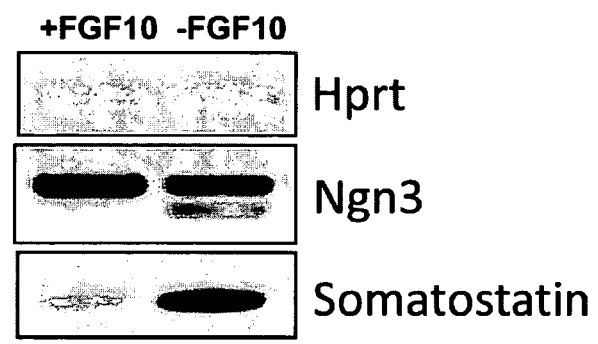
Figure 29E:
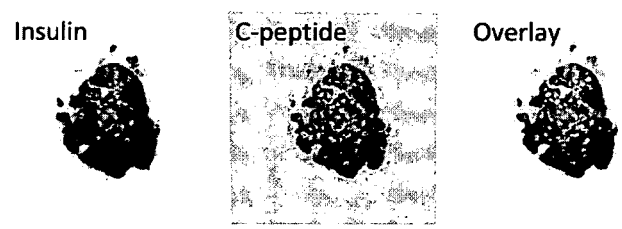
Figure 29F:
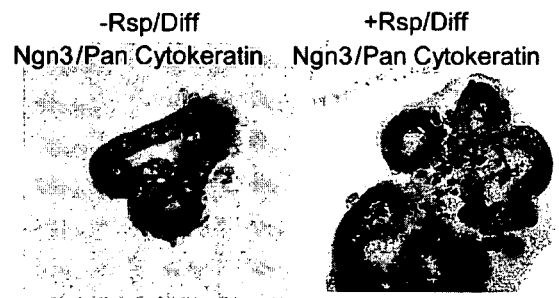
Figure 29C:
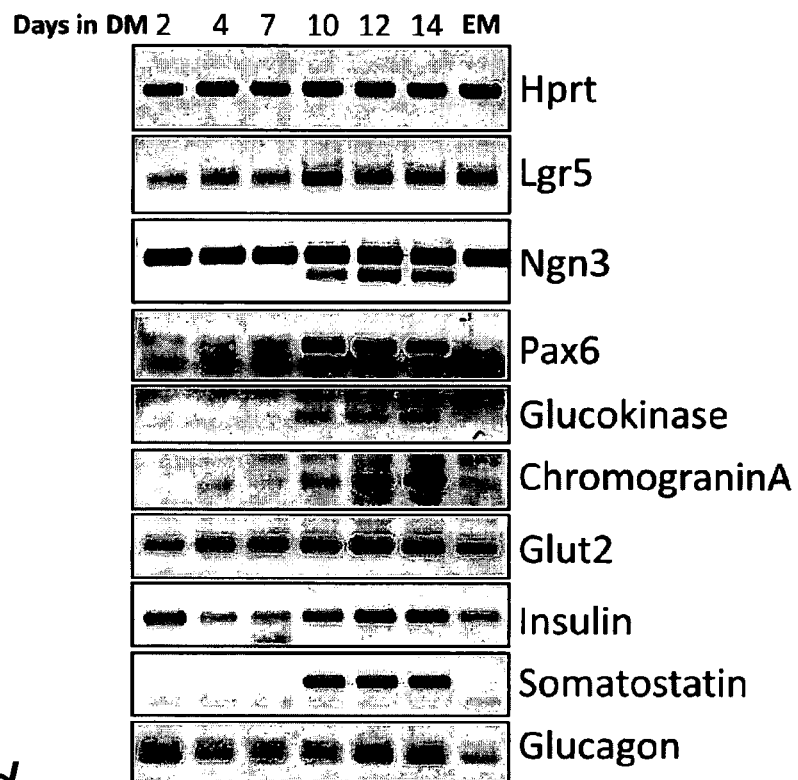

We then attempted to assess the potential of the budding cysts to generate endocrine lineage cells. To this end, we tested a number of changes to the EM to define a Differentiation Medium (DM). A series of factors was tested for their effect on the differentiation into the endocrine lineages. The removal of FGF10 seemed to be crucial to the induction of differentiation. Only in the absence of FGF10 did the islet-like structures appear (FIG. 29a), which corresponded with the expression of several differentiation markers for β cell progenitors (Ngn3), β cells (Insulin), glucagon (α cells) and somatostatin (δ cells) appear (FIGS. 29b and 29c). Moreover, differentiation markers, such as Glucokinase, Pax6 and Chromogranin A were up-regulated starting ten days after exposure to the DM medium. Therefore, DM optimally consisted of at least EGF and R-spondin and did not have any FGF7 or FGF10 present. The sustained expression of Lgr5, a stem cell marker, under differentiation conditions can be explained by the presence of R-spondin, a Wnt agonist, in DM, since Lgr5 is a Wnt responsive gene. When cells were cultured in presence of Nicotinamide in EM, it was also important to remove this from the medium as well to obtain full differentiation.

Figure 29D:
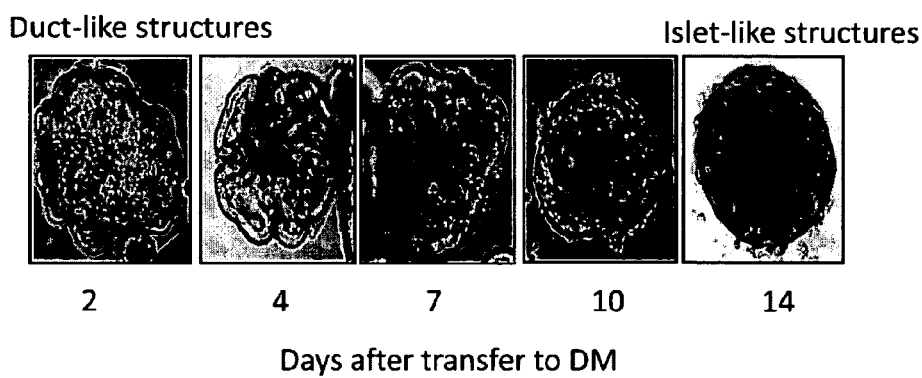

When budding cysts after any period of culture were transferred from EM to DM, the cysts underwent a stereotypic "involution" process: progressive inward folding of the wall lead to impaction of the cyst into a smaller compact body with morphological resemblance to an islet (FIG. 29d). Islet-like morphology was confirmed by markers for p cell islets such as Insulin and C-peptide (FIG. 29e). To confirm the dependence of this step of the regeneration process on Wnt signaling, pancreatic fragments were cultured in DM in the absence or presence of R-spondin. Importantly, β cell progenitors, as demonstrated by expression of Ngn3, were only detectable in the presence of R-spondin (FIG. 29f).

Example 8

In Vitro Expansion of Human Pancreas Fragments

During embryonic pancreas development, neurogenin3+ or insulin-expressing cells were seen in the pancreas ductal network, and it was suggested that pancreas duct cells give rise to endocrine progenitors and consequently mature endocrine cells. It has been shown that human pancreas duct cells differentiate into glucose-responsive insulin-producing cells in vitro (S. Bonner-Weir et al. 2000 *PNAS*), and this finding made pancreas duct cells an attractive source for beta cells replacement therapy. However, it has been difficult to expand duct cells without losing endocrine differentiation capacity. In the previously reported culture system, human pancreas duct cells lost epithelial property or underwent senescence after two weeks and up to five weeks (B. Trautmann et al., *Pancreas* vol. 8 248-254). Therefore, there is no robust culture system to expand human pancreas duct cells, which retain endocrine differentiation ability. Taking advantage of establishment of mouse pancreas organoid culture system, here, we attempted to establish human pancreas organoid culture system.

Growth of Human Pancreatic Progenitors In Vitro

Figure 30:
FIG. 30. Human pancreas fragments were freshly isolated and cultured in EM. Pictures were taken of the cultures at the indicated time points after the start of the culture.
Figure 30:
Figure 30:
Figure 30:
Figure 30:
Figure 30:
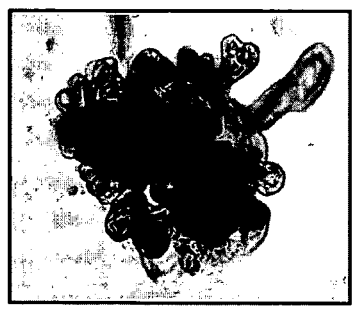

Human pancreas was obtained from Leiden University Medical Center, The Netherlands. Importantly, under the same conditions as described for mouse pancreas fragments above (Example 7), freshly isolated human pancreas fragments can also be grown in vitro (FIG. 30).

Under these expansion conditions, the culture efficiency of the pancreatic fragments was approximately 80%, meaning that 80% of the freshly isolated pancreatic fragments were efficiently expanded in vitro for a longer period of time. As compared with mouse pancreas, acinar tissue more easily forms cyst structures; however, these structures ceased to proliferate within four weeks. Pancreas duct cells from larger ductular network more efficiently produce cyst structures and eventually form organoids with bud. The pancreas organoids were split 1:5 ratio once per week and maintained in vitro at least five weeks without losing proliferation ability.

In summary, we established human pancreas organoids culture system and succeeded in expansion of pancreas duct cells at least 3000 times from original volume. We are optimizing endocrine differentiation culture condition for human pancreas duct cells, and this in vitro approach, once optimized, might have important implications for making beta cell replacement therapy available to a larger number of people with type 1 and type 2 diabetes mellitus.

REFERENCES

Abe K. and S. Watanabe (1995). Apoptosis of mouse pancreatic acinar cells after duct ligation. *Arch. Histol. Cytol.* 58:221-9.

Apelqvist A., H. Li, L. Sommer, P. Beatus, D. J. Anderson, T. Honjo, M. Hrabe de Angelis, U. Lendahl, and H. Edlund (1999). Notch signaling controls pancreatic cell differentiation. *Nature* 400:877-81.

Barker N., J. H. van Es, J. Kuipers, P. Kujala, M. van den Born, M. Cozijnsen, A. Haegebarth, J. Korving, H. Begthel, P. J. Peters, and H. Clevers (2007). Identification of stem cells in small intestine and colon by marker gene Lgr5. *Nature* 449:1003-7.

Bonner-Weir S, and G. C. Weir (2005). New sources of pancreatic beta-cells. *Nat. Biotechnol.* 23:857-861.

Bonner-Weir S., M. Taneja, G. C. Weir, K. Tatarkiewicz, K. H. Song, A. Sharma and J. J. O'Neil (2000). In vitro cultivation of human islets from expanded ductal tissue. *Proc. Natl. Acad. Sci. U.S.A.* 97:7999-8004.

Bouwens L. and I. Rooman (2005). Regulation of pancreatic beta-cell mass. *Physiol. Rev.* 85:1255-1270.

Dor Y., J. Brown, O. I. Martinez and D. A. Melton (2004). Adult pancreatic beta cells are formed by self-duplication rather than stem-cell differentiation. *Nature* 429:41-46.

Githens S., J. A. Schexnayder, K. Desai, and C. L. Patke (1989). Rat pancreatic interlobular duct epithelium: isolation and culture in collagen gel. *In Vitro Cell Dev. Biol.* 25:679-88.

Gradwohl G., A. Dierich, M. LeMeur and F. Guillemot (2000). Neurogenin3 is required for the development of the four endocrine cell lineages of the pancreas. *Proc. Natl. Acad. Sci. U.S.A.* 97:1607-1611.

Gu G., J. Dubauskaite and D. A. Melton (2002). Direct evidence for the pancreatic lineage: NGN3+ cells are islet progenitors and are distinct from duct progenitors. *Development* 129:2447-2457.

Hao E., B. Tyrberg, P. Itkin-Ansari, J. R. Lakey, I. Geron, E. Z. Monosov, M. Barcova, M. Mercola and F. Levine (2006). Beta-cell differentiation from nonendocrine epithelial cells of the adult human pancreas. *Nat. Med.* 12:310-316.

Jaks V., N. Barker, M. Kasper, J. H. van Es, H. J. Snippert, H. Clevers, and R. Toftgård (2008). Lgr5 marks cycling, yet long-lived, hair follicle stem cells. *Nat. Genet.* 40:1291-9.

Lefebvre V. H., T. Otonkoski, J. Ustinov, M. A. Huotari, D. G. Pipeleers, and L. Bouwens (1998). Culture of adult human islet preparations with hepatocyte growth factor and 804G matrix is mitogenic for duct cells but not for beta-cells. *Diabetes* 47:134-7.

Lustig B., B. Jerchow, M. Sachs, S. Weiler, T. Pietsch, U. Karsten, M. van de Wetering, H. Clevers, P. M. Schlag, W. Birchmeier and J. Behrens (2002). Negative feedback loop of Wnt signaling through up-regulation of conductin/axin2 in colorectal and liver tumors. *J. Mol. Cell Biol.* 1184-93.

Miralles F., P. Czernichow, K. Ozaki, N. Itoh, and R. Scharfmann (1999). Signaling through fibroblast growth factor receptor 2b plays a key role in the development of the exocrine pancreas. *Proc. Natl. Acad. Sci. U.S.A.* 96:6267-72.

Ramiya V. K., M. Maraist, K. E. Arfors, D. A. Schatz, A. B. Peck, and J. G. Cornelius (2000). Reversal of insulin-dependent diabetes using islets generated in vitro from pancreatic stem cells. *Nat. Med.* 6:278-282.

Rooman I., Y. Heremans, H. Heimberg, L. Bouwens (2000). Modulation of rat pancreatic acinoductal transdifferentiation and expression of PDX-1 in vitro. *Diabetologia* 2000 July; 43(7):907-14.

Rooman I., J. Lardon, D. Flamez, F. Schuit, L. Bouwens (2001). Mitogenic effect of gastrin and expression of gastrin receptors in duct-like cells of rat pancreas. *Gastroenterology* 121:940-9.

Sato T., R. G. Vries, H. J. Snippert, M. van de Wetering, N. Barker, D. E. Stange, J. H. van Es, A. Abo, P. Kujala, P. J. Peters, H. Clevers (2009). Single Lgr5 stem cells build crypt-villus structures in vitro without a mesenchymal niche. *Nature* 459:262-5.

Schwitzgebel V. M., D. W. Scheel, J. R. Conners, J. Kalamaras, J. E. Lee, D. J. Anderson, L. Sussel, J. D. Johnson, and M. S. German (2000). Expression of neurogenin3 reveals an islet cell precursor population in the pancreas. *Development* 127:3533-3542.

Seaberg R. M., S. R. Smukler, T. J. Kieffer, G. Enikolopov, Z. Asghar, M. B. Wheeler, G. Korbutt and D. van der Kooy (2004). Clonal identification of multipotent precursors from adult mouse pancreas that generate neural and pancreatic lineages. *Nat. Biotechnol.* 22:1115-1124.

Suzuki A., H. Nakauchi and H. Taniguchi (2004). Prospective isolation of multipotent pancreatic progenitors using flow-cytometric cell sorting. *Diabetes* 53:2143-2152.

Teta M., M. M. Rankin, S. Y. Long, G. M. Stein, and J. A. Kushner (2007). Growth and regeneration of adult beta cells does not involve specialized progenitors. *Dev. Cell* 12:817-826.

Trautmann B., H. J. Schlitt, E. G. Hahn, and M. Löhr (1993). Isolation, culture, and characterization of human pancreatic duct cells. *Pancreas* 8:248-54.

Wang R. N., G. Kloppel, and L. Bouwens (1995). Duct-to-islet cell differentiation and islet growth in the pancreas of duct-ligated adult rats. *Diabetologia* 38:1405-1411.

Xu X., J. D'Hoker, G. Stangé, S. Bonné, N. De Leu, X. Xiao, M. Van de Casteele, G. Mellitzer, Z. Ling, D. Pipeleers, L. Bouwens, R. Scharfmann, G. Gradwohl, and H. Heimberg (2008). Beta cells can be generated from endogenous progenitors in injured adult mouse pancreas. *Cell.* 132(2):197-207.

Example 9

Culturing of Human Small Intestinal or Colon Crypts In Vitro

As described in Examples 1 and 2, for the first time, it is now possible to generate long-time culture conditions for mouse small intestine and colon epithelium. Crypt-villus organoids grow through the supplementation of a set of divined growth factors and an extracellular matrix. The organoids contain intestinal stem cells that actively divide and give rise to all major differentiated cell lineages present in the intestine. In this example, we show that these culture conditions are not unique to the mouse intestinal epithelium but can also be used to grow human intestinal epithelium.

Material and Methods
Mouse Colon Organoid Cultures

Mouse organoid cultures were cultured as described in Example 1. Inhibitor of Wnt production (IWP-2) was used to inhibit Wnt secretion (Chen et al., *Nat. Chem. Biol.* 2009 February; 5(2):100-7).

Human Colon Organoid Cultures

Human colon crypts were isolated from resected normal colonic specimen and cultured as organoid structures for seven days using the established organoid culture system (Sato et al., 2009 *Nature*, May 14; 459(7244):262-5). Since this protocol was optimized for mouse-derived organoid cultures, we made a small change by the addition of Wnt3a-conditioned medium, in order to ensure optimal growth of the human colon organoids. To obtain this conditioned medium, Wnt3a is expressed in a cell line by transfecting a suitable expression construct encoding the ligand. The cell line is cultured and the culture medium comprising the secreted ligand is harvested at suitable time intervals. For example, cells start the production of Wnt3a at the moment they reach confluency and stop growing. Culture medium from cells that were not transfected or infected with the empty expression construct was used as a negative control. The conditioned medium was harvested and tested, for example, in an assay wherein luciferase expression is controlled by TCF-responsive elements to quantitate the presence of a Wnt agonist such as Wnt3a (Korinek et al., 1997, *Science* 275:1784-1787).

Results

Figure 31A:
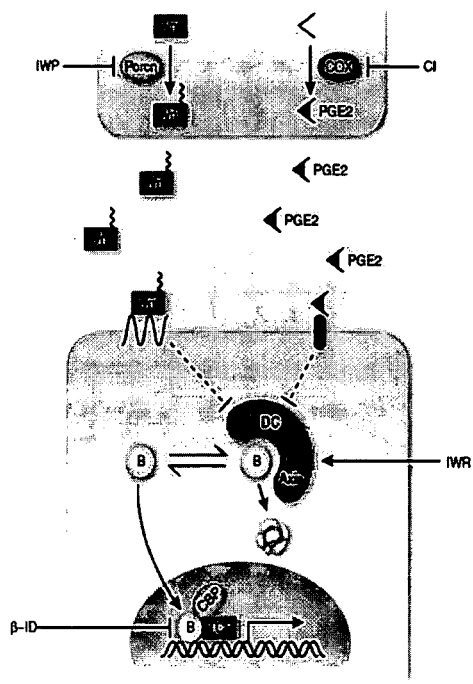
FIG. 31. In vitro crypt cultures produce Wnt ligand(s) (FIG. 31a) Schematic representation of the Wnt pathway. When Wnt ligands are secreted, they can autocrine or paracrine activate the Wnt signaling pathway. Porcupine is important for proper Wnt ligands secretion. IWP inhibitors result in an inhibition of Wnt ligand secretion. (Panel B) Mouse organoids cultured under normal conditions as indicated in Example 1. (Panel C) Incubation of mouse organoid cultures with 1 μM IWP results in cell death of organoid cultures. (Panel D) Addition of Wnt3a-conditioned medium enhances the mouse organoid cultures. (Panel E) IWP-induced organoid death is rescued by the addition of Wnt3a-conditioned medium. A magnification of 10× is shown (Panels B-E).
Figure 31:
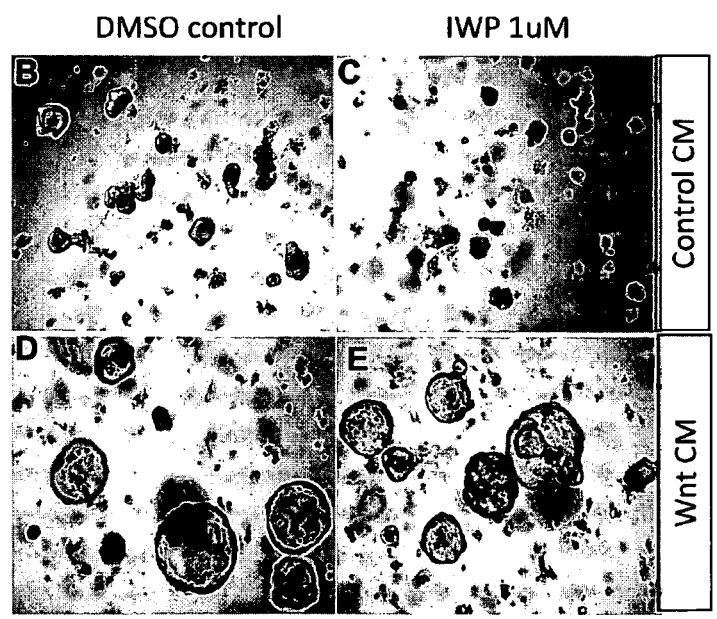

The proliferation of the intestinal epithelium is dependent on the Wnt signaling pathway. The exact location of the Wnt source is, however, unclear (Gregorieff and Clevers, 2005, *Genes Dev. April* 15; 19(8):877-90). Since the mouse intestinal organoids grew in a niche-independent fashion (Sato et al., 2009, *Nature*, May 14; 459(7244):262-5), we assumed that these organoids may produce their own Wnt ligands. To test this, we inhibited Wnt secretion through incubation with a porcupine inhibitor. Porcupine is important for the Wnt secretion (schematic FIG. 31a). Incubation with 1 μM IWP (Chen et al., *Nat. Chem. Biol.* 2009 February; 5(2):100-7) resulted in death of the organoids (FIG. 31, Panels B and C). The organoids could be rescued by addition of Wnt3a-conditioned medium, indicating that the organoids indeed produce Wnt ligands (FIG. 31, Panels D and E).

Figure 32:
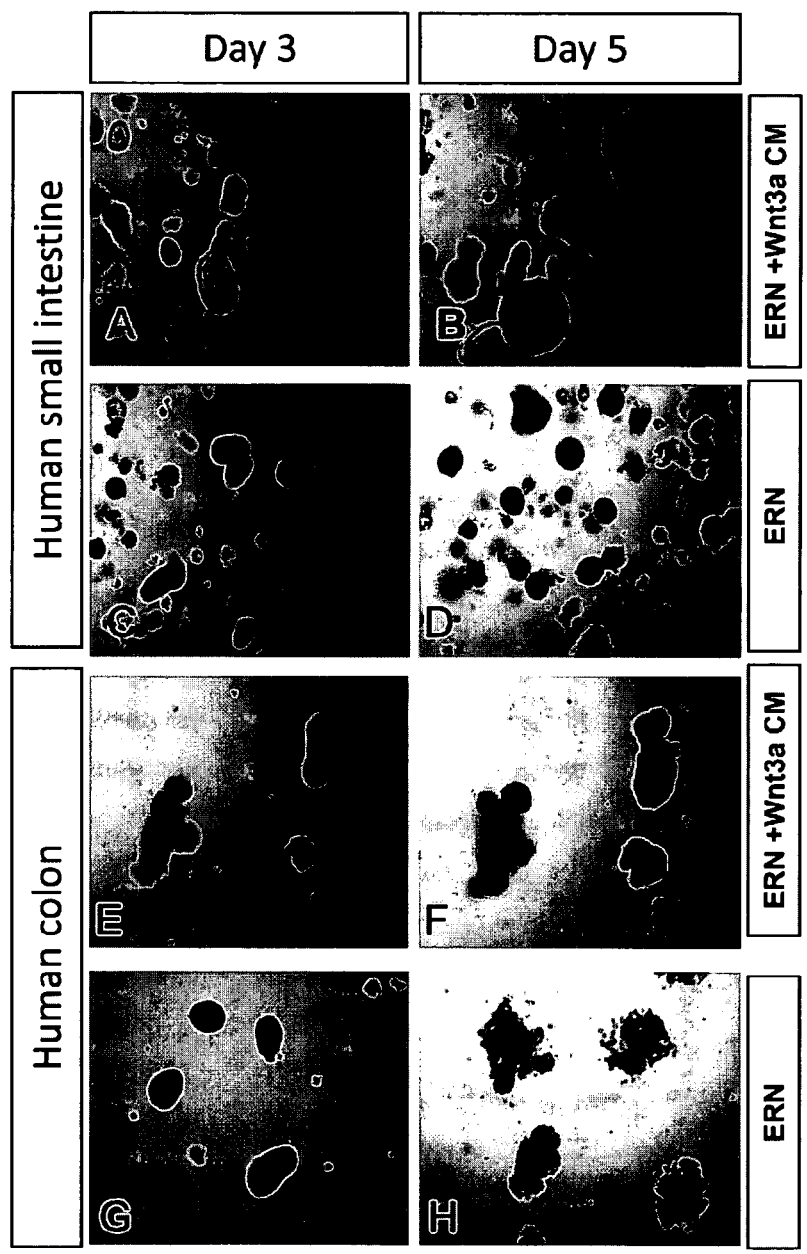
FIG. 32. Establishment of human intestinal crypt culture Human organoids cultured out of small intestine (Panels A-D) and colon (Panels E-H) after three (Panels A, C, E, G) and five (Panels B, D F, H) days in medium supplemented with EGF, Noggin and R-spondin with (Panels A, B, E, F) and without (Panels C, D, G, H) Wnt3a-conditioned medium.

We next tried to culture human intestinal organoids. It turned out that the addition of Wnt3a to the medium was necessary because without it, crypt organoids never formed budding structures and died within five to ten days for the small intestine and in three to four days for the colon (FIG. 32). Overall, the human intestinal crypt organoids grew in a comparable fashion to the mouse organoids cultures. Typically, we obtained up to 80% culture efficiency depending on activity of Wnt-3a-conditioned medium. The human intestinal cultures have been in culture for up to three months. The effect of Wnt-3a in human colon was expected, as it was also observed to enhance the effects in mouse colon organoid culture. The requirement of Wnt-3a in human small intestine and colon may come from lower production of endogenous Wnt ligands by the human organoids, due to the lower numbers of Paneth cells present in the human gut as compared with mouse intestine. So far, there was no reproducible long-term human intestinal culture system, and our culture system is useful, not only to understand human intestinal stem cell biology, but also to apply clinic-oriented tests, such as drug screening.

Example 10

Optimized Culture Conditions for the Growth of Stomach Organoids

As described in Example 5, a culture medium has been identified that can be used to culture stomach epithelium for long periods. Here, we describe the optimized conditions for these stomach organoid cultures.

Materials and Methods

Gastric Unit Isolation, Single Cell Dissociation and EGFP$^{+Ve}$ Cell Sorting

Gastric glands were isolated from mouse pylorus regions as previously described with some modifications (Bjerknes and Cheng, 2002, *Am. J. Physiol. Gastrointest. Liver Physiol.*, September; 283(3):G767-77). Briefly, under the microscope, the stomach was opened along the greater curvature, washed with saline solution and the pylorus isolated. The muscular layer of the stomach was removed and the remaining epithelia was divided into 5 mm pieces and incubated for three to five hours in a buffered saline solution ($Na_2HPO_4$ 28 mM, $KH_2PO_4$ 40 mM, NaCl 480 mM, KCl 8 mM, Sucrose 220 mM, D-Sorbitol 274 mM, DL-Dithiotreitol 2.6 mM) containing 10 mM EDTA (for culturing or staining) or 5 mM EGTA (for RNA isolation) at 4° C. After removal of the chelating agent, the tissue fragments were vigorously suspended in the buffered solution using a 10 ml pipette. After suspension and centrifugation, the sediment was enriched in gastric glands. After gland isolation, cells were collected and resuspended in calcium-free SMEM medium (Invitrogen), supplemented with 10 mg/ml Trypsine and 0.8 Units/μl DNAse I (for microarray analysis) or resuspended in TrypleExpress (GIBCO) supplemented with 0.8 Units/μl DNAase (for culturing purposes). In both cases, after incubation at 37° C. for 20 to 25 minutes, cells were spun down, and filtered through a 40 μM mesh. EGFPhi and EGFPlo cells were sorted by flow cytometry (MoFlo, Beckman Coulter). Single viable epithelial cells were gated by forward scatter and pulse-width parameter. Where stated, cells were either gated for negative staining of propidium iodide, collected in Trizol LS (Invitrogen) and RNA isolated according to the manufacturers' protocol or collected in gastric culture medium, embedded in Matrigel (BD Bioscience) and cultured according to the protocol detailed below.

Gastric Culture

For culturing, isolated gastric glands were counted and a total of 100 glands mixed with 50 μl of Matrigel (BD Bioscience) and plated in 24-well plates. After polymerization of Matrigel, gastric culture medium (Advanced DMEM/F12 supplemented with B27, N2 and N-Acetylcysteine (Invitrogen) containing growth factors (50 ng/m EGF (Peprotech), 1 μg/ml R-spondin 1, 100 ng/ml Noggin (Peprotech), 100 ng/ml FGF10 (Preprotech) and Wnt3A-conditioned media) was overlaid. For the single cell culture, a total of 100 sorted EGFP$_{hi}$ cells/well were collected in gastric culture medium and embedded in Matrigel (BD Bioscience). After polymerization of Matrigel, gastric culture media was overlaid. For the first two days after seeding, the media was also supplemented with 10 μM ROCK inhibitor Y-27632 (Sigma Aldrich), to avoid anoikis. Growth factors were added every second day and the entire medium was changed every four days. For passage, gastric organoids were removed from Matrigel, mechanically dissociated and transferred to fresh Matrigel. Passage was performed every one to two weeks with a 1:5 to 1:8 split ratio. To confirm the Wnt3A requirement, mouse Wnt3A recombinant protein (Stem cell technologies) was supplemented instead of the Wnt3A-conditioned media. For the in vitro tracing experiments, two-week-old gastric organoids were incubated with 100 nM of 4-hydroxytamoxifen in gastric culture medium for 20 hours to activate Lgr5-CreERT2. YFP was subsequently visualized and recorded in live organoids using confocal microscopy (Leica, SP5).

Wnt3a-Conditioned Media

The Wnt3a media was prepared following protocol described elsewhere (Willert et al., 2003, Nature, May 22; 423(6938):448-52). The TOP/FOP assay was used to test the Wnt activity of the Wnt3a-conditioned media and the control-conditioned media, as described by van de Wetering and colleagues (van de Wetering et al., 2001, Cancer Res., January 1; 61(1):278-84). A TOP/FOP ratio≥50 was considered high Wnt media and diluted 1:1 with the gastric organoid culture media. A 1:10 dilution of this high Wnt3a media (TOP/FOP ratio ~5) was considered low Wnt media and used for differentiation purposes.

Gastric Organoid Immunohistochemistry

For immunohistochemistry, gastric organoids were washed once with PBS and immediately fixed with Paraformaldehyde 4% for 15 to 20 minutes at RT. When stated, gastric organoids were embedded in paraffin and processed using standard techniques. For whole-mount staining, samples were permeabilized with PBS 0.5% Triton-X100 1% BSA and incubated o/n with the primary antibodies. Following several washes in PBS 0.3% Triton X100, samples were incubated with the secondary antibody. EdU staining was performed following manufacturer's instructions (Click-IT; Invitrogen). Nuclei were stained with TOPRO3 iodine or Hoescht33342. The images of gastric glands and gastric organoids were acquired using confocal microscopy (Leica, SP5). Three-dimensional reconstruction was performed using Volocity Software (Improvision).

RT-PCR

RNA was extracted from gastric cell cultures or freshly isolated tissue using the RNeasy Mini RNA Extraction Kit (Qiagen) and reverse-transcribed using Moloney Murine Leukemia Virus reverse transcriptase (Promega). cDNA was amplified in a thermal cycler (GeneAmp PCR System 9700; Applied Biosystems, London, UK) as previously described (Huch et al., 2009). Primers used are shown below (Gene symbol followed by Forward (5'-3') and Reverse (5'-3') primers).

```
Lgr5:
GGAAATGCTTTGACACACATTC,     (SEQ ID NO: 24)

GGAAGTCATCAAGGTTATTATAA     (SEQ ID NO: 25)

Gif:
TGAATCCTCGGCCTTCTATG,       (SEQ ID NO: 26)

CAGTTAAAGTTGGTGGCACTTC      (SEQ ID NO: 27)

Pgc:
CCAACCTGTGGGTGTCTTCT,       (SEQ ID NO: 28)

TTAGGGACCTGGATGCTTTG        (SEQ ID NO: 29)

Muc6:
TGCATGCTCAATGGTATGGT,       (SEQ ID NO: 30)

TGTGGGCTCTGGAGAAGAGT        (SEQ ID NO: 31)

Muc5ac:
CCATGAAGTGGGAGTGTGTG,       (SEQ ID NO: 32)

TTGGGATAGCATCCTTCCAG        (SEQ ID NO: 33)

Ghrl:
GCCCAGCAGAGAAAGGAATCCA,     (SEQ ID NO: 34)

GCGCCTCTTTGACCTCTTCC        (SEQ ID NO: 35)

Gast:
GCCAACTATTCCCCAGCTCT,       (SEQ ID NO: 36)

GGCTCTGGAAGAGTGTTGCT        (SEQ ID NO: 37)

Stt:
GAGGCAAGGAAGATGCTGTC,       (SEQ ID NO: 38)

GGGCATCATTCTCTGTCTGG        (SEQ ID NO: 39)

Muc2:
GAACGGGGCCATGGTCAGCA,       (SEQ ID NO: 40)

CATAATTGGTCTTGCATGCC        (SEQ ID NO: 41)

Cdx2:
CTTGCTGCAGACGCTCAAC,        (SEQ ID NO: 42)

TCTGTGTACACCACCCGGTA        (SEQ ID NO: 43)

Hprt:
AAGCTTGCTGGTGAAAAGGA,       (SEQ ID NO: 44)

TTGCGCTCATCTTAGGCTTT        (SEQ ID NO: 45)
```

Results

Figure 33A:
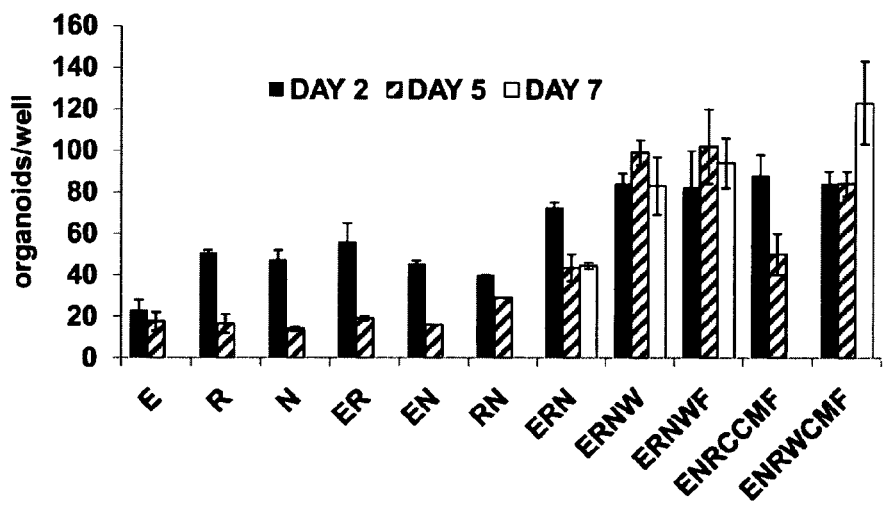
FIG. 33. Establishment of the gastric organoid culture (FIG. 33a) A total of 100 gastric glands/well were seeded in duplicate with EGF (E); R-spondin 1 (R); Noggin (N); EGF+R-spondin 1 (ER); EGF+Noggin (EN); EGF+R-spondin 1+Noggin (ERN); EGF+R-spondin 1+Noggin+Wnt3A (ERNW); EGF+R-spondin 1+Noggin+Wnt3A+FGF10 (ERNWF); EGF+R-spondin 1+Noggin+control-conditioned media+FGF10 (ERNCCMF) or EGF+R-spondin 1+Noggin+Wnt3A-conditioned media+FGF10 (ERNWCMF). The number of gastric organoids was counted two, five and seven days later. Results are shown as mean±SEM of two independent experiments.
(FIG. 33b) A total of 100 gastric glands/well were seeded in duplicate with Wnt3A-conditioned media (ENRWCM) or Wnt3A-conditioned media supplemented with FGF10 (ENRWCMF). The number of budding organoids was counted after seven, fifteen (passage 2) and sixty days (passage 10) in culture.
(FIG. 33c) A total of 100 gastric glands/well were seeded in Wnt3A-conditioned media (WCM)+EGF+Noggin and R-spondin supplemented with either FGF7/KGF (K) or FGF 10 (F) both 100 and 1000 ng/ml has been tested. The number of budding organoids was counted after four days (passage 7) in culture. A representative experiment has been shown.
(FIG. 33d) Isolated gastric glands developing into organoids. Differential-interference contrast images from days 1, 2, 3, 4, 7 after seeding. After one week, cultures required splitting 1:5 or 1:6. Subculturing and maintenance has been performed as described in the supplementary materials and methods section. Representative images of the cultures after 15 days, 3 months, 4.5 and 6 months in culture; (10× magnification).
(FIG. 33e) Example of a five-day-old culture grown in control-conditioned media. Note that the culture is not growing and has failed to foam gland domains. Under these conditions, the culture survived no longer than seven days.
(FIG. 33f) Whole-mount E-Cadherin staining in a three-month-old gastric organoid.
Figure 33B:
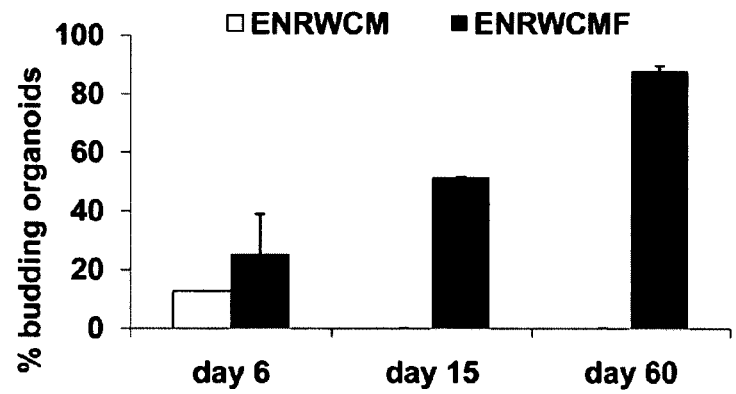
Figure 33C:
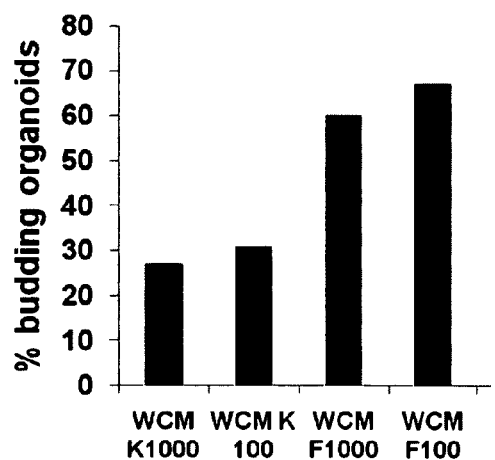
Figure 33D:
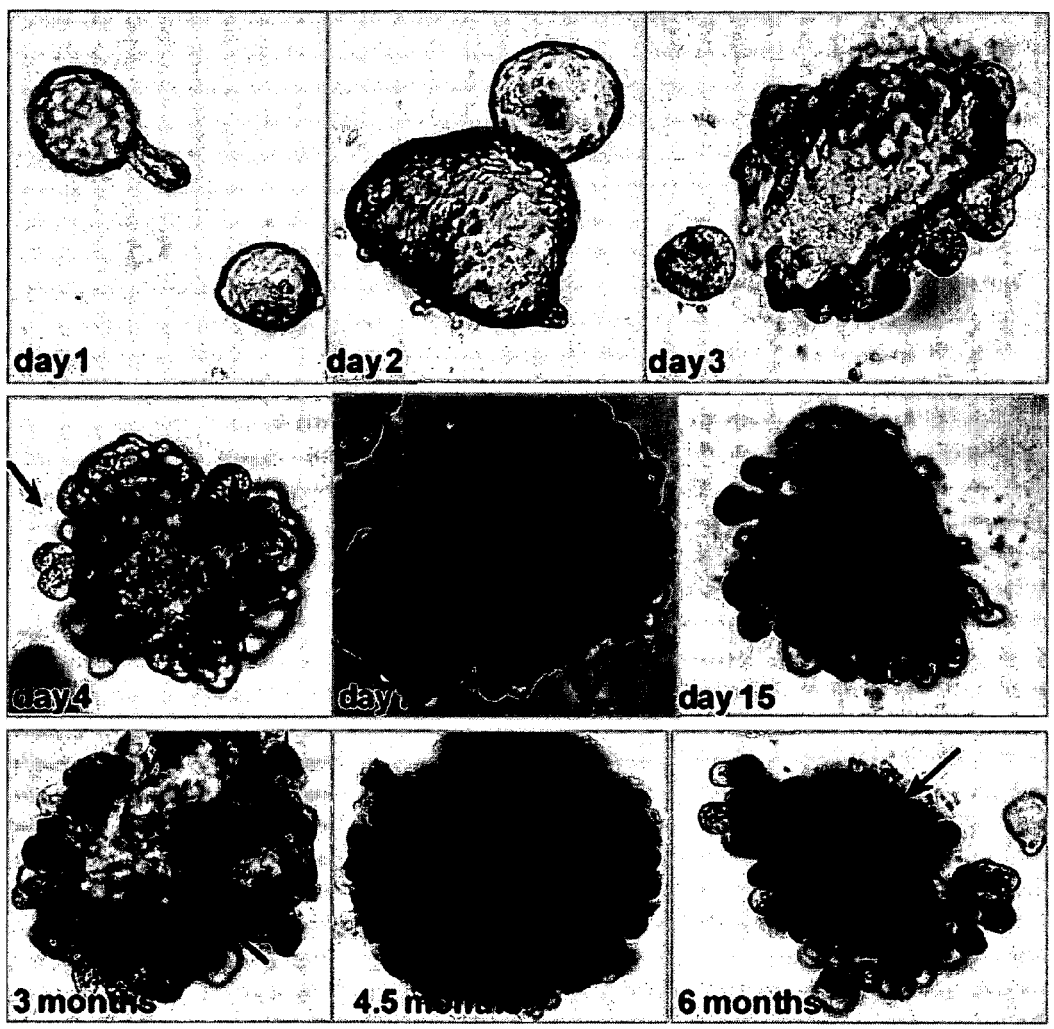
Figure 33E:
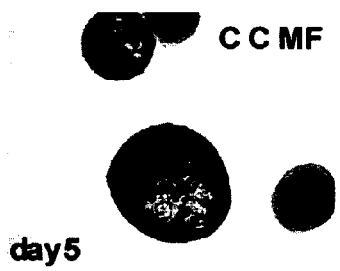
Figure 33F:
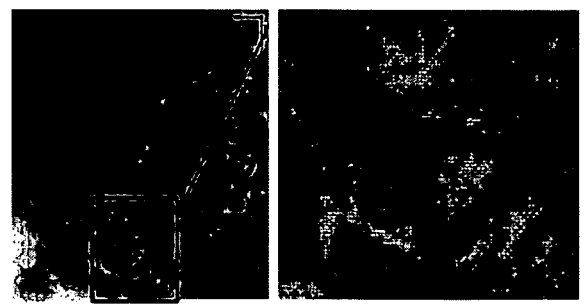

To determine optimal growth of gastric units in vitro, we isolated gastric gland units that were suspended in Matrigel and cultured under different conditions. Gastric culture growth conditions were similar to those of the small intestine cultures (including EGF, Noggin and R-spondin 1), except for a strict dependence on Wnt3A in the form of conditioned media. This requirement was confirmed using purified Wnt3a protein (FIG. 33a). Furthermore, FGF10 proved to be an essential component for driving budding events and for the expansion of the cultures into multi-unit organoids (FIG. 33b). FGF10 can be used to replace FGF7 (KGF), which has been used in Example 5, and even results in a two-fold increase of % of budding organoids four days after the start of the culture (FIG. 33c). The newly formed gastric organoids underwent continuous budding events, while maintaining their polarity, with gastric gland-domain buds distributed around a central lumen (FIG. 33d). In the absence of Wnt3A-conditioned medium, the gastric organoids rapidly deteriorated (FIG. 33e). Each week, organoids were mechanically dissociated and split to one-fifth of their pre-plating density. Cultured pyloric units were single-layered epithelial structures, as evidenced by E-Cad staining (FIG. 33f). We have successfully cultured gastric organoids for at least eight months without any detectable loss of the properties described above.

Figure 34A:
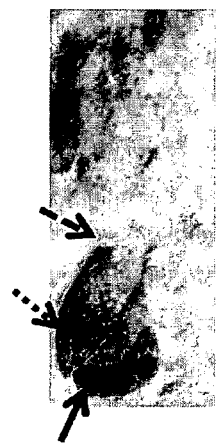
(FIG. 34a) Confocal analysis of a freshly isolated pyloric gastric unit from an Lgr5-EGFP-ires-CreERT2 mouse stomach. Arrows showing GFPhi (grey), GFPlo (black) and GFP-ve (white) distinct populations.
Figure 34B:
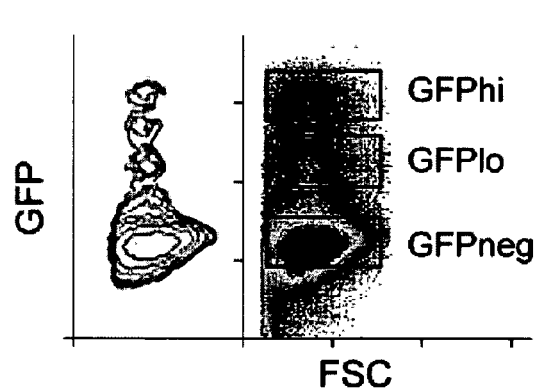
(FIG. 34b) Lgr5-EGFP+ve cells are discriminated from the GFPlo and GFP-ve populations according to their GFP expression level. FSC, forward scatter.
Figure 34C:
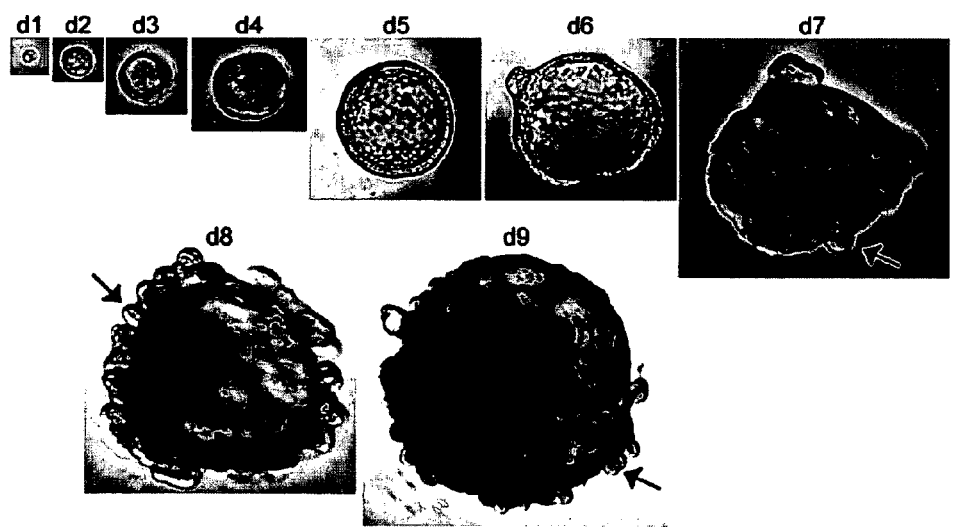
(FIG. 34c) Representative example of a growing organoid originating from a single Lgr5+ve cell. Arrows showing the formation of gland-like domain buds at day 7. Original magnifications: days 1-4: 40× magnification; days 5-6: 20× magnification; days 7-8: 10× magnification; and day 9: 5× magnification.
Figure 34D:
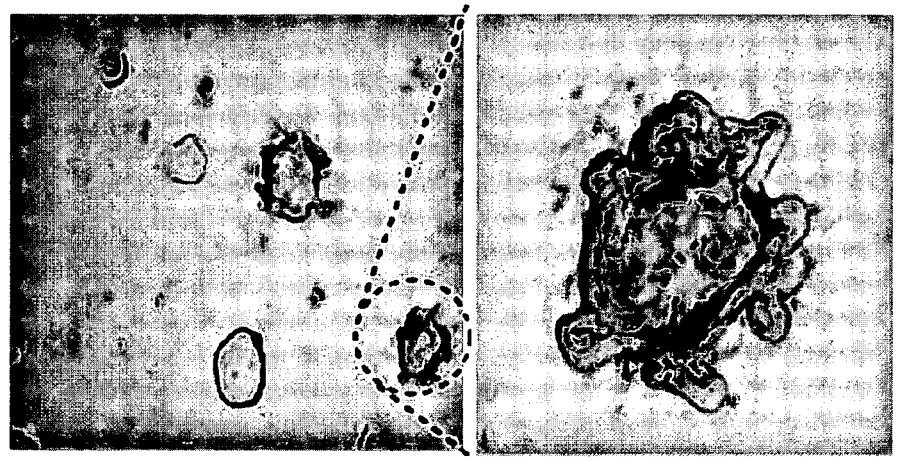
(FIG. 34d) Organoids derived from single Lgr5+ve cells have been dissociated and split every five to seven days. Representative images of a three-month-old culture. Original magnifications: left panel: 4× magnification; right panel: 10× magnification.
Figure 34E:
(FIG. 34e) Confocal analysis of Lgr5 EGFP-expressing cells in a fourteen-day-old gastric culture grown from a single GFPhi cell. Note that Lgr5-GFP+ve cells are located at the bottom of the gland domains (white arrow; 10× magnification).
Figure 34F:
(FIG. 34f) Organoids cultured with the thymidine analogue EdU (red) for 1.5 hours. Only gland domains incorporate EdU (white arrows; 20× magnification). Counterstain, 4,6-diamidino-2-phenylindole (DAPI; nuclear).
Figure 34G:
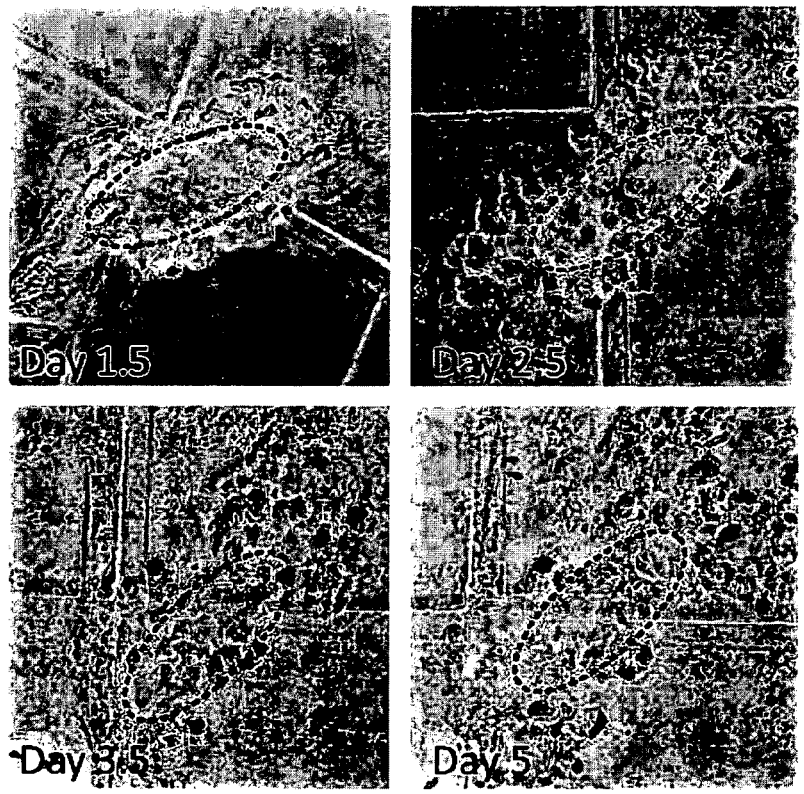
(FIG. 34g) A two-week-old culture from a single-cell culture of Lgr5-EGFP-ires-CreERT2/Rosa26-YFP reporter mouse was stimulated with tamoxifen in vitro for 20 hours, and imaged on the indicated days. YFP fluorescence (yellow) shows that scattered single yellow cells (day 1.5) generate multiple offspring in vitro. Note that YFP+ve cells migrate toward the central lumen (white dotted circle).
Figure 34H:
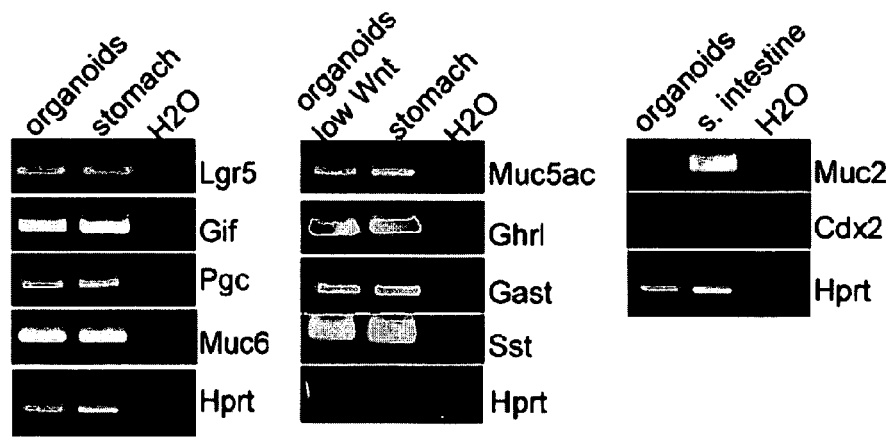
(FIG. 34h) Expression analysis of gastric-specific genes from two-month-old cultures derived from Lgr5+ve single cells. Cultures maintained in high (left panel) or low (middle panel) Wnt3A medium. Note that gastric-derived cultures are negative for intestine-specific genes (right panel).
Figure 34I:
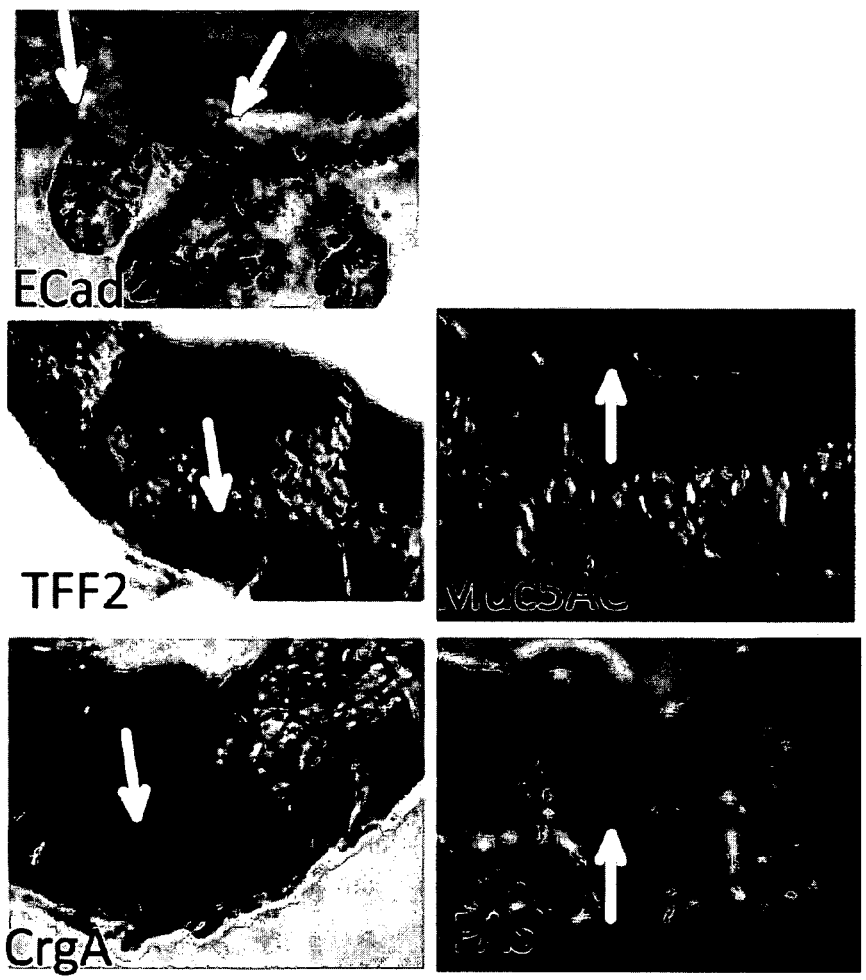
(FIG. 34i) Cultures maintained in low Wnt3A media for at least ten days. Upper panel: confocal image of ECad staining (red, epithelium-derived organoids). Counterstain, Hoescht 33345 (blue). Lower panels: paraffin sections stained for Tff2 (brown, mucous neck cells), periodic acid-Schiff (red, pit cells), MUC5AC (brown, pit cells) and chromogranin A (brown, enteroendocrine cells).

To determine whether gastric Lgr5$^{+ve}$ cells (FIG. 34a) were capable of generating and maintaining pyloric gastric glands units in vitro, we sorted Lgr5-EGFP high cells (FIG. 34b). When single Lgr5-EGFP high cells were sorted, an average of 8% of the cells grew into organoids, whereas the remaining cells died within the first 24 hours. The sorted Lgr5-EGFPhi cells rapidly began dividing and small cyst-like structures were already visible after five days. During the following days, the newly formed (cyst-like) structures started to generate gland-like domains (FIG. 34c). After nine to eleven days in culture, gastric organoids were dissociated manually and split to generate new organoids. Gastric organoids derived from single cells have been successfully re-plated on a weekly basis for at least three months, without losing the properties described (FIG. 34d). From day 7 onward, Lgr5-EGFP expression was restricted to the base of the gland-like domains (FIG. 34e). As evidenced by EdU staining, proliferating cells were located at the base of these gland-like domains (FIG. 34f), while apoptotic caspase 3-positive cells were found extruded into the lumen (data not shown). Lineage tracing was studied in established organoids derived from single Lgr5+ve cells isolated from an Lgr5-EGFP-ires-CreERT2/Rosa26-YFP reporter mouse. Following tamoxifen induction, the YFP+ve reporter gene was rapidly activated in single Lgr5+ve cells within the gland-like domains. Over the next few days, the YFP expression domain expanded considerably within the growing organoids, confirming the contribution of the Lgr5+ve stem cells to organoid growth in vitro (FIG. 34g). The organoids derived from single-cell cultures were single-layered epithelial structures, as evidenced by E-cadherin staining (FIG. 34i). In addition to Lgr5, the cultures expressed the gastric epithelial markers Gastric intrinsic Factor, Mucin 6 and Pepsinogen C. No differentiation to the pit or enteroendocrine lineages was observed under these culture conditions. (This is different from Example 5 where the pit cell lineage was observed. However, in that example, Wnt3a protein was used instead of Wnt-conditioned medium, which is less active. Lowering the Wnt-conditioned medium concentration results in differentiation into the pit cell lineage, see below.) Reduction of the Wnt3A concentration in the culture media resulted in the formation of comparable gastric structures harboring polarized pit cells, as evidenced by the expression of the gastric mucin 5AC (MUC5AC) and Periodic acid-Schiff (PAS), mucous neck cells, as demonstrated by Tff2 expression and some scattered immature enteroendocrine cells (Chromogranin A) (FIGS. 34h and 34i). Addition of additional growth factors like RA, IGF and exendin4 may result into more mature differentiation of stomach cultures toward the various cell lineages. Taken together, these in vivo and in vitro observations demonstrate that Lgr5 is marking a previously unappreciated population of self-renewing, multipotent adult stem cells in the pyloric stomach.

REFERENCES

1. Barker N. et al. Identification of stem cells in small intestine and colon by marker gene Lgr5. *Nature* 449:1003-7 (2007).
2. Bjerknes M. and H. Cheng. Intestinal epithelial stem cells and progenitors. *Methods Enzymol.* 419:337-83 (2006).
3. Barker N., M. van de Wetering, and H. Clevers. The intestinal stem cell. *Genes Dev.* 22:1856-64 (2008).
4. Evans G. S., N. Flint, A. S. Somers, B. Eyden, and C. S. Potten. The development of a method for the preparation of rat intestinal epithelial cell primary cultures. *J. Cell Sci.* 101 (Pt 1), 219-31 (1992).
5. Whitehead R. H., K. Demmler, S. P. Rockman, and N. K. Watson. Clonogenic growth of epithelial cells from normal colonic mucosa from both mice and humans. *Gastroenterology* 117:858-65 (1999).
6. Fukamachi H. Proliferation and differentiation of fetal rat intestinal epithelial cells in primary serum-free culture. *J. Cell Sci.* 103 (Pt 2), 511-9 (1992).
7. Perreault N. and B. Jean-Francois. Use of the dissociating enzyme thermolysin to generate viable human normal intestinal epithelial cell cultures. *Exp. Cell Res.* 224:354-64 (1996).
8. Korinek V. et al. Depletion of epithelial stem-cell compartments in the small intestine of mice lacking Tcf-4. *Nat. Genet.* 19:379-83 (1998).
9. Pinto D., A. Gregorieff, H. Begthel and H. Clevers. Canonical Wnt signals are essential for homeostasis of the intestinal epithelium. *Genes Dev.* 17:1709-13 (2003).
10. Kuhnert F., et al. Essential requirement for Wnt signaling in proliferation of adult small intestine and colon revealed by adenoviral expression of Dickkopf-1. *Proc. Natl. Acad. Sci. U.S.A.* 101:266-71 (2004).
11. Kim K. A., et al. Mitogenic influence of human R-spondin 1 on the intestinal epithelium. *Science* 309:1256-9 (2005).
12. Dignass A. U. and A. Sturm. Peptide growth factors in the intestine. *Eur. J. Gastroenterol. Hepatol.* 13:763-70 (2001).
13. Haramis A. P., et al. De novo crypt formation and juvenile polyposis on BMP inhibition in mouse intestine. *Science* 303:1684-6 (2004).
14. Hofmann C. et al. Cell-cell contacts prevent anoikis in primary human colonic epithelial cells. *Gastroenterology* 132:587-600 (2007).
15. Sasaki T., R. Giltay, U. Talts, R. Timpl, and J. F. Talts. Expression and distribution of laminin alpha1 and alpha2 chains in embryonic and adult mouse tissues: an immunochemical approach. *Exp. Cell Res.* 275:185-99 (2002).
16. Stingl J., C. J. Eaves, I. Zandieh and J. T. Emerman. Characterization of bipotent mammary epithelial progenitor cells in normal adult human breast tissue. *Breast Cancer Res. Treat.* 67:93-109 (2001).
17. St Clair W. H. and J. W. Osborne. Crypt fission and crypt number in the small and large bowel of postnatal rats. *Cell Tissue Kinet.* 18:255-62 (1985).
18. Bathe E., et al. Beta-catenin and TCF mediate cell positioning in the intestinal epithelium by controlling the expression of EphB/ephrinB. *Cell* 111:251-63 (2002).
19. Srinivas S., et al. Cre reporter strains produced by targeted insertion of EYFP and ECFP into the ROSA26 locus. *BMC Dev. Biol.* 1:4 (2001).
20. Soriano P. Generalized lacZ expression with the ROSA26 Cre reporter strain. *Nat. Genet.* 21:70-1 (1999).
21. Stingl J. et al. Purification and unique properties of mammary epithelial stem cells. *Nature* 439:993-7 (2006).
22. Watanabe K. et al. A ROCK inhibitor permits survival of dissociated human embryonic stem cells. *Nat. Biotechnol.* 25:681-6 (2007).
23. van Es J. H., et al. Notch/gamma-secretase inhibition turns proliferative cells in intestinal crypts and adenomas into goblet cells. *Nature* 435:959-63 (2005).
24. Li L., et al. The human homolog of rat Jagged1 expressed by marrow stroma inhibits differentiation of 32D cells through interaction with Notch1. *Immunity* 8:43-55 (1998).
25. Cheng H. and C. P. Leblond. Origin, differentiation and renewal of the four main epithelial cell types in the mouse small intestine. I. Columnar cell. *Am. J. Anat.* 141:461-79 (1974).
26. Powell D. W., et al. Myofibroblasts. II. Intestinal subepithelial myofibroblasts. *Am. J. Physiol.* 277:C183-201 (1999).
27. Yen T. H. and N. A. Wright. The gastrointestinal tract stem cell niche. *Stem Cell Rev.* 2:203-12 (2006).
28. Kedinger M., et al. Intestinal epithelial-mesenchymal cell interactions. *Ann. N.Y. Acad. Sci.* 859:1-17 (1998).
29. Spradling A., D. Drummond-Barbosa, and T. Kai. Stem cells find their niche. *Nature* 414:98-104 (2001).
30. Li L. T. Xie. Stem cell niche: structure and function. *Annu. Rev. Cell Dev. Biol.* 21:605-31 (2005).
31. Binnerts M. E., et al., *PNAS* 104:14700-5 (2007).
32. Sawada, et al. *Int. J. Exp. Pathol.* 72:407-21 (1991).

The invention claimed is:

1. An in vitro method for obtaining a crypt villus organoid or a colon crypt organoid, the method comprising:
   incubating an epithelial stem cell or an isolated tissue fragment comprising an epithelial stem cell with an extracellular matrix, and
   culturing the stem cell or isolated tissue fragment for a length of time sufficient to be able to observe formation of a crypt villus organoid or a colon crypt organoid, in an animal or human cell culture medium comprising:
   a Bone Morphogenetic Protein (BMP) inhibitor,
   between 5 and 500 ngram/ml of a mitogenic growth factor, and
   a Wnt agonist, and
   obtaining from the culture medium a crypt villus organoid or a colon crypt organoid.

2. The method according to claim 1, wherein the BMP inhibitor is Noggin, the mitogenic growth factor is Epidermal Growth Factor, and the Wnt agonist comprises any one of R-spondin 1 through R-spondin 4.

3. The method according to claim 2, wherein the Wnt agonist comprises any one of R-spondin 1 through R-spondin 4 and Wnt-3a.

4. The method according to claim 2, wherein the cell culture medium further comprises a Rock (Rho-kinase) inhibitor selected from the group consisting of Y-27632, Fasudil, and H-1152.

5. The method according to claim 2, wherein the cell culture medium further comprises a notch agonist.

6. The method according to claim 2, wherein the cell culture medium further comprises brain-derived neurotrophic factor.

7. The method according to claim 1, wherein the BMP inhibitor is selected from the group consisting of Noggin, DAN, Cerberus and Gremlin.

8. The method according to claim 7, wherein the Wnt agonist is selected from the group consisting of one or more of Wnt, R-spondin 1 through R-spondin 4, Norrin, and a GSK-inhibitor.

9. The method according to claim 7, wherein the Wnt agonist comprises any one of R-spondin 1 through R-spondin 4 and Wnt-3a.

10. The method according to claim 7, wherein the mitogenic growth factor is EGF.

11. The method according to claim 7, wherein the cell culture medium further comprises a Rock (Rho-kinase) inhibitor selected from the group consisting of Y-27632, Fasudil, and H-1152.

12. The method according to claim 7, wherein the cell culture medium further comprises a notch agonist.

13. The method according to claim 7, wherein the cell culture medium further comprises brain-derived neurotrophic factor.

14. The method according to claim 1, wherein the Wnt agonist is selected from the group consisting of one or more of Wnt, R-spondin 1 through R-spondin 4, Norrin, and a GSK-inhibitor.

15. The method according to claim 14, wherein the Wnt agonist comprises any one of R-spondin 1 through R-spondin 4 and Wnt-3a.

16. The method according to claim 14, wherein the mitogenic growth factor is EGF.

17. The method according to claim 14, wherein the cell culture medium further comprises a Rock (Rho-kinase) inhibitor selected from the group consisting of Y-27632, Fasudil, and H-1152.

18. The method according to claim 14, wherein the cell culture medium further comprises a notch agonist.

19. The method according to claim 14, wherein the cell culture medium further comprises brain-derived neurotrophic factor.

20. The method according to claim 1, wherein the Wnt agonist is one of R-spondin 1 through R-spondin 4 and Wnt-3a.

21. The method according to claim 20, wherein the cell culture medium further comprises a Rock (Rho-kinase) inhibitor selected from the group consisting of Y-27632, Fasudil, and H-1152.

22. The method according to claim 20, wherein the cell culture medium further comprises a notch agonist.

23. The method according to claim 20, wherein the cell culture medium further comprises brain-derived neurotrophic factor.

24. The method of claim 1, wherein the cell culture medium further comprises a Rock (Rho-kinase) inhibitor selected from the group consisting of Y-27632, Fasudil, and H-1152.

25. The method according to claim 24, wherein the cell culture medium further comprises a notch agonist.

26. The method according to claim 24, wherein the cell culture medium further comprises brain-derived neurotrophic factor.

27. The method according to claim 1, wherein the cell culture medium further comprises a notch agonist.

28. The method according to claim 27, wherein the cell culture medium further comprises brain-derived neurotrophic factor.

29. The method according to claim 1, wherein the mitogenic growth factor is Epidermal Growth Factor.

30. The method according to claim 1, wherein the epithelial stem cell is an adenoma cell.

31. An in vitro method for obtaining and/or culturing a colon crypt, the method comprising:
   culturing epithelial stem cells or isolated tissue fragments comprising epithelial stem cells in contact with an extracellular matrix for a length of time sufficient to be able to observe formation of a colon crypt, in a medium comprising Noggin, EGF, any one of R-spondin 1 through R-spondin 4 and/or Wnt3, B27, N2, and N-Acetylcysteine; and
   obtaining from the culture medium a colon crypt.

32. The method according to claim 31, wherein the epithelial stem cells are adenoma cells.

33. An in vitro method for obtaining a crypt villus organoid or colon crypt organoid, the method comprising:
   culturing epithelial stem cells or isolated tissue fragments comprising epithelial stem cells on an extracellular matrix for a length of time sufficient to be able to observe formation of a crypt villus organoid or a colon crypt organoid, in an animal or human cell culture medium comprising:
   a Bone Morphogenetic Protein (BMP) inhibitor;
   a Wnt agonist; and
   between 5 and 500 nanogram/ml of Epidermal Growth Factor (EGF); and
   obtaining from the culture medium a crypt villus organoid or a colon crypt organoid.

34. The method according to claim 33, wherein the epithelial stem cells are adenoma cells.

35. An in vitro method for obtaining a crypt villus organoid or a colon crypt organoid the method comprising:
   incubating an epithelial stem cell or an isolated tissue fragment comprising an epithelial stem cell with an extracellular matrix, wherein the epithelial stem cell is an adenoma cell, and
   culturing the stem cell or isolated tissue fragment for a length of time sufficient to be able to observe formation of a crypt villus organoid or a colon crypt organoid, in an animal or human cell culture medium comprising:
   a Bone Morphogenetic Protein (BMP) inhibitor, and
   between 5 and 500 ngram/ml of a mitogenic growth factor, and
   obtaining from the culture medium a crypt villus organoid or a colon crypt organoid.

* * * * *